United States Patent
Fernandez Rodriguez et al.

(10) Patent No.: US 11,584,918 B2
(45) Date of Patent: Feb. 21, 2023

(54) TRANSCRIPTIONAL CONTROL IN PROKARYOTIC CELLS USING DNA-BINDING REPRESSORS

(71) Applicant: Eligo Bioscience, Paris (FR)

(72) Inventors: Jesus Fernandez Rodriguez, Paris (FR); Antonina Krawczyk, Paris (FR); Xavier Duportet, Paris (FR)

(73) Assignee: ELIGO BIOSCIENCE, Paris (FR)

( * ) Notice: Subject to any disclaimer, the term of this patent is extended or adjusted under 35 U.S.C. 154(b) by 97 days.

(21) Appl. No.: 16/819,935

(22) Filed: Mar. 16, 2020

(65) Prior Publication Data
US 2020/0291363 A1 Sep. 17, 2020

Related U.S. Application Data

(60) Provisional application No. 62/818,903, filed on Mar. 15, 2019.

(51) Int. Cl.
| | |
|---|---|
| *C12N 7/00* | (2006.01) |
| *C12N 9/22* | (2006.01) |
| *C12N 15/87* | (2006.01) |
| *C12N 15/10* | (2006.01) |

(52) U.S. Cl.
CPC ......... *C12N 7/00* (2013.01); *C12N 9/22* (2013.01); *C12N 15/102* (2013.01); *C12N 15/87* (2013.01); *C12N 2310/20* (2017.05)

(58) Field of Classification Search
None
See application file for complete search history.

(56) References Cited

U.S. PATENT DOCUMENTS 6,316,412 B1 * 11/2001 Ginsberg ............. C12N 5/0068 514/9.3

OTHER PUBLICATIONS

Marschall, et al., "Tunable recombinant protein expression in *E. coli*: promoter systems and genetic constraints," Appl. Microbiol. Biotechnol., (2017), vol. 101, No. 2; pp. 501-512.
Brautaset, et al., "Positively regulated bacterial expression systems," Microb. Biotechnol., (Jan. 2009); vol. 2, No. 1; pp. 15-30.
Mijakovic, et al., "Tunable promoters in systems biology," Curr. Opin. Biotechnol., (Jun. 2005), vol. 16, No. 3; pp. 329-335. (Abstract Only).
De Boer, et al., "The tac promoter: a functional hybrid derived from the trp and lac promoters," Proc. Natl. Acad. Sci. U. S. A., (Jan. 1983), vol. 80, No. 1; pp. 21-25.
Guzman, et al. "Tight regulation, modulation, and high-level expression by vectors containing the arabinose PBAD promoter," J. Bacteriol., (Jul. 1995), vol. 177, No. 14; pp. 4121-4130.
Skerra, et al., "Use of the tetracycline promoter for the tightly regulated production of a murine antibody fragment in *Escherichia coli*," Gene, (Dec. 1994), vol. 151, No. 1; pp. 131-135 (Abstract Only).
Valdez-Cruz, et al., "Production of recombinant proteins in *E. coli* by the heat inducible expression system based on the phage lambda pL and/or pR promoters," Microb. Cell Factories, (Mar. 2010), vol. 9; No. 18; pp. 1-16.
Studier, et al., "Use of bacteriophage T7 RNA polymerase to direct selective high-level expression of cloned genes," J. Mol. Biol., (May 1986); vol. 189, No. 1; pp. 113-130 (Abstract Only).
Rosano et al., "Recombinant protein expression in *Escherichia coli*: advances and challenges," Front. Microbiol., (Apr. 2014); vol. 5, Article 172; pp. 1-17.
Stanton, et al., "Genomic mining of prokaryotic repressors for orthogonal logic gates," Nat. Chem. Biol., (Feb. 2014); vol. 10, No. 2; pp. 99-105.
Saïda, et al., "Expression of highly toxic genes in *E. coli*: special strategies and genetic tools," Curr. Protein Pept. Sci., (Feb. 2006), vol. 7, No. 1; pp. 47-56.
Cronan, "Cosmid-Based System for Transient Expression and Absolute Off-to-On Transcriptional Control of *Escherichia coli* Genes," J. Bacteriol., (Nov. 2003), vol. 185, No. 22; pp. 6522-6529.
Cronan, "Improved Plasmid-Based System for Fully Regulated Off-To-On Gene Expression in *Escherichia coli*: Application to Production of Toxic Proteins," Plasmid, (Jan. 2013), vol. 69, No. 1; pp. 81-89.
Bikard et al., "Exploiting CRISPR-Cas nucleases to produce sequence-specific antimicrobials," Nat. Biotechnol., (Nov. 2014), vol. 32, No. 11; pp. 1146-1150.
Fernandez-Rodriguez, et al., "Memory and Combinatorial Logic Based on DNA Inversions: Dynamics and Evolutionary Stability," ACS Synth. Biol., (Dec. 2015), vol. 4, No. 12; pp. 1361-1372.
Manson et al., "Tryptophan operon regulation in interspecific hybrids of enteric bacteria.," J. Bacteriol., (May 1976), vol. 126, No. 2; pp. 679-689.
Meyer, et al., "*Escherichia coli* 'Marionette' strains with 12 highly optimized small-molecule sensors," Nat. Chem. Biol., (Feb. 2019), vol. 15, No. 2; pp. 196-211.
Bikard, et al., "Programmable repression and activation of bacterial gene expression using an engineered CRISPR-Cas system," Nucleic Acids Res., (Aug. 2013); vol. 41, No. 15, pp. 7429-7437.
Qi et al., "Repurposing CRISPR as an RNA-Guided Platform for Sequence-Specific Control of Gene Expression," Cell, (Feb. 2013), vol. 152, No. 5; pp. 1173-1183.

(Continued)

*Primary Examiner* — James D Schultz
(74) *Attorney, Agent, or Firm* — Carter, DeLuca & Farrell LLP; Carmella Stephens

(57) ABSTRACT

The present disclosure relates generally to methods and compositions for transferring a genetic circuit from one prokaryotic cell ("donor cell") to another prokaryotic cell ("recipient cell" or "target cell" which are used interchangeably herein). More specifically, the present disclosure relates to prokaryotic donor cells comprising (i) a genetic circuit of interest and (ii) one or more expressed transcriptional repressor proteins and the use of said donor cells in the efficient transfer of the genetic circuit into a prokaryotic recipient cell. The genetic circuit includes nucleic acid sequences encoding a RNA molecule or protein of interest.

19 Claims, 4 Drawing Sheets

Specification includes a Sequence Listing.

(56) References Cited

OTHER PUBLICATIONS

Cui et al., "Consequences of Cas9 cleavage in the chromosome of *Escherichia coli*," Nucleic Acids Res., (May 2016), vol. 44, No. 9; pp. 4243-4251.
Cho, et al., "High-Level dCas9 Expression Induces Abnormal Cell Morphology in *Escherichia coli*," ACS Synth. Biol., (Apr. 2018), vol. 7, No. 4; pp. 1085-1094.
Fernandez-Rodriguez et al., "Post-translational control of genetic circuits using Potyvirus proteases." Nucleic Acids Res., (Jul. 2016), vol. 44, No. 13; pp. 6493-6502.
Wang, "Lysis Timing and Bacteriophage Fitness" Genetics, (Jan. 2006), vol. 172, No. 1; pp. 17-26.
Sleight et al., "Designing and engineering evolutionary robust genetic ciicuits," J. Biol. Eng., (Nov. 2010), vol. 4, No. 1; pp. 1-20.
Elowitz et al., "A synthetic oscillatory network of transcriptional regulators," Nature, (Jan. 2000), vol. 403, No. 6767; pp. 335-338.
Glick, "Metabolic load and heterologous gene expression," Biotechnol. Adv., (1995), vol. 13, No. 2, pp. 247-261.
Scott, et al., "Interdependence of Cell Growth and Gene Expression: Origins and Consequences," Science, (Nov. 2010), vol. 330, No. 6007; pp. 1099-1102.
Sleight et al., "Visualization of Evolutionary Stability Dynamics and Competitive Fitness of *Escherichia coli* Engineered with Randomized Multigene Circuits," ACS Synth. Biol., (Sep. 2013), vol. 2, No. 9; pp. 519-528.
Bienick et al., "The Interrelationship between Promoter Strength, Gene Expression, and Growth Rate," PLoS ONE, (Oct. 2014), vol. 9, Issue 10 (e109105); pp. 1-10.
Tilg et al., "The intestinal microbiota fuelling metabolic inflammation," Nature Reviews Immunology, (2020), vol. 20; pp. 40-54.
International Search Report and Written Opinion of the International Searching Authority, dated May 13, 2020, corresponding to counterpart International Application No. PCT/EP2020/057112; 13 total pages.
Conte et al., "pGOODs: New Plasmids For The Co-Expression of Proteins in *Escherichia Coli*," Biotechnology Letters, vol. 33, No. 9, Apr. 23, 2011; pp. 1815-1821.
Fernandez-Rodriguez et al., "Post-Translational Control of Genetic Circuits Using Potyvirus Proteases," Nucleic Acids Research, vol. 44, No. 13, Jun. 13, 2016; pp. 6493-6502.
Warren et al., "Construction and Characterization of a Highly Regulable Expression Vector, pLAC11, and Its Multipurpose Derivatives, pLAC22 and pLAC33," Plasmid, vol. 44, No. 2, Sep. 1, 2000; pp. 138-151.
Komeda, "Fusions of Flagellar Operons to Lactose Genes on a Mu lac Bacteriophase," Journal of Bacteriology, vol. 150, No. 1, Apr. 1982; pp. 16-26.
Saida et al., "Expression of Highly Toxic Genes in *E-Coli*: Special Strategies and Genetic Tools," Current Protein and Peptide Science, vol. 7, No. 1, Feb. 1, 2006; pp. 47-56.

* cited by examiner

SEQUENCE LISTING

<160> NUMBER OF SEQ ID NOS: 11

<210> SEQ ID NO 1
<211> LENGTH: 200
<212> TYPE: PRT
<213> ORGANISM: Artificial Sequence
<220> FEATURE:
<223> OTHER INFORMATION: PhlF repressor protein

<400> SEQUENCE: 1

```
Met Ala Arg Thr Pro Ser Arg Ser Ser Ile Gly Ser Leu Arg Ser Pro
1               5                   10                  15

His Thr His Lys Ala Ile Leu Thr Ser Thr Ile Glu Ile Leu Lys Glu
            20                  25                  30

Cys Gly Tyr Ser Gly Leu Ser Ile Glu Ser Val Ala Arg Arg Ala Gly
        35                  40                  45

Ala Ser Lys Pro Thr Ile Tyr Arg Trp Trp Thr Asn Lys Ala Ala Leu
    50                  55                  60

Ile Ala Glu Val Tyr Glu Asn Glu Ser Glu Gln Val Arg Lys Phe Pro
65                  70                  75                  80

Asp Leu Gly Ser Phe Lys Ala Asp Leu Asp Phe Leu Leu Arg Asn Leu
                85                  90                  95

Trp Lys Val Trp Arg Glu Thr Ile Cys Gly Glu Ala Phe Arg Cys Val
            100                 105                 110

Ile Ala Glu Ala Gln Leu Asp Pro Ala Thr Leu Thr Gln Leu Lys Asp
        115                 120                 125

Gln Phe Met Glu Arg Arg Arg Glu Met Pro Lys Lys Leu Val Glu Asn
    130                 135                 140

Ala Ile Ser Asn Gly Glu Leu Pro Lys Asp Thr Asn Arg Glu Leu Leu
145                 150                 155                 160

Leu Asp Met Ile Phe Gly Phe Cys Trp Tyr Arg Leu Leu Thr Glu Gln
                165                 170                 175

Leu Thr Val Glu Gln Asp Ile Glu Glu Phe Thr Phe Leu Leu Ile Asn
            180                 185                 190

Gly Val Cys Pro Gly Thr Gln Arg
        195                 200
```

<210> SEQ ID NO 2
<211> LENGTH: 600
<212> TYPE: DNA
<213> ORGANISM: Artificial Sequence
<220> FEATURE:
<223> OTHER INFORMATION: DNA sequence encoding PhlF repressor protein

<400> SEQUENCE: 2

```
atggcacgta ccccgtcacg tagtagcatt ggtagcctgc gtagtccgca tacccataaa      60
gcaattctga ccagtaccat cgagatcctg aaagaatgtg gttatagcgg actgagcatt     120
gaaagcgttg cacgtcgtgc cggagcaagc aaaccgacca tttatcgttg gtggacgaat     180
aaagcagcac tgattgccga agtgtatgaa aatgaaagcg aacaggtgcg taaatttccg     240
gatctgggta gctttaaagc agatctggat tttttactgc gtaatttatg gaaagtttgg     300
cgtgaaacta tttgcggtga agcatttcgt tgtgttattg cagaagctca gctggatcct     360
gcaaccctga cccagttaaa ggatcaattt atggaacgtc gtcgtgagat gccgaaaaaa     420
ctggttgaaa atgccattag caatggtgaa ctgccgaaag ataccaatcg tgaacttctt     480
ctggatatga ttttggtttt tgttggtat cgcctgttaa ccgaacagct gaccgttgaa     540
```

-continued caggatattg aagaatttac cttccttctg attaatggtg tttgtccggg tactcagcgt    600

<210> SEQ ID NO 3
<211> LENGTH: 51
<212> TYPE: DNA
<213> ORGANISM: Artificial Sequence
<220> FEATURE:
<223> OTHER INFORMATION: PhlF promoter-operator sequence

<400> SEQUENCE: 3
tctgattcgt taccaattga catgatacga aacgtaccgt atcgttaagg t              51

<210> SEQ ID NO 4
<211> LENGTH: 6504
<212> TYPE: DNA
<213> ORGANISM: Artificial Sequence
<220> FEATURE:
<223> OTHER INFORMATION: Plasmid containing Cas9 under the control of a
      PphlF promoter and a constitutive sgRNA guide targeting lacZ

<400> SEQUENCE: 4
ttttgccgtt acgcactact ttagtcagtt ccgcagtacc gtcagtagct gaacaggagg    60
gacagtgttg ataaagcgcc aacttttgc gaaaatgttg cacgtaagac aactttcacc    120
ataatgaaat aagatcacta ctattttttg agttatcgag atttcgcaag ctaaggaagc    180
taaaatggag aaaaaaatca ctggatatac tacagttgat ataagtcaat ggcatcgtaa    240
agaacatttt gaggcattcc agtcagttgc tcagtgcacc tataaccaaa ccgttcagct    300
ggatattacg gcctttttaa aaccgtaaa gaaaaataag cacaagtttt atccggcctt    360
tattcacatt cttgcccgcc tgatgaatgc acatccggag tttcgtatgg caatgaaaga    420
cggtgagctg gtgatatggg atagtgttca cccttgttac accgttttcc atgagcaaac    480
tgaaacgttt tcatcgctct ggtcagaata ccacgacgat ttccggcagt ttctacacat    540
atatagtcaa gatgtggcgt gttacggtga aacttagca tatttcccta aagggtttat    600
cgaaaatatg ttttttcgtca gtgccaatcc gtgggtgagt tcaccagtt tgatttaaa     660 cgtagcaaat atggacaact tcttcgcccc cgttttcact atgggaaaat attatacgca    720
aggcgacaag gtgttaatgc cactggcgat ccaagttcat catgccgttt gtgatggctt    780
ccatgtcggc agaatgctta atgaattaca acaatactgc gatgagtggc agggcgggc     840 gtaatccggc aaggaaacac tgaaaaaagc ccgcacctga cagtgcgggc tttttttttc    900
gaccaaaggt atgcacatgc tatagacttc tggtgctacc cgactgacag ctagctcagt    960
cctaggtata atgctagccg tcgtgactgg gaaaacccgt tttagagcta gaaatagcaa    1020
gttaaaataa ggctagtccg ttatcaactt gaaaaagtgg caccgagtcg gtgcttttt     1080 tgagatcaaa catccactag tcccttacg cacgttgtga tatgtagatg ataatcatta    1140
tcactttacg ggtcctttcc ggtgatccga caggttacgg ggcggcgacc tcgcgggttt    1200
tcgctattta tgaaaattt ccggtttaag gcgtttccgt tcttcttcgt cataacttaa    1260 tgttttatt taaaataccc tctgaaaaga aaggaaacga caggtgctga agcgaggct     1320 ttttggggcg ttcggctaaa cccaaaagta aaaacccgcc gaagcgggtt ttaacgtaaa    1380
acaggtgaaa ctgactttaa cgttattagt caccgcccaa ctgactcaga tcaatacgag    1440
tttcatacag gccagtgatg ctctggtgaa taagagttgc atctaagact tctttagtgg    1500
aggtgtaacg tttacgatcg atcgtggtgt cgaagtattt gaaggctgcc ggagcaccaa    1560
gattagtcag cgtgaacagg tgaatgatgt tttctgcctg ttcacggatc ggtttatcac    1620

```
ggtgtttatt gtaggcgctc aggactttat ccagattcgc gtccgccaga attacgcgtt      1680
tgctaaactc agaaatctgt tcaataatct cgtccagata tgtttgtgc tgttccacga       1740 acagctgttt ctgctcatta tcttccggac tacctttcag tttctcgtag tgcgaggcca     1800
gatacaggaa gttcacgtac ttggacggaa gggccaattc gttcccttt tgcagttcac      1860 ccgcagacgc taacatacgt ttacgaccat tttccagttc gaacagggaa tacttcggca     1920
gtttgataat cagatctttc tttacttcct tgtaccccttt cgcttcgagg aagtcaatcg    1980 ggttttttc gaaagagcta cgttccataa tggtgatgcc taaaagttct ttcactgatt      2040
tcagtttttt tgatttaccc ttttcgactt tggcgactac cagaacgctg tatgccacgg     2100
ttggagaatc gaagccaccg tatttcttcg gatcccagtc tttcttacgc gcgatcagtt    2160
tgtcggagtt gcgtttcggc agaatggatt ccttgctgaa accgccagtc tgtacctcag    2220 tcttttttaac gatgtttact tgaggcatgg acagaacttt gcggacagta gcgaaatcac    2280
gacctttgtc ccacacgatc tcacccgttt cgccgttggt ttcgatcaga gggcgtttac    2340
gaatttcgcc attcgctaag gtgatttcgg ttttgaagaa attcataatg tttgagtaga    2400
aaagtatttt agcggttgct ttgccaattt cctgttcaga tttggcgatc attttgcgca    2460
cgtcgtaaac tttataatcg ccgtacacaa attcgctttc cagtttcgga tattttttga   2520
tcagtgccgt gccaacaact gcattcgata tgcgtcgtg cgcgtggtga tagttgttaa    2580
tctcgcgcac tttatagaat tggaaatctt tacggaagtc ggaaaccagc ttagatttca   2640
gggtaataac cttaacttcg cggatcagtt tgtcattttc atcgtattta tgttcatac    2700 gagagtccag aatctgagca acatgtttg taatctggcg agtttctacc agttgacgtt    2760 taataaaaacc cgccttatcc agctcagaca aaccgccacg ttcagctttg gtcaggttat   2820
caaatttacg ttgagtaatc agtttcgcgt taagcagttg acgccaatag ttcttcattt    2880
tcttaactac ttcttccgat ggaacgttgt cactcttccc acggttttta tcgctacggg    2940
tgagtacttt gttatcaatg aatcatctt tcagaaaaga ctgcggaaca atgtggtcaa    3000
cgtcgtaatc ggagaggcgg ttgatgtcca gctcctgatc tacatacatg tcacgaccat   3060
tttgcaggta gtacaggtac agtttttcat tttgcagttg ggtattttca acagggtgtt    3120
ctttcagaat ctgagagcca agttctttaa tacctcctc gatacgtttc atgcgttcgc    3180
gggagttttt ctgtcccttc tgggtcgttt ggttttcacg agccatctcg ataacaatgt    3240
tttccggttt gtgacgaccc ataactttca caagctcatc caccactttc acggtttgca    3300 ggatacctttt tttgatcgcc ggactacctg ctaaattggc gatatgctcg tgcagagaat   3360
caccttgacc agaaacctga gctttctgga tgtcctcttt gaaggtcagg gaatcgtcgt    3420
gaatcagttg catgaagtta cggtttgcga agccgtcaga tttcaggaag tccagaatag   3480
ttttaccgga ctgtttgtca cggataccgt taatcagttt acggctcaga cggccccagc    3540
cagtataacg gcgacgtttc agttgtttca ttactttatc gtcaaacagg tgagcatacg    3600
tcttcaagcg ttcttcaatc atttcacgat cttcgaacag agtcagggtc aggacgatgt    3660
cctctaagat gtcctcattt tcttcgttgt ccaagaaatc tttgtcttta atgatctta     3720 ataaatcgtg atacgtgcct aaacttgcat taaaacgatc ttcaactcca ctaatctcga    3780
cggagtcgaa gcattcgatt ttcttgaagt agtcctcttt cagctgttta acggttactt     3840
tacggttggt tttaaacagt aaatcaacaa ttgctttttt ctgttcaccg ctcaggaatg    3900
caggtttacg catgccctca gtcacatact ttactttagt cagctcgttg tacacggtga    3960
agtattcgta cagaagggag tgtttcggca gtaccttttc gttcggcagg ttttttatcaa   4020
```

```
agttagtcat gcgctcgatg aaggattggg cgcttgcgcc tttgtcaacc acttcctcga    4080
agttccacgg ggtaatagtt tcttcggatt tgcgagtcat ccacgcgaaa cgggagttgc    4140
cacgcgccag cgggccgaca taatacggga tacgaaaggt caggattttt tcgattttt    4200 cacgattatc tttcaggaac gggtaaaaat cctcttggcg acgcaggata gcgtgcagtt    4260
cacctaagtg gatctggtgc ggaatgctac cgttgtcgaa ggtacgctgt ttacgaagca    4320
gatcctcacg attcagttta acaagtaatt cttccgtgcc atccattttt tctaagattg    4380
gcttgatgaa tttgtagaac tcctcttggc ttgcacccc gtcaatataa cccgcgtagc    4440 cgttttgga ttggtcaaag aagatctcct tgtacttctc cggcagttgt tgccgtacca    4500
gcgctttcag aagagtcaga tcttggtgat gttcgtcata gcgtttaatc atggatgcag    4560
aaagcggtgc tttggtgatt tcggtattca cacgaagaat atcagacagg agaatagcgt    4620
ctgataagtt ctttgccgcc agaaacagat cagcgtactg atctccgatc tgggccagta    4680
agttatccaa gtcatcgtca tacgtatctt tgctaagttg aagttttgcg tcctctgcca    4740
gatcgaagtt gcttttgaag ttcggggtca gtcccaagct aagagcgatc agattgccga    4800
acagtccgtt tttcttctca cccggcagtt gcgcaattaa gttttccaga cgacgggatt    4860
tggacaggcg tgcggacaag atcgctttcg cgtcaacacc gctagcatta attgggtttt    4920
cttcaaacag ctggttatag gtttgcacca gctggatgaa cagtttgtct acatcgctgt    4980
tgtctggatt caggtcgcct tcgatcagga aatgaccacg gaacttaatc atatgcgcta    5040
aggccagata gatcagacgc agatcggcct tatccgtcga atcgaccagc ttttgcgca    5100 ggtgatagat agtcgggtat ttttcgtgat acgctacttc gtccacaatg ttgccgaaga    5160
ttggatgacg ttcgtgcttt ttatcttctt ccaccagaaa tgattcttcc agacggtgaa    5220
aaaagctgtc atctactta gccatttcgt tagagaagat ttcttgcagg tagcagatgc    5280 ggttttacg acgggtgtaa cggcgacgag cggtgcgttt cagacgtgtt gcttctgcgg    5340
tttcgccgga atcgaacaga agcgcaccga ttaagttctt tttgatacta tggcgatctg    5400
tattacccag taccttgaac ttttagacg gaactttata ttcatcagtg atcaccgccc    5460
atccgacgct atttgtgccg atgtctaagc ctatgctgta tttcttatcc atagaaactt    5520
tctccttttt aagctccagt aaccttaacg atacggtacg tttcgtatca tgtcaattgg    5580
taacgaatca gattcagtac gtcgcgtgct acatttgaag agataaattg cactgaaatc    5640
tagaaatatt ttatctgatt aataagatga tcttcttgag atcgttttgg tctgcgcgta    5700
atctcttgct ctgaaaacga aaaaccgcc ttgcagggcg gttttcgaa ggttctctga    5760 gctaccaact ctttgaaccg aggtaactgg cttggaggag cgcagtcgcc aaaacttgtc    5820 cttcagttt agccttatcc ggcgcatgac ttcaagacta actcctctaa atcaattacc    5880
agtggctgct gccagtggtg cttttgcatg tctttccggg ttggactcaa gacgatagtt    5940
accggataag gcgcagcggt cggactgaac ggggggttcg tgcatacagt ccagcttgga    6000
gcgaactgcc tacccggaac tgagtgtcag gcgtggaatg agacaaacgc ggccataaca    6060
gcggaatgac accggtaaac cgaaaggcag gaacaggaga gcgcacgagg gagccgccag    6120
ggggaaacgc ctggtatctt tatagtcctg tcaggtttcg ccaccactga tttgagcgtc    6180
agatttcgtg atgcttgtca gggggcgga gcctatggaa aaacggcttt gccgcggccc    6240
tctcacttcc ctgttaagta tcttcctggc atcttccagg aaatctccgc ccgttcgta    6300 agccatttcc gctcgccgca gtcgaacgac cgagcgtagc gagtcagtga gcgaggaagc    6360
```

-continued

| | |
|---|---|
| ggaatatatc ctgtatcaca tattctgctg acgcaccggt gcagccttt ttctcctgcc | 6420 |
| acatgaagca cttcacttac accctcatca gtgccaacat agtaagccag tatacactcc | 6480 |
| gctagcgctg atgtccggcg gtgc | 6504 |

<210> SEQ ID NO 5
<211> LENGTH: 4024
<212> TYPE: DNA
<213> ORGANISM: Artificial Sequence
<220> FEATURE:
<223> OTHER INFORMATION: plasmid encoding the PhlF repressor protein

<400> SEQUENCE: 5

| | |
|---|---|
| agcgatcgcg tatttcgtct cgctcaggcg caatcacgaa tgaataacgg tttggttgat | 60 |
| gcgagtgatt ttgatgacga gcgtaatggc tggcctgttg aacaagtctg gaaagaaatg | 120 |
| cataagcttt tgccattctc accggattca gtcgtcactc atggtgattt ctcacttgat | 180 |
| aaccttattt ttgacgaggg gaaattaata ggttgtattg atgttggacg agtcggaatc | 240 |
| gcagaccgat accaggatct tgccatccta tggaactgcc tcggtgagtt ttctccttca | 300 |
| ttacagaaac ggcttttca aaaatatggt attgataatc ctgatatgaa taaattgcag | 360 |
| tttcatttga tgctcgatga gttttttcaa atcagaattg gttaattggt tgtggaaacg | 420 |
| taactgtcag accaagttta ctcatatata ctttagattg atttaaaact tcatttttaa | 480 |
| tttaaaagga tctaggtgaa gatccttttt gataatctca tgaccaaaat cccttaacgt | 540 |
| gagttttcgt tccactgagc gtcagacccc gttgatgata ccgctgcctt actgggtgca | 600 |
| ttagccagtc tgaatgacct gtcacggat aatccgaagt ggtcagactg aaaatcaga | 660 |
| gggcaggaac tgctgaacag caaaaagtca gatagcacca catagcagac cgccataaa | 720 |
| acgccctgag aagcccgtga cgggcttttc ttgtattatg ggtagtttcc ttgcatgaat | 780 |
| ccataaaagg cgcctgtagt gccatttacc cccattcact gccagagccg tgagctgacc | 840 |
| aaaacgaaaa aagacgctcg aaagcgtctg ttttctggaa tttggtagcg attatggcct | 900 |
| agttaacgct gagtacccgg acaaacacca ttaatcagaa ggaaggtaaa ttcttcaata | 960 |
| tcctgttcaa cggtcagctg ttcggttaac aggcgatacc aacaaaaacc aaaaatcata | 1020 |
| tccagaagaa gttcacgatt ggtatctttc ggcagttcac cattgctaat ggcattttca | 1080 |
| accagttttt tcggcatctc acgacgacgt tccataaatt gatcctttaa ctgggtcagg | 1140 |
| gttgcaggat ccagctgagc ttctgcaata acacaacgaa atgcttcacc gcaaatagtt | 1200 |
| tcacgccaaa ctttccataa attacgcagt aaaaaatcca gatctgcttt aaagctaccc | 1260 |
| agatccggaa atttacgcac ctgttcgctt tcatttcat acacttcggc aatcagtgct | 1320 |
| gctttattcg tccaccaacg ataaatggtc ggtttgcttg ctccggcacg acgtgcaacg | 1380 |
| cttcaatgc tcagtccgct ataaccacat tctttcagga tctcgatggt actggtcaga | 1440 |
| attgctttat gggtatgcgg actacgcagg ctaccaatgc tactacgtga cggggtacgt | 1500 |
| gccatagtac ctttctcctc tttaatgatt cgctagcatt gtacctagga ctgagctagc | 1560 |
| cgtaaaatcg tgctacattt gaagagataa attgcactga atctagaaa tattttatct | 1620 |
| gattaataag atgatcttct tgagatcgtt ttggtctgcg gtcatctgcg tgaccgccta | 1680 |
| cggcggctgc ggcgccctac gggcttgctc tccgggcttc gccctgcgcg tcgctgcgc | 1740 |
| tcccttgcca gcccgtggat atgtggacga tggccgcgag cggccaccgg ctggctcgct | 1800 |
| tcgctcggcc cgtggacaac cctgctggac aagctgatgg acaggctgcg cctgcccacg | 1860 |
| agcttgacca cagggattgc ccaccggcta cccagccttc gaccacatac ccaccggctc | 1920 |

-continued

```
caactgcgcg gcctgcggcc ttgccccatc aatttttta atttctctg gggaaaagcc    1980
tccggcctgc ggcctgcgcg cttcgcttgc cggttggaca ccaagtggaa ggcgggtcaa    2040
ggctcgcgca gcgaccgcgc agcggcttgg ccttgacgcg cctggaacga cccaagccta    2100
tgcgagtggg ggcagtcgaa gggcgaagcc cgcccgcctg cccccgagc ctcacggcgg    2160
cgagtgcggg ggttccaagg gggcagcgcc accttgggca aggccgaagg ccgcgcagtc    2220
gatcaacaag ccccggaggg gccacttttt gccggagggg gagccgcgcc gaaggcgtgg    2280
gggaaccccg caggggtgcc cttctttggg caccaaagaa ctagatatag gcgaaatgc    2340
gaaagactta aaaatcaaca acttaaaaaa gggggtacg caacagctca ttgcggcacc    2400
ccccgcaata gctcattgcg taggttaaag aaaatctgta attgactgcc acttttacgc    2460
aacgcataat tgttgtcgcg ctgccgaaaa gttgcagctg attgcgcatg gtgccgcaac    2520
cgtgcggcac ccctaccgca tggagataag catggccacg cagtccagag aaatcggcat    2580
tcaagccaag aacaagcccg gtcactgggt gcaaacggaa cgcaaagcgc atgaggcgtg    2640
ggccgggctt attgcgagga agcccacggc ggcaatgctg ctgcatcacc tcgtggcgca    2700
gatgggccac cagaacgccg tggtggtcag ccagaaaaca cttccaagc tcatcggacg    2760
ttctttgcgg acggtccaat acgcagtcaa ggacttggtg gccgagcgct ggatctccgt    2820
cgtgaagctc aacggccccg gcaccgtgtt ggcctacgtg gtcaatgacc gcgtggcgtg    2880
gggccagccc cgcgaccagt tgcgcctgtc ggtgttcagt gccgccgtgg tggttgatca    2940
cgacgaccag gacgaatcgc tgttggggca tggcgacctg cgccgcatcc cgaccctgta    3000
tccgggcgag cagcaactac cgaccggccc cggcgaggag ccgcccagcc agcccggcat    3060
tccgggcatg gaaccagacc tgccagcctt gaccgaaacg gaggaatggg aacggcgcgg    3120
gcagcagcgc ctgccgatgc ccgatgagcc gtgttttctg gacgatggcg agccgttgga    3180
gccgccgaca cgggtcacgc tgccgcgccg gtagcacttg ggttgcgcag caacccgtaa    3240
gtgcgctgtt ccagactatc ggctgtagcc gcctcgccgc cctataccT gtctgcctcc    3300
ccgcgttgcg tcgcggtgca tggagccggg ccacctcgac ctgaatgaa gccggcggca    3360
cctcgctaac ggattcaccg ttactgcacg gcgttcggct gcggcgagcg gtatcagctc    3420
actcaaaggc ggtaatacgg ttatccacag aatcagggga taacgcaggc ctccgaaatc    3480
ctgcagggaa agcacgttg tgtctcaaaa tctctgatgt tacattgcac aagataaaaa    3540
tatatcatca tgaacaataa aactgtctgc ttacataaac agtaatacaa ggggtgttat    3600
gagccatatt caacgggaaa cgtcttgctc gaggccgcga ttaaattcca acatggatgc    3660
tgatttatat gggtataaat gggctcgcga taatgtcggg caatcaggtg cgacaatcta    3720
tcgattgtat gggaagcccg atgcgccaga gttgtttctg aaacatggca aaggtagcgt    3780
tgccaatgat gttacagatg agatggtcag actaaactgg ctgacggaat ttatgcctct    3840
tccgaccatc aagcattta tccgtactcc tgatgatgca tggttactca ccactgcgat    3900
ccccgggaaa acagcattcc aggtattaga agaatatcct gattcaggtg aaaatattgt    3960
tgatgcgctg gcagtgttcc tgcgccggtt gcattcgatt cctgtttgta attgtccttt    4020
taac                                                                 4024
```

<210> SEQ ID NO 6
<211> LENGTH: 213
<212> TYPE: PRT
<213> ORGANISM: Artificial Sequence
<220> FEATURE:

<223> OTHER INFORMATION: SrpR repressor protein

<400> SEQUENCE: 6

Met Ala Arg Lys Thr Ala Ala Glu Ala Glu Glu Thr Arg Gln Arg Ile
1               5                   10                  15

Ile Asp Ala Ala Leu Glu Val Phe Val Ala Gln Gly Val Ser Asp Ala
            20                  25                  30

Thr Leu Asp Gln Ile Ala Arg Lys Ala Gly Val Thr Arg Gly Ala Val
        35                  40                  45

Tyr Trp His Phe Asn Gly Lys Leu Glu Val Leu Gln Ala Val Leu Ala
    50                  55                  60

Ser Arg Gln His Pro Leu Glu Leu Asp Phe Thr Pro Asp Leu Gly Ile
65                  70                  75                  80

Glu Arg Ser Trp Glu Ala Val Val Val Ala Met Leu Asp Ala Val His
                85                  90                  95

Ser Pro Gln Ser Lys Gln Phe Ser Glu Ile Leu Ile Tyr Gln Gly Leu
            100                 105                 110

Asp Glu Ser Gly Leu Ile His Asn Arg Met Val Gln Ala Ser Asp Arg
        115                 120                 125

Phe Leu Gln Tyr Ile His Gln Val Leu Arg His Ala Val Thr Gln Gly
    130                 135                 140

Glu Leu Pro Ile Asn Leu Asp Leu Gln Thr Ser Ile Gly Val Phe Lys
145                 150                 155                 160

Gly Leu Ile Thr Gly Leu Leu Tyr Glu Gly Leu Arg Ser Lys Asp Gln
                165                 170                 175

Gln Ala Gln Ile Ile Lys Val Ala Leu Gly Ser Phe Trp Ala Leu Leu
            180                 185                 190

Arg Glu Pro Pro Arg Phe Leu Leu Cys Glu Glu Ala Gln Ile Lys Gln
        195                 200                 205

Val Lys Ser Phe Glu
    210

<210> SEQ ID NO 7
<211> LENGTH: 639
<212> TYPE: DNA
<213> ORGANISM: Artificial Sequence
<220> FEATURE:
<223> OTHER INFORMATION: DNA sequence encoding SrpR repressor protein

<400> SEQUENCE: 7
atggcacgta aaaccgcagc agaagcagaa gaaacccgtc agcgtattat tgatgcagca      60
ctggaagttt ttgttgcaca gggtgttagt gatgcaaccc tggatcagat tgcacgtaaa     120
gccggtgtta cccgtggtgc agtttattgg cattttaatg gtaaactgga agttctgcag     180
gcagttctgg caagccgtca gcatccgctg gaactggatt ttacaccgga tctgggtatt     240
gaacgtagct gggaagcagt tgttgttgca atgctggatg cagttcatag tccgcagagc     300
aaacagttta gcgaaattct gatttatcag ggtctggatg aaagcggtct gattcataat     360
cgtatggttc aggcaagcga tcgttttctg cagtatattc atcaggttct gcgtcatgca     420
gttacccagg gtgaactgcc gattaatctg gatctgcaga ccagcattgg tgttttttaaa     480 ggtctgatta ccggtctgct gtatgaaggt ctgcgtagca agatcagca ggcacagatt      540 atcaaagttg cactgggtag cttttgggca ctgctgcgtg aaccgcctcg ttttctgctg     600
tgtgaagaag cacagattaa acaggtgaaa tccttcgaa                            639

```
<210> SEQ ID NO 8
<211> LENGTH: 67
<212> TYPE: DNA
<213> ORGANISM: Artificial Sequence
<220> FEATURE:
<223> OTHER INFORMATION: SrpR promoter-operator sequence

<400> SEQUENCE: 8
gattcgttac caattgacag ctagctcagt cctaggtata tacatacatg cttgtttgtt    60
tgtaaac                                                              67

<210> SEQ ID NO 9
<211> LENGTH: 7393
<212> TYPE: DNA
<213> ORGANISM: Artificial Sequence
<220> FEATURE:
<223> OTHER INFORMATION: Plasmid p455 containing the Cpf1 nuclease under
      the control of the PsrpR promoter, a crRNA targeting LacZ and a
      Lambda phage cos signal

<400> SEQUENCE: 9
gacagctttg aattgtttta ggggcgttat tcgagggcaa tcggagctaa cttcaagact    60
acttctttgt tgaatactaa atagtgcaaa ggtcgtgttt cctcaaggat actccgctaa   120
caatatagga ttccaatcag attcagcact ggcggtacgg gtgttgcggt gaggcgttcg   180
ggtttacggc tcgaagctag cacggtagga agcctgacaa tcaccaagca aaagggccgt   240
cgaaggccca aagatacga aagctctcga agccttatcc ttgaccgatc cacctattta   300
ggcagttacg cacaaaagct acccaataat ccgtgacagg cacaatatca cggaacaaaa   360
ccgaaaactc tcgtacacgg ttaggttttc gctaggaaga ataaacctct atcttgatta   420
taagaaggct ccccaagcac ccccaaaacc gaaatagcgg tttgcaataa gggacaagtt   480
acgagtgtag acacgcagaa ttatccagcc tttagtcttt aggaaggcaa agctattgta   540
cgcggtagcc gtcgtagcaa tttaccaact gtagaattat tggacacacg taggaagggc   600
ttacagttga agtttaataa ggtcacacgc aaaaccgcta aggaataatc gcaccgttag   660
cgaaagaata tttcagagcg gttagtaaag gttgagtaaa gtgagattcc aaagtgagcc   720
tttataaaaa gtaaagagct ataataaaac cgtcgagcag aaaacaatcg cctgaaatct   780
caagcacgtt gcccttttcta acgtcgctaa ggtttcgtaa acccgtttga ttaggaagaa   840
gaataagtaa cccgattagg tttgagatcg cgggttatcg gtttggatta aaagtggata   900
ccagcggagt caacgccgac gcaaacgtac agtgatccaa tcctgttgca cggtcaagca   960
caatcagctc gcaagatctt ggaatagtgt gcccaacagt ttagttgagg gccacgttcc  1020
gactacaagt tgcttcaaga ggggaatttg gatttggcgg caaaagcacc gccggacatc  1080
agcgctagcg gagtgtatac tggcttacta tgttggcact gatgagggtg taagtgaagt  1140
gcttcatgtg gcaggagaaa aaaggctgca ccggtgcgtc agcagaatat gtgatacagg  1200
atatattccg cttcctcgct cactgactcg ctacgctcgg tcgttcgact gcggcgagcg  1260
gaaatggctt acgaacgggg cggagatttc ctggaagatg ccaggaagat acttaacagg  1320
gaagtgagag ggccgcggca aagccgtttt tccataggct ccgcccccct gacaagcatc  1380
acgaaatctg acgctcaaat cagtggtggc gaaacctgac aggactataa agataccagg  1440
cgtttccccc tggcggctcc ctcgtgcgct ctcctgttcc tgcctttcgg tttaccggtg  1500
tcattccgct gttatggccg cgtttgtctc attccacgcc tgacactcag ttccgggtag  1560
gcagttcgct ccaagctgga ctgtatgcac gaaccccccg ttcagtccga ccgctgcgcc  1620
```

```
ttatccggta actatcgtct tgagtccaac ccggaaagac atgcaaaagc accactggca    1680
gcagccactg gtaattgatt tagaggagtt agtcttgaag tcatgcgccg gataaggcta    1740
aactgaaagg acaagttttg gcgactgcgc tcctccaagc cagttacctc ggttcaaaga    1800
gttggtagct cagagaacct tcgaaaaacc gccctgcaag gcggtttttt cgttttcaga    1860
gcaagagatt acgcgcagac caaaacgatc tcaagaagat catcttatta atcagataaa    1920
atatttctag atttcagtgc aatttatctc ttcaaatgta gcacgcgacg tacggtggaa    1980
gattcgttac caattgacag ctagctcagt cctaggtata tacatacatg cttgtttgtt    2040
tgtaaactac tttcgagtac taacaaagct ggtttgaatg tccatctatc aggagtttgt    2100
taacaagtat tccctgtcta aaccctgcg ttttgaactg atcccgcagg gcaaaacttt    2160
ggaaaacatt aaagcgcgtg gcctgattct ggatgacgaa aaacgtgcaa aggattacaa    2220
gaaagctaaa cagatcatcg acaaatatca ccagttcttt atcgaagaaa ttctgtcgtc    2280
ggtgtgcatc agtgaggatc tgttacgaa ttattctgat gtatacttta aacttaaaaa    2340
gtccgatgac gataatctgc aaaaagattt caagtcagcc aaagatacca tcaagaaaca    2400
gatctcagaa tatattaaag atagcgaaaa gttcaaaaac ctgtttaacc aaaacctcat    2460
tgatgctaag aaaggccaag aatctgacct gatcttatgg ctgaaacaga gcaagataa    2520 cggcattgaa ctgttcaaag ctaatagcga catcaccgat attgatgaag cgctcgaaat    2580
catcaagtct ttcaaaggct ggacgacgta tttcaaaggt tttcatgaaa ccgtaagaa    2640 tgtatattcg agcaacgata ttccgacctc tattatttat cgtatcgtgg acgacaacct    2700
gccgaagttt ctggaaaaca aagcgaaata tgaatctctg aaagacaaag caccggaagc    2760
tattaactat gaacagatca agaaagatct ggcggaagaa ctgaccttcg acatcgacta    2820
taaaacctcc gaagttaacc agcgtgtttt ctcactggac gaggttttcg aaatcgctaa    2880
tttcaacaat tacctgaatc aatctggcat caccaaattc aacaccatta ttggtggcaa    2940
atttgttaac ggcgaaaaca ccaagcgtaa gggcatcaac gaatacatta acctgtatag    3000
ccaacaaatc aacgacaaaa ccctgaaaaa gtataaaatg tccgttctgt ttaaacagat    3060
tttatcggac accgaatcta aatccttcgt aattgataaa ctggaagatg atagcgacgt    3120
tgtcaccacg atgcagagct tttatgagca gattgcggcg ttcaaaaccg tggaagagaa    3180
atctattaaa gaaactctgt ccctgctctt tgacgacctc aaagcgcaga aactagatct    3240
gtctaagatt tactttaaaa acgacaaatc tctgaccgat ctcagtcaac aagttttcga    3300
tgactatagc gtgatcggca cggcagtttt ggaatacatc acccaacaaa tcgcgccgaa    3360
aaatctggac aacccgtcca agaaggaaca ggaactgatt gcaaagaaaa cagaaaaagc    3420
taaatacctg agcttagaaa ctatcaaact ggcacttgag gaatttaata acatcgtga    3480 tattgataaa cagtgtcgtt tgaggaaat tctggcgaac tttgcggcaa tcccgatgat    3540
cttcgacgaa attgctcaaa acaaagacaa tctggcgcag atctctatca agtaccagaa    3600
tcagggtaag aaagatctgc ttcaagcatc tgcgaggac gatgtgaaag caattaaaga    3660
cttattagat cagacgaata acttattaca caagctcaaa atcttccaca tcagccagag    3720
cgaggacaag gcgaacattc tggataaaga tgaacacttc tatctggtgt tcgaagaatg    3780
ttacttcgaa ctggcaaaca tcgtccctct ctacaataaa atccgcaact acatcacgca    3840
gaagccttac tctgacgaga aattcaaact gaacttcgaa aacagcacgc tggcgaacgg    3900
ctgggataag aacaaagagc cggacaacac cgcaatcctg ttcatcaaag acgacaaata    3960
ctatctgggc gtaatgaaca agaagaacaa caagatcttc gacgataaag cgatcaaaga    4020
```

```
aaacaagggt gaaggctata agaaaatcgt gtacaagctc ctgccgggtg cgaataaaat    4080
gttaccgaaa gtgttctttt ccgcgaaaag catcaaattc tacaacccgt ctgaggatat    4140
tctgcgcatc cgcaatcata gcacgcacac taaaaacggt agcccgcaga aagggtatga    4200
aaaattcgaa tttaatatag aggactgccg taagttcatc gacttctata acagagcat     4260 ttccaaacat ccggaatgga aagacttcgg cttccgtttc tctgacactc agcgctataa    4320
tagcatcgac gagttctacc gcgaagtgga gaatcagggc tataaactga ccttcgagaa    4380
cattagtgag tcgtacatcg actccgttgt gaatcagggt aaactgtacc tgtttcagat    4440
ctataataaa gactttagcg cgtacagcaa aggccgtccg aatctgcaca ccctttactg    4500
gaaagcatta tttgacgaac gtaacctgca agatgtggtg tataaactga acggtgaggc    4560
ggaacttttc taccgtaaac agagtatccc gaagaaaatc acgcatccgg caaagaagc     4620 tattgccaac aaaaacaaag acaacccgaa gaaagaatca gtattcgaat atgacctgat    4680
caaagataaa cgtttcaccg aagataagtt ctttttccac tgtccgatta ccatcaactt    4740
caaatctagc ggtgcgaaca gttcaacga tgaaattaac ttattactga agagaaagc     4800 taatgacgta cacatcttat ctattgatcg cggtgaacgt catttagcat actatacact    4860
ggtagatggt aaaggtaata ttattaaaca ggatactttc aatattatcg gtaatgaccg    4920
tatgaaaacc aactatcacg ataagctggc ggcgatcgaa aaagatcgtg attctgcgcg    4980
taaagattgg aagaaaatta acaatatcaa agaaatgaaa gaaggctatc tgagccaagt    5040
ggtgcacgag atcgcaaaac tggtgattga atataacgct atcgtggttt tcgaagatct    5100
gaactttggt tttaaacgtg gtcgcttcaa agtagaaaaa caggtgtacc aaaaactgga    5160
aaaaatgctg attgaaaaac tgaactatct ggtttttaaa gacaacgaat tgacaaaac     5220 gggtggcgta ctccgtgcct atcagctgac cgctccgttc gaaacgttca gaaaatggg     5280 taaacaaacg gggattatct attatgtgcc agctggtttc acctccaaga tttgtccagt    5340
tacgggcttc gttaaccagc tgtacccgaa atacgagagc gttagcaaat ctcaagaatt    5400
tttcagcaaa ttcgcaagaa tctgctataa tctggataaa ggctatttcg agttcagctt    5460
cgattacaaa aacttcggcg ataaagcggc taaaggtaag tggactattg ctagctttgg    5520
tagccgtctg attaactttc gcaactccga caaaaaccat aattgggaca cgcgtgaagt    5580
gtatccgacc aaagaactgg aaaaattact gaaagactat tccatcgaat atggtcatgg    5640
ggagtgcatt aaagcggcga tttgcggtga atccgataag aaattttttcg ccaaactgac    5700 cagcgtgctt aacaccattc tgcaaatgcg taattctaaa acgggtacgg agctggacta    5760
cctgatttct ccggtagccg acgttaacgg caacttcttc gattctcgtc aagcaccgaa    5820
aaatatgcca caagacgcgg atgccaacgg tgcataccat atcggcttaa aaggcttaat    5880
gttattaggc cgtatcaaga ataatcagga gggcaagaaa ttaaatctgg ttatcaaaaa    5940
cgaagaatac ttcgagttcg ttcagaatcg taacaattaa tgtatgctta agcagctcgg    6000
taccaaagac gaacaataag acgctgaaaa gcgtcttttt tcgttttggt cctgttgcgg    6060
cgcgatagtg tgaacatgct atagacttct ggtgctaccc gactgacaat taatcatccg    6120
gctcgtataa tgctagcaat ttctactgtt gtagatgcca gctggcgtaa tagcgaagag    6180
tcgagacgaa caataaggcc tccctaacgg ggggccttt ttattgataa caaaagtaaa     6240
gccgaacgcc ccaaaaagcc tcgctttcag cacctgtcgt ttcctttctt ttcagagggt    6300
attttaaata aaaacattaa gttatgacga agaagaacgg aaacgcctta aaccggaaaa    6360
```

```
ttttcataaa tagcgaaaac ccgcgaggtc gccgccccgt aacctgtcgg atcaccggaa    6420
aggacccgta aagtgataat gattatcatc tacatatcac aacgtgcgta aagggactag    6480
tggattgcat acctttggtc gaaaaaaaaa gcccgcactg tcaggtgcgg cttttttca     6540 gtgtttcctt gccggattac gccccgccct gccactcatc gcagtattgt tgtaattcat    6600
taagcattct gccgacatgg aagccatcac aaacggcatg atgaacttgg atcgccagtg    6660
gcattaacac cttgtcgcct tgcgtataat attttcccat agtgaaaacg ggggcgaaga    6720
agttgtccat atttgctacg tttaaatcaa aactggtgaa actcacccac ggattggcac    6780
tgacgaaaaa catattttcg ataaacccct tagggaaata tgctaagttt tcaccgtaac    6840
acgccacatc ttgactatat atgtgtagaa actgccggaa atcgtcgtgg tattctgacc    6900
agagcgatga aaacgtttca gtttgctcat ggaaaacggt gtaacaaggg tgaacactat    6960
cccatatcac cagctcaccg tctttcattg ccatacgaaa ctccggatgt gcattcatca    7020
ggcgggcaag aatgtgaata aaggccggat aaaacttgtg cttatttttc tttacggttt    7080
ttaaaaaggc cgtaatatcc agctgaacgg tttggttata ggtgcactga gcaactgact    7140
ggaatgcctc aaaatgttct ttacgatgcc attgacttat atcaactgta gtatatccag    7200
tgattttttt ctccatttta gcttccttag cttgcgaaat ctcgataact caaaaaatag    7260
tagtgatctt atttcattat ggtgaaagtt gtcttacgtg caacattttc gcaaaaagtt    7320
ggcgctttat caacactgtc cctcctgttc agctactgac ggtactgcgg aactgactaa    7380
agtagtgcgt aac                                                      7393
```

<210> SEQ ID NO 10
<211> LENGTH: 5119
<212> TYPE: DNA
<213> ORGANISM: Artificial Sequence
<220> FEATURE:
<223> OTHER INFORMATION: plasmid encoding the SrpR repressor protein

<400> SEQUENCE: 10

```
gtaaaccagc aatagacata agcggctatt aacgaccct gccctgaacc gacgaccggg      60
tcatcgtggc cggatcttgc ggcccctcgg cttgaacgaa ttgttagaca ttatttgccg    120
actaccttgg tgatctcgcc tttcacgtag tggacaaatt cttccaactg atctgcgcgc    180
gaggccaagc gatcttcttc ttgtccaaga taagcctgtc tagcttcaag tatgacgggc    240
tgatactggg ccggcaggcg ctccattgcc cagtcggcag cgacatcctt cggcgcgatt    300
ttgccggtta ctgcgctgta ccaaatgcgg gacaacgtaa gcactacatt tcgctcatcg    360
ccagcccagt cgggcggcga gttccatagc gttaaggttt catttagcgc ctcaaataga    420
tcctgttcag gaaccggatc aaaagagttcc tccgccgctg gacctaccaa ggcaacgcta    480
tgttctcttg cttttgtcag caagatagcc agatcaatgt cgatcgtggc tggctcgaag    540
atacctgcaa gaatgtcatt gcgctgccat tctccaaatt gcagttcgcg cttagctgga    600
taacgccacg gaatgatgtc gtcgtgcaca acaatggtga cttctacagc gcggagaatc    660
tcgctctctc caggggaagc cgaagtttcc aaaaggtcgt tgatcaaagc tcgccgcgtt    720
gtttcatcaa gccttacggt caccgtaacc agcaaatcaa tatcactgtg tggcttcagg    780
ccgccatcca ctgcggagcc gtacaaatgt acggccagca acgtcggttc gagatggcgc    840
tcgatgacgc caactacctc tgatagttga gtcgatactt cggcgatcac cgcttccctc    900
atctagtagg tttcctgtgt gactctagta ttattcgaag gatttcacct gtttaatctg    960
tgcttcttca cacagcagaa aacgaggcgg ttcacgcagc agtgcccaaa agctacccag   1020
```

| | | | | | |
|---|---|---|---|---|---|
| tgcaactttg | ataatctgtg | cctgctgatc | tttgctacgc | agaccttcat | acagcagacc | 1080
| ggtaatcaga | cctttaaaaa | caccaatgct | ggtctgcaga | tccagattaa | tcggcagttc | 1140
| accctgggta | actgcatgac | gcagaacctg | atgaatatac | tgcagaaaac | gatcgcttgc | 1200
| ctgaaccata | cgattatgaa | tcagaccgct | ttcatccaga | ccctgataaa | tcagaatttc | 1260
| gctaaactgt | tgctctgcg | gactatgaac | tgcatccagc | attgcaacaa | caactgcttc | 1320
| ccagctacgt | tcaatacccca | gatccggtgt | aaaatccagt | tccagcggat | gctgacggct | 1380
| tgccagaact | gcctgcagaa | cttccagttt | accattaaaa | tgccaataaa | ctgcaccacg | 1440
| ggtaacaccg | gctttacgtg | caatctgatc | cagggttgca | tcactaacac | cctgtgcaac | 1500
| aaaaacttcc | agtgctgcat | caataatacg | ctgacgggtt | tcttctgctt | ctgctgcggt | 1560
| tttacgtgcc | atactcttcc | ttttcaata | ttattgaagc | atttatcagg | gttattgtct | 1620
| catgagcgga | tacatatttg | aatgtattta | gaaaaataaa | caaatagcta | gctcactcgg | 1680
| tcgctacgct | ccgggcgtga | gactgcggcg | ggcgctgcgg | acacatacaa | agttacccac | 1740
| agattccgtg | gataagcagg | ggactaacat | gtgaggcaaa | acagcagggc | cgcgccggtg | 1800
| gcgttttttcc | ataggctccg | ccctcctgcc | agagttcaca | taaacagacg | cttttccggt | 1860
| gcatctgtgg | gagccgtgag | gctcaaccat | gaatctgaca | gtacgggcga | aacccgacag | 1920
| gacttaaaga | tccccaccgt | ttccggcggg | tcgctccctc | ttgcgctctc | ctgttccgac | 1980
| cctgccgttt | accggatacc | tgttccgcct | ttctccctta | cgggaagtgt | ggcgctttct | 2040
| catagctcac | acactggtat | ctcggctcgg | tgtaggtcgt | tcgctccaag | ctgggctgta | 2100
| agcaagaact | ccccgttcag | cccgactgct | gcgccttatc | cggtaactgt | tcacttgagt | 2160
| ccaacccgga | aaagcacggt | aaaacgccac | tggcagcagc | cattggtaac | tgggagttcg | 2220
| cagaggattt | gtttagctaa | acacgcggtt | gctcttgaag | tgtgcgccaa | agtccggcta | 2280
| cactggaagg | acagatttgg | ttgctgtgct | ctgcgaaagc | cagttaccac | ggttaagcag | 2340
| ttccccaact | gacttaacct | tcgatcaaac | cacctcccca | ggtggttttt | tcgtttacag | 2400
| ggcaaaagat | tacgcgcaga | aaaaaaggat | ctcaagaaga | tcctttgatc | actcttcctt | 2460
| tttcaatatt | attgaacctg | aggtctgttt | atcgaattaa | ttgcagatat | aaaaaaacca | 2520
| accgtaaggg | ttggtttttt | cttgggattt | ttggtcggca | cgagaggatt | tgaacctccg | 2580
| accccccgaca | ccccatgacg | gtgcgctacc | aggctgcgct | acgtgccgac | tcgtggctgc | 2640
| taatactacc | gttttccaca | ccgattgcaa | gtaagatatt | tcgctaactg | atttataatt | 2700
| aatcagttag | cgataaaacg | cttctcgtac | aacgctttct | ggtgaatggt | gcgggaggcg | 2760
| agacttgaac | tcgcacacct | tgcggcgcca | gaacctaaat | ctggtgcgtc | taccaatttc | 2820
| gccactcccg | caaaaaaga | tggtggctac | gacgggattc | gaacctgtga | ccccatcatt | 2880
| atgagtgatg | tgctctaacc | aactgagcta | cgtagccatc | ttttttttcg | cgataccctta | 2940
| tcggcgttgc | ggggcgcatt | atgcgtatag | agccttgcag | cgtcaacctc | tttttcaagg | 3000
| aaaattgctc | gaaagtgact | gtttggttag | gttgcgaaca | gcgaaccatg | acgaactgta | 3060
| aatctacgga | atgcttgata | ttcagggat | ttttgcggac | tggtacggat | gggagcgaac | 3120
| tgataaatgg | tgtccctgc | aggaatcgaa | cctgcaatta | gcccttagga | ggggctcgtt | 3180
| atatccatt | aactaagagg | acaatgcggc | atgagtatac | ccgctaatgg | agtgcgggt | 3240
| aagtacgttg | ccgctcgatt | gcttaaaccc | tcgccatta | tgccgggttt | ttataatttt | 3300
| tcttaatgtt | ttccgcacgt | tctgcttttt | ggacgtcatc | gattgtccct | ctaagacacg | 3360

```
gataaatcgg tgatatcacc acatcaacca ggcaacatgc ccgacttgtt gaatgcaata    3420
aacagaagga aaaacaggg aggagaaaag aagtggtgct gataggcaga ttcgaactgc     3480
cgacctcacc cttaccaagg gtgcgctcta ccaactgagc tatatcagca catcttggag    3540
cgggcagcgg gaatcgaacc cgcatcatca gcttggaagg ctgaggtaat agccattata   3600
cgatgcccgc atcctggaac tcggctacct gatttcatt ctgcactgaa tatcgagaga    3660
agctctcttt attcgagccg gtaagcgaac ttatcgtctc gggctacgcc atcgcgtggc   3720
cgaaattggt ggtgggggaa ggattcgaac cttcgaagtc tgtgacggca gatttacagt   3780
ctgctccctt tggccgctcg ggaacccac cggacttgat ggtgccgact accggaatcg    3840
aactggtgac ctactgatta caagtcagtt gctctaccta ctgagccaag tcggcatcaa   3900
gtagcgcgca ctctatggag acatgcgagt tcatgcaact aaaaaattgc ataatttgtt   3960
ttattggtca cattttatgc gacacgatga agaaacagcc taggtacctc atgagcccga   4020
agtggcgagc ccgatcttcc ccatcggtga tgtcggcgat ataggcgcca gcaaccgcac   4080
ctgtggcgcc ggtgatgccg gccacgatgc gtccggcgta gaggatccgt cacataccaa   4140
ggcggctaag cgagcagatg gaacatcaac gcctgcggtc aggaagatgc gcatcgacag   4200
caagacatca tggctatcag cttgtcgtcg tgcaggaatt gaagatttcc gtttccatga   4260
cctcagacac acctgggcaa gctggctgat tcagtcaggc gtcccattat cagtgcttca   4320
ggaaatgggc ggatgggagt ccatagaaat ggttcgtagg tatgctcacc ttgcgcctaa   4380
tcatttgaca gagcatgcga ggaaaataga cgacattttt ggtgataatg tcccaaatat   4440
gtcccactct gaaattatgg aggatataaa gaaggcgtaa ctgattgaat tgtaatggcg   4500
cgccctgcag gattcgaacc tgcggcccac gacttagaag gtcgttgctc tatccaactg   4560
agctaagggc gcgttgatac cgcaatgcgg tgtaatcgcg tgaattatac ggtcaaccct   4620
tgctgagtca atggctttg atctggttgc tgaacaagtg aacgaccgcg tctgattttc    4680
tgatttattt cgctatagcg gcaaacaaac gcacaccgct gcgcgtctga atcaagaaaa   4740 cccgtattt catgtatcaa agtgacctgc agccaagctt ggattgcgac acggagttac   4800
tttataatcc aatcgattgg ccccttagct cagtggttag agcaggcgac tcataatcgc   4860
ttggtcgctg cttcaagtcc agcaggggcc accagcggcc gcaaaggctg acgagaaatc   4920
gtcagccttt ttaagcttta agccgaattc agcacactg gcggccgtta ctagtggatc    4980
cgagctcggt accaagctta tcgatgataa gctgtcaaac atgagaatta caacttatat   5040 cgtatgggc tgacttcagc tgaaacctca ggcatttgag aagcacacgg tcacactgct    5100
tccggtagtc aataaaccg                                                5119
```

<210> SEQ ID NO 11
<211> LENGTH: 12335
<212> TYPE: DNA
<213> ORGANISM: Artificial Sequence
<220> FEATURE:
<223> OTHER INFORMATION: Plasmid comprising the PsrpR-Cpf1-LacZ circuit

<400> SEQUENCE: 11

```
ctaatctctt gccccgccc gtaatagcct ccaagagatt gaagatagta aagggcaaga      60
gctgattcgg cgttgaagga tagcggactt tcggtcaacc acaattcccc actcgacaaa    120
accagccgtg cgaataactc tgaaagtaca agcaacccaa gagggctgag cctaaactca    180
gctaattcct aagtgagcta aagactcgaa gtgacagctc ttaataaata gagcgggaac    240
gtcgaacggt cgtgaaagta atagtacaac gggtattaac ttactgagga tattgcttga    300
```

```
agctgtaccg tttttattggg tgaacgaata agatccagca attcagccaa agaagctacc    360
aatttttagt ttaagagtgt cacgtctgac ctcgcgggta gattgccgaa cgtagagctt    420
acgagccagc ggaaacagta gccgcaggat aagtaagggg agtaagtgat cgaacgaatc    480
agaagtgaca atatacttag gctggatctc gtcccgtgaa tcccaaccct caccaactac    540
gagataagag gtaagccaaa aatcgacttg gtggcgacca acgactgttc ccccctgta     600 actaatcgtt ccgtcaaaac ctgacttact tcaaggccaa ttccaagcgc aaacaatacc    660
gtcctagttc ttcggttaag tttccgaagt aggagtgagc ctacctccgt ttgcgtcttg    720
ttaccactga cccagctatt tactttgtat tgcctgcaat cgaatttctg aactctcaga    780
tagtggggat aacgggaaag ttcctatatt tgcgaactaa cttagccgtc cacctcgaag    840
ctacctactc acacccaccc cgcgcggggt aaataaggca ctaatcccag ctgagagctg    900
gcgtagcact tagccacaag ttaattaaca gttgtctggt agtttggcgg tattaggaag    960
atcctagaag caaggcagag ttagttctaa cctaaagcca caaataagac aggttgccaa   1020
agcccgccgg aaattaaatc ttgctcagtt cggtaacgga gtttccctcc cgcgtactta   1080
attcccaata agaaacgcgc ccaagtccta tcaggcaaaa ttcagcccct tcccgtgtta   1140
gaacgagggt aaaaatacaa gccgattgaa caagggttgg gggcttcaaa tcgtcgttta   1200 ccccactttta caacggagat taagtagttc accctatagt acgaagcaga actatttcga   1260
ggggcgtgca ataatcgaat cttctgcggt tgacttaaca cgctagggac gtgccctcga   1320
ttcaatcgaa ggtactccta ctcagactgc ctcacaccca gctagtcact gagcgataaa   1380
attgacccgc cctctaggga agcgagtacg tcccaaaggg ctccggacag ggctatatag   1440
gagagtttga tctcgccccg acaactgcaa ccctcaactc ccttagataa tattgttagc   1500
cgaagttgca cgacccgccg tccacggact gctcttaggg tgtggctcct taatctgaca   1560
acgtgcaacc cctatcgaag tcgattgttt ctgcgaaagg tgttgtccta atagtcccga   1620
aatttggccc ttgtaggtgt gaaaccactt agcttcgcgc cgtagtccta aaggcccacc   1680
tattgacttt gtttcgggta gcactaggaa tcttaacaat ttgaatttgg acgtggaacg   1740
cgtacacctt aatctccgaa taattctagg gatttggaag tcctctacgt tgacacacct   1800
acactgctcg aagtaaatat acgaataacg cgggcctcgc ggagccgttc cgaatcgtca   1860
cgtgttcgtt tactgttaat tggtggcaaa taagcaatat cgtagtccgt caggcccagc   1920
cctgttatcc acggcgttat ttgtcaaatt gcgtagaact ggattgactg cctgacaata   1980
cctaattatc ggtacgaagt ccccgaatct gtcgggctat ttcactaata cttttccaaac  2040 gccccgtatc caagaagaac gaatttatcc acgctcccgt ctttgggacg aataccgcta   2100
caagtggaca gaggatcggt acgggcctct aataaatcca acactctacg ccctcttcaa   2160
gagctagaag aacagggtgc agttggaaag ggaattattt cgtaaggcga gccaataccg   2220
taattaattc ggaagagtta acacgattgg aagtaggaat agtttctaac cacgttact    2280 aatcctaata acggaacgct gtctgataga ttagtgtcag cgctcggtac caaagaaaaa   2340 taaaagacg ctgaaaagcg tcttttttatt tttcggtcca gtgtaactca ggcaaaagca    2400
cgtaatattc gtactttctt cctccgtaag cgtcacccac attccttaaa gagtgcatgt    2460
gcatattttg ttatcaataa aaaaggccgc gatttgcggc cttattgttc gtcttgccgg    2520
attacgcccc gccctgccac tcatcgcagt attgttgtaa ttcattaagc attctgccga    2580
catggaagcc atcacaaacg gcatgatgaa cttggatcgc cagtggcatt aacaccttgt    2640
```

```
cgccttgcgt ataatatttt cccatagtga aacgggggc gaagaagttg tccatatttg      2700
ctacgtttaa atcaaaactg gtgaaactca cccacggatt ggcactgacg aaaaacatat    2760
tttcgataaa ccctttaggg aaatatgcta agttttcacc gtaacacgcc acatcttgac    2820
tatatatgtg tagaaactgc cggaaatcgt cgtggtattc tgaccagagc gatgaaaacg    2880
tttcagtttg ctcatggaaa acggtgtaac aagggtgaac actatcccat atcaccagct    2940 caccgtctt  cattgccata cgaaactccg gatgtgcatt catcaggcgg gcaagaatgt    3000
gaataaaggc cggataaaac ttgtgcttat ttttctttac ggttttaaa aaggccgtaa     3060 tatccagctg aacggtttgg ttataggtgc actgagcaac tgactggaat gcctcaaaat    3120
gttctttacg atgccattga cttatatcaa ctgtagtata tccagtgatt ttttctcca    3180 ttttagcttc cttagcttgc gaaatctcga taactcaaaa aatagtagtg atcttatttc    3240
attatggtga aagttgtctt acgtgcaaca ttttcgcaaa aagttggcgc tttatcaaca    3300
ctgtcggaat gacaaatggt tccaattatt gaacacccctt cggggtgttt ttttgtttct   3360
ggtttcccga ggccggcctg cgctagcgga gtgtatactg gcttactatg ttggcactga    3420
tgagggtgta agtgaagtgc ttcatgtggc aggagaaaaa aggctgcatc ggtgcgtcag    3480
cagaatatgt gatacaggat atattccgct tcctcgctca ctgactcgct acgctcggtc    3540
gttcgactgt ggcgagcgga aatggcttac gaacggggcg gagatttcct ggaagatgcc    3600
aggaagatac ttaacaggga agtgagaggg tcgcggcaaa gccgtttttc cataggctcc    3660
gcccccctga caagcatcac gaaatctgac gctcaaatca gtggtggcga aacctgacag    3720
gactataaag ataccaggcg tttccccctg gcggctccct cgtgcgctct cctgttcctg    3780
cctttcggtt tgccggtgtc attcctctgt tacggccgag tttgtctcat tccacgcctg    3840
acactcagtt ccgggtaggc agttcgctcc aagctggact gtatgcacga accccccgtt    3900
cagtccgacc gctgcgcctt atccggtaac tatcgtcttg agtccaaccc ggaaagacat    3960
gcaaaagcac cactgcagc agccactggt aattgattta gaggagttag tcttgaagtc    4020
atgcgccgga taaggctaaa ctgaaaggac aagttttggc gactgcgctc ctccaagcca    4080
gttacctcgg ttcaaagagt tggtagctca gagaaccttc gaaaaaccgc cctgcaaggc    4140
ggttttttcg ttttcagagc aagagattac gcgcagacca aaacgatctc aagaagatca    4200
tcttattaat cagataaaat atttctagat ttcagtgcaa tttatctctt caaatgtagc    4260
accggcgcgc cgtgaccaat tattgaaggc cgctaacgcg gccttttttt gtttctggta    4320
tcccgaatgg agcgacttct ccccaaaaag cctcgctttc agcacctgtc gtttcctttc    4380
ttttcagagg gtattttaaa taaaaacatt aagttatgac gaagaagaac ggaaacgcct    4440
taaaccggaa aattttcata aatagcgaaa cccgcgagg tcgccgcccc gtaacctgtc     4500
ggatcaccgg aaaggacccg taaagtgata atgattatca tctacatatc acaacgtgcg    4560
taaagggtaa gtatgaaggt cgtgtactcc atcgctacca aattccagaa acagacgct     4620 ttcgagcgtc tttttcgtt tggtcacga cgtacggtgg aagattcgtt accaattgac      4680
agctagctca gtcctaggta tatacataca tgcttgtttg tttgtaaact actgttttca    4740
ttaaagagga gaaggaagc catgtccatc tatcaggagt ttgttaacaa gtattccctg    4800
tctaaaaccc tgcgttttga actgatcccg cagggcaaaa ctttggaaaa cattaaagcg    4860
cgtggcctga ttctggatga cgaaaaacgt gcaaaggatt acaagaaagc taaacagatc    4920
atcgacaaat atcaccagtt ctttatcgaa gaaattctgt cgtcggtgtg catcagtgag    4980
gatctgttac agaattattc tgatgtatac tttaaactta aaaagtccga tgacgataat    5040
```

```
ctgcaaaaag atttcaagtc agccaaagat accatcaaga aacagatctc agaatatatt    5100
aaagatagcg aaaagttcaa aaacctgttt aaccaaaacc tcattgatgc taagaaaggc    5160
caagaatctg acctgatctt atggctgaaa cagagcaaag ataacggcat tgaactgttc    5220
aaagctaata gcgacatcac cgatattgat gaagcgctcg aaatcatcaa gtctttcaaa    5280
ggctggacga cgtatttcaa aggttttcat gaaaccgta agaatgtata ttcgagcaac     5340
gatattccga cctctattat ttatcgtatc gtggacgaca acctgccgaa gtttctggaa    5400
aacaaagcga atatgaatc tctgaaagac aaagcaccgg aagctattaa ctatgaacag     5460
atcaagaaag atctggcgga agaactgacc ttcgacatcg actataaaac ctccgaagtt    5520
aaccagcgtg ttttctcact ggacgaggtt ttcgaaatcg ctaatttcaa caattacctg    5580
aatcaatctg gcatcaccaa attcaacacc attattggtg gcaaatttgt taacggcgaa    5640
aacaccaagc gtaagggcat caacgaatac attaacctgt atagccaaca aatcaacgac    5700
aaaaccctga aaagtataa aatgtccgtt ctgtttaaac agattttatc ggacaccgaa     5760
tctaaatcct tcgtaattga taaactggaa gatgatagcg acgttgtcac cacgatgcag    5820
agcttttatg agcagattgc ggcgttcaaa accgtggaag agaaatctat taagaaaact    5880
ctgtccctgc tctttgacga cctcaaagcg cagaaactag atctgtctaa gatttacttt    5940
aaaaacgaca atctctgac cgatctcagt caacaagttt tcgatgacta tagcgtgatc     6000
ggcacggcag ttttggaata catcacccaa caaatcgcgc cgaaaaatct ggacaacccg    6060
tccaagaagg aacaggaact gattgcaaag aaaacagaaa aagctaaata cctgagctta    6120
gaaactatca aactggcact tgaggaattt aataaacatc gtgatattga taaacagtgt    6180
cgttttgagg aaattctggc gaactttgcg gcaatcccga tgatcttcga cgaaattgct    6240
caaaacaaag acaatctggc gcagatctct atcaagtacc agaatcaggg taagaaagat    6300
ctgcttcaag catctgcgga ggacgatgtg aaagcaatta agacttatt agatcagacg     6360 aataacttat tacacaagct caaaatcttc cacatcagcc agagcgagga caaggcgaac    6420
attctggata agatgaaca cttctatctg gtgttcgaag aatgttactt cgaactggca    6480
aacatcgtcc ctctctacaa taaaatccgc aactacatca cgcagaagcc ttactctgac    6540
gagaaattca aactgaactt cgaaaacagc acgctggcga acggctggga taagaacaaa    6600
gagccggaca acaccgcaat cctgttcatc aaagacgaca atactatct gggcgtaatg     6660 aacaagaaga caacaagat cttcgacgat aaagcgatca agaaaacaa gggtgaaggc      6720 tataagaaaa tcgtgtacaa gctcctgccg ggtgcgaata aatgttacc gaaagtgttc     6780 ttttccgcga aaagcatcaa attctacaac ccgtctgagg atattctgcg catccgcaat    6840
catagcacgc acactaaaaa cggtagcccg cagaaagggt atgaaaaatt cgaatttaat    6900
atagaggact gccgtaagtt catcgacttc tataaacaga gcatttccaa acatccggaa    6960
tggaaagact tcggcttccg ttttctgac actcagcgct ataatagcat cgacgagttc     7020
taccgcgaag tggagaatca gggctataaa ctgaccttcg agaacattag tgagtcgtac    7080
atcgactccg ttgtgaatca gggtaaactg tacctgtttc agatctataa taaagacttt    7140
agcgcgtaca gcaaaggccg tccgaatctg cacacccttt actggaaagc attatttgac    7200
gaacgtaacc tgcaagatgt ggtgtataaa ctgaacggtg aggcggaact tttctaccgt    7260
aaacagagta tcccgaagaa aatcacgcat ccggcaaaag aagctattgc caacaaaaac    7320
aaagacaacc cgaagaaaga atcagtattc gaatatgacc tgatcaaaga taaacgtttc    7380
```

```
accgaagata agttctttt ccactgtccg attaccatca acttcaaatc tagcggtgcg    7440
aacaagttca acgatgaaat taacttatta ctgaaagaga aagctaatga cgtacacatc    7500
ttatctattg atcgcggtga acgtcattta gcatactata cactggtaga tggtaaaggt    7560
aatattatta aacaggatac tttcaatatt atcggtaatg accgtatgaa aaccaactat    7620
cacgataagc tggcggcgat cgaaaaagat cgtgattctg cgcgtaaaga ttggaagaaa    7680
attaacaata tcaaagaaat gaagaaggc tatctgagcc aagtggtgca cgagatcgca    7740
aaactggtga ttgaatataa cgctatcgtg gttttcgaag atctgaactt tggttttaaa    7800
cgtggtcgct tcaaagtaga aaacaggtg taccaaaaac tggaaaaaat gctgattgaa    7860
aaactgaact atctggtttt taaagacaac gaatttgaca aaacgggtgg cgtactccgt    7920
gcctatcagc tgaccgctcc gttcgaaacg ttcaagaaaa tgggtaaaca acgggggatt    7980
atctattatg tgccagctgg tttcacctcc aagatttgtc cagttacggg cttcgttaac    8040
cagctgtacc cgaaatacga gagcgttagc aaatctcaag aattttttcag caaattcgac    8100 aagatctgct ataatctgga taaaggctat ttcgagttca gcttcgatta caaaaacttc    8160
ggcgataaag cggctaaagg taagtggact attgctagct ttggtagccg tctgattaac    8220
tttcgcaact ccgacaaaaa ccataattgg gacacgcgtg aagtgtatcc gaccaaagaa    8280
ctggaaaaat tactgaaaga ctattccatc gaatatggtc atgggagtg cattaaagcg    8340 gcgatttgcg gtgaatccga taagaaattt ttcgccaaac tgaccagcgt gcttaacacc    8400
attctgcaaa tgcgtaattc taaaacgggt acggagctgg actacctgat ttctccggta    8460
gccgacgtta acggcaactt cttcgattct cgtcaagcac cgaaaaatat gccacaagac    8520
gcggatgcca acggtgcata ccatatcggc ttaaaaggct taatgttatt aggccgtatc    8580
aagaataatc aggagggcaa gaattaaat ctggttatca aaaacgaaga atacttcgag    8640
ttcgttcaga atcgtaacaa ttaatgtatg cttaagcagc tcggtaccaa agacgaacaa    8700
taagacgctg aaaagcgtct ttttcgttt tggtcctgtt gcggcgcgat agtgtgaaca    8760
tgctatagac ttctggtgct acccgactga caattaatca tccggctcgt ataatgctag    8820
caatttctac tgttgtagat cccgatgtac gcgcgcgtgg atgagtctaa gaactttaaa    8880
taatttgtct gtatattatt tcgagacgaa caataaggcc tccctaacgg gggccttttt    8940
ttattgataa caaagtaac ttcgagcttg tctacctcct agcaccatta ttgcaattaa    9000
taaacaacta acgacaatt ctacctaaca gttttcatat atgacgagca gttaagtgat    9060
gagtaaaggt gaggaattat ttactggtgt tgttccgatc ttagttgaac tggacggcga    9120
tgttaacggt cataaattca gtgttcgtgg tgaaggtgaa ggtgatgcaa ccaacggtaa    9180
gctgaccctg aaattcatct gcactactgg aaaattacca gtaccgtggc ctactctggt    9240
gactaccctg acctatggtg ttcagtgttt ttctcgttac cctgaccaca tgaagcaaca    9300
tgatttcttc aaatctgcaa tgccggaagg ttatgtacag gagcgcacca tttctttcaa    9360
agacgatggc acgtataaaa cccgtgcaga ggttaaattt gaaggtgaca ctctggtgaa    9420
tcgtattgaa ctgaaaggca ttgatttcaa agaggacggc aatatttag gccacaaact    9480 ggaatataac ttcaactccc ataacgttta catcaccgca gacaaacaga gaacgtat      9540 caaagctaac ttcaaaattc gccataacgt tgaagatggt agcgtacagc tggcggatca    9600
ttaccaacag aacactccga ttggagatgc tcctgtttta ctgccggata accactacct    9660
gtccacccag tctaaactgt cgaaggatcc gaacgaaaag cgcgaccaca tggtgttatt    9720
agagttcgtt accgctagtg gtatcacgca cggtatggat gaactctaca aataagacga    9780
```

```
acaataaggg gagcgggaaa ccgctcccct tttttattga taacaaaagt aaattgcacg    9840
ctgatagtct cccaattgcg aaggaccaaa acgaaaaaac acccttttcgg gtgtcttttc    9900 tggaatttgg taccgagtac taggtatcgt gtaagtagcg aaggcccgta cgcgagataa    9960
actgctaggc aaccgcgact ctacgactgg tgctcgattt aatttcgctg acgtaaagaa   10020
attatcggca gtgcgtcaac tgccgtatct ttatcttaat taggtagttg acaagccct    10080 tgaaagaaat agcaagagcc tgcctctcta ttgaagtcac ggcgaaagtc gggtagaaat   10140
caaagaaagc agaaattaaa tcggagtaac actaaggtgg gataactccg taactgacta   10200
cgcctttctc tagactttac ttgaccagat acactgtctt tgacacgttg aaggattaga   10260
gcaatcaaat ccaagactgg ctaagcacga agcaactctt gagtgttaaa aagttatctc   10320
ctgtattcgg gaagcgggta ctagaagatt gcagggactc cgacgttaag taaattacaa   10380
agtaataagt atcgttcagg atcacgttac cgcaataaga agcgagaata atataatttc   10440
cgaagtgctt accccagtag tgactattcc tataacccctt ctgagtgtcc ggaggcggaa   10500
atttgccacg aaagagaaag tatttccccg acaataataa aggggcgctc ctcagctttt   10560
ccacttggtt gggtaagcta ggcaactctg aaaggagttt cggcgaattg aagccgacag   10620
ctttgaattg ttttagggggc gttattcgag ggcaatcgga gctaacttca agactacttc   10680
tttgttgaat actaaatagt gcaaaggtcg tgtttcctca aggatactcc gctaacaata   10740
taggattcca atcagattca gcactggcgg tacgggtgtt gcggtgaggc gttcgggttt   10800
acggctcgaa gctagcacgg taggaagcct gacaatcacc aagcaaaagg gccgtcgaag   10860
gcccacaaga tacgaaagct ctcgaagcct tatccttgac cgatccacct atttaggcag   10920
ttacgcacaa aagctaccca ataatccgtg acaggcacaa tatcacggaa caaaaccgaa   10980
aactctcgta cacggttagg ttttcgctag gaagaataaa cctctatctt gattataaga   11040
aggctcccca agcacccccca aaaccgaaat agcggttttgc aataagggac aagttacgag   11100
tgtagacacg cagaattatc cagcctttag tctttaggaa ggcaaagcta ttgtacgcgg   11160
tagccgtcgt agcaatttac caactgtaga attattggac acacgtagga agggcttaca   11220
gttgaagttt aataaggtca cacgcaaaac cgctaaggaa taatcgcacc gttagcgaaa   11280
gaatatttca gagcggttag taaaggttga gtaaagtgag attccaaagt gagcctttat   11340
aaaaagtaaa gagctataat aaaaccgtcg agcagaaaac aatcgcctga aatctcaagc   11400
acgttgccct ttctaacgtc gctaaggttt cgtaaacccg tttgattagg aagaagaata   11460
agtaacccga ttaggtttga gatcgcgggt tatcggtttg gattaaaagt ggataccagc   11520
ggagtcaacg ccgacgcaaa cgtacagtga tccaatcctg ttgcacggtc aagcacaatc   11580
agctcgcaag atcttggaat agtgtgccca acagtttagt tgagggccac gttccgacta   11640
caagttgctt caagagggga atttggattt ggcaatagcc ccccgtttct acctcaagag   11700
gcgacgagta ttaaccgcgc cagctgtcgg cacaagggcc aaagaagatt ccaatttctt   11760
attcccgaat aacctccgaa tccctgcggg aaaatcaccg accgaatagc ctagaagcaa   11820
gggggaacag ataggtataa ttagcttaag agagtaccag ccgtgacaac agcgtagtaa   11880
ccacaaactt acgctggggc ttcttttggcg gattttttaca gatactaaca aggtgatttg   11940
aagtacctta gttgaggatt taaacgcgct atccggtaat ctccaaattg ggaaataccg   12000
ttcaaagagg gctagaatta cttaaaagcc ttcacaccgc ctgcgctata cgcgcccact   12060
ctcccgttta tccgtccaag cggaagcagg gcgatcctcc gctaagatat tcttacgtgt   12120
```

```
aacgtagcta agtatcccaa atagctggcg tacgcgttga acaccgccta gaggatcgtg   12180
actcgccgga cgagcgtgtt attggggact tacgccagcg tagactacaa cgcgcccaga   12240
ttaaccctgc acgtattgcc ttgaataacg tactaatctc tccggctctc gacaatctat   12300
cgagcgactc gattatcaac gggtgtcttg cagtt                              12335
```

TRANSCRIPTIONAL CONTROL IN PROKARYOTIC CELLS USING DNA-BINDING REPRESSORS

CROSS-REFERENCE TO RELATED APPLICATION

This application claims benefit and priority to U.S. Provisional Application No. 62/818,903, filed Mar. 15, 2019 which is incorporated herein by reference in its entirety.

REFERENCE TO SEQUENCE LISTING SUBMITTED VIA EFS-WEB

This application includes an electronically submitted sequence listing in .txt format. The .txt file contains a sequence listing entitled "2643-5 TK1_ST25.txt" created on Apr. 24, 2020 and is 53,644 bytes in size. The sequence listing contained in this .txt file is part of the specification and is hereby incorporated by reference herein in its entirety.

TECHNICAL FIELD

The present disclosure relates generally to methods and compositions for transferring a genetic circuit from one prokaryotic cell ("donor cell") to another prokaryotic cell ("recipient cell" or "target cell" which are used interchangeably herein).

BACKGROUND

Inducible systems that control the transcription from a given promoter are useful tools in molecular biology [1]-[3]. In general, these systems are composed of a protein repressor whose binding to its cognate DNA operator is dependent on the presence of an inducer. In the absence of inducer, the repressor is able to recognize its operator, preventing transcription from a promoter; when the inducer is present, the repressor is no longer able to recognize its operator, either by binding of the inducer to a domain of the repressor or by changing its 3D conformation, hence activating transcription. Inducers can be chemical (IPTG, sugars, small molecules, proteins, etc.) or physical (heat, light, pressure, pH etc.). There are many other ways to prevent transcription or to reduce the amount of protein being made in a cell: conditional degradation of proteins, reduction of plasmid copy numbers in the production strain, etc. These do not repress the promoter per se but act upon other components of the genetic circuit [22].

It may, in some instances, be desirable to control the transcription/translation of a specific gene in a host while being able to activate it in a target bacterium in the absence of inducer. For example, in the case of phagemid transduction of proteins and/or nucleic acids that are toxic to the target bacterium, such as for example CRISPR-Cas9-containing circuits [14], it is imperative that the strain being used to produce the particles does not express the toxic protein and/or nucleic acid encoded by the circuit: otherwise, the production strain would be killed or critically damaged. However, it is necessary that the toxic protein and/or nucleic acids are expressed/transcribed in the target strain to induce either cell death such as sequence-specific cell death or any other type of desired function in the target strain. This would also be true for any other toxic component that will be injected in a target strain, which could also render it toxic for the production strain. Additionally, it has been shown that the constitutive expression of components in genetic circuits, especially if they impose a burden (such as toxic components, or any component having unwanted function in the production strain) is disadvantageous for the cell and they tend to be deleted or mutated, causing undesired breakage of designs and components [15]. In that sense, having a conditional repressor that acts only in the production strain is advantageous from the engineering/manufacturing point of view.

A proposed solution for the specific case of genetic circuit transduction has been offered and involves positive regulators (a phage polymerase and its cognate promoter). The target cells may contain either the promoter or the polymerase only, with the other component being transduced by a phagemid [12][13]. However, this is not a practical approach when working with wild-type strains, because of difficulties to transform one of the components, or in environments where it is not possible to pre-load the target cells with one of the circuit constituents (for example, the gut environment).

Another possible solution for this would be to express the repressor controlling the expression of the toxic component in trans, i.e., not encoded in the circuit to be packaged. In this case, the repressor would only be present in the production strain but not in the target strain. There is, however, a main problem associated with this approach: since strains used to produce phagemids are the same species (or at least very closely related) as those that need to be targeted, the repressor used needs to be carefully chosen. For example, using AraC or LacI would effectively repress the transcription of toxic components in the production strain in trans, and phagemids produced in this way would inject a "naked", constitutive promoter into the target strains. However, if these are wild-type strains, they will most probably contain their own genes for LacI or AraC, so the injected promoter would be immediately repressed. Even antibiotic-induced systems, such as TetR, are very commonly found in many wild-type strains. The same can happen when using a phage master-repressor-promoter pair: wild-type strains carry a number of prophages in their genomes, and many of these could encode repressors that recognize the promoter being used.

SUMMARY

Described herein are novel methods and compositions for use in transferring a genetic circuit of interest from a prokaryotic cell (referred to herein as a "donor cell") to another prokaryotic cell (referred to herein as a "recipient cell" or "target cell"). In certain aspects, the prokaryotic cells are bacterial cells. Further, the genetic circuit comprises a nucleic acid of interest under the transcriptional control of a repressor binding sequence (also referred to herein as promoter/operator). Said nucleic acid sequence of interest may encode a protein or RNA of interest.

The disclosed methods and compositions are based on the expression of one or more repressor proteins in the donor cell, and the presence of a repressor binding sequence positioned within the genetic circuit, that function to repress transcription of the nucleic acid sequence of interest when present in the donor cell. The genetic circuit does not encode said one or more repressor proteins. Thus, upon transfer of the genetic circuit into the recipient cell, said recipient cell being chosen for its lack of expression of said one or more repressor proteins, the nucleic acid sequence of interest is then transcribed.

Methods are provided for the transfer of a genetic circuit from a donor cell to a recipient or target cell. Said transfer may be achieved by a variety of different methods. Such as non limiting examples of transfer include bacterial transduction, conjugation and transformation. In one specific aspect, bacterial delivery vehicles, such as bacteriophage scaffolds, are assembled in the donor cell as a means for efficient transfer of the genetic circuit into a recipient or target cell. In such instances, the donor cell comprises prophage sequences that provide in trans the bacteriophage components, such as capsid proteins, required for assembly of the genetic circuit into bacteriophage particles. Further, the genetic circuit is engineered to contain cis acting packaging signals that mediated the encapsidation of the genetic circuit into the capsid.

Thus, the present disclosure relates to a method of transferring a genetic circuit from a donor cell to a target cell comprising contacting the donor cell with the target cell for a sufficient amount of time to allow transfer of the genetic circuit into the target cell wherein said donor cell expresses a repressor protein, that is not encoded by the genetic circuit and is absent in the target cell and wherein the genetic circuit comprises a nucleic acid sequence of interest under the transcriptional control of a repressor binding sequence. The donor cell may be a bacterial donor cell and the target cell may be a bacterial target cell. The genetic circuit may be packaged within a bacterial delivery vehicle before transfer. In an embodiment, the genetic circuit packaged in the delivery vehicle is a packaged phagemid. The nucleic acid sequence of interest may encode a protein of interest and/or a RNA molecule of interest. In particular, the nucleic acid sequence of interest may encode a protein (i) which is a toxic protein, such as a protein which is toxic to a bacterial cell, in particular to the target cell, more particularly a toxic protein selected from the group consisting of holins, endolysins, restriction enzymes and toxins affecting the survival or the growth of the target cell, (ii) which is a nuclease, such as a CRISPR nuclease, and/or which is a therapeutic protein. Alternatively, or additionally, the nucleic acid sequence of interest may encode a RNA molecule of interest, in particular selected from the group consisting of mRNA, crRNA, tRNA, iRNA, asRNA, ribozyme RNA, guide RNA and RNA aptamers. In a particular embodiment, the nucleic acid sequence of interest encodes a CRISPR nuclease and the genetic circuit further comprises a nucleic acid sequence encoding a guide RNA. In an embodiment, said nucleic acid sequence encoding a guide RNA is under the transcriptional control of a constitutive promoter. In some embodiments, the nucleic acid sequence of interest is a nucleic acid encoding a RNA such as a mRNA, crRNA, tRNA, iRNA (interference RNA), asRNA (anti-sense RNA), ribozyme RNA, RNA aptamer or a guide RNA, a CRISPR locus, a toxin gene, a gene encoding an enzyme such as a nuclease or a kinase, a gene encoding a nuclease selected from the group consisting of a Cas nuclease, a Cas9 nuclease, a TALEN, a ZFN and a meganuclease, a gene encoding a recombinase, a bacterial receptor, a membrane protein, a structural protein or a secreted protein, a gene encoding resistance to an antibiotic or to a drug in general, a gene encoding a toxic protein or a toxic factor, and a gene encoding a virulence protein or a virulence factor, or any of their combinations. More particularly, the nucleic acid sequence of interest may be selected from the group consisting of a nucleic acid encoding one or more of the following: Cas nuclease, Cas9 nuclease, guide RNA, CRISPR locus, toxin, enzyme, nuclease, a kinase, TALEN, ZFN, meganuclease, recombinase, bacterial receptor, membrane protein, a structural protein, secreted protein, protein conferring resistance to an antibiotic or a drug, a toxic protein or a toxic factor, virulence protein, and virulence factor. In an embodiment, the repressor protein is selected from the group consisting of the repressor proteins listed in Table 1. In an embodiment, the repressor proteins are selected from the group consisting of Ph1F, SrpR, LitR, PsrA, AmeR, McbR, QacR, TarA, ButR, Orf2 and ScbR.

Methods are also provided for production of bacterial delivery vehicles, packaged phagemids for example, for use in efficient transfer of a desired genetic circuit into a recipient or target cell. The disclosure relates to the use of donor cells as described herein, that express one or more repressor proteins for the controlled expression of a nucleic acid of interest, such as a nucleic acid encoding a toxic or unwanted protein and/or RNA molecule, during production of the bacterial delivery vehicle of interest. The repressed transcription of the nucleic acid of interest in the donor cell may result from the functional positioning of the repressor binding sequence in close proximity to the nucleic acid of interest. Alternatively, the repressed transcription of the nucleic acid of interest in the donor cell may result from the functional positioning of the repressor binding sequence away from the nucleic acid of interest. In contrast, once transferred to the recipient or target cell, the nucleic acid of interest is transcribed due to the absence of said one or more repressor proteins in said cell and the absence of nucleic acid sequence(s) encoding said repressor protein(s) within the genetic circuit.

In one aspect, methods of producing delivery vehicles using the donor cells disclosed herein are provided. In certain embodiments, the delivery vehicles are prepared by introducing the genetic circuit of interest described herein into a donor cell under conditions that permit formation of the delivery vehicles. For example, in certain embodiments, the method comprises (i) introducing into a donor cell the genetic circuit of interest; and (ii) allowing a sufficient amount of time for replication of the genetic circuit of interest and packaging of the genetic circuit into the delivery vehicles. In one aspect, the method may further comprise the step of collecting and, optionally, purifying the delivery vehicles. In particular, the present disclosure relates to a method of producing delivery vehicles comprising i) introducing a genetic circuit into a donor cell expressing a repressor protein, wherein said genetic circuit comprises a nucleic acid of interest under the transcriptional control of a repressor binding sequence recognized by said repressor protein and the repressor protein is not encoded by the genetic circuit; and allowing a sufficient amount of time for replication of the genetic circuit of interest and packaging of the genetic circuit into the delivery vehicles. The method may further comprise a step of collecting the delivery vehicles and optionally a step of purifying the delivery vehicles. In an embodiment, in said method, the donor cell, such as a bacterial donor cell, comprises prophage sequences encoding proteins required in trans for assembly of the genetic circuit into a delivery vehicle. In an embodiment, the genetic circuit is a phagemid and/or the delivery vehicle is a bacterial delivery vehicle, such as a bacteriophage. In an embodiment, the delivery vehicles may be to be used in a target cell, for example, a bacterial target cell, which does not express the repressor protein. The present disclosure also relates to the delivery vehicle obtained by said method. The present disclosure also relates to a genetic circuit comprising a transcriptional promoter controlled by a repressor protein and a nucleic acid sequence of interest placed under the control of said transcriptional promoter, said genetic circuit not encoding the repressor protein and being packaged within a bacterial delivery vehicle. In an embodiment said genetic circuit is a phagemid. It also relates to the use of a delivery vehicle or a genetic circuit as described herein to transfer a genetic circuit from a donor cell to a target cell, wherein the donor cell expresses the repressor protein and the target cell does not express said repressor protein.

In yet another aspect, the disclosure provides donor cells comprising one or more expressed repressor proteins and a genetic circuit of interest. In an embodiment, the genetic circuit of interest comprises a nucleic acid sequence of interest placed under the transcriptional control of a repressor binding sequence recognized by said one or more expressed repressor proteins. Further, in certain embodiments where delivery vehicles are produced, the donor cell may also comprise prophage sequences encoding proteins required in trans for assembly of the genetic circuit of interest into a delivery vehicle. Such proteins include, for example, structural bacteriophage proteins, e.g., capsid proteins. In some particular aspects, the present disclosure relates to a donor cell comprising a genetic circuit comprising a transcriptional promoter controlled by a repressor protein that is expressed by said donor cell but is not encoded by the genetic circuit. In an embodiment, the genetic circuit comprises a nucleic acid sequence of interest placed under the control of the transcriptional promoter. The donor cell may further comprise prophage sequences that provide in trans the bacteriophage components required for assembly of the genetic circuit into bacteriophage particles. The genetic circuit may further comprise cis acting packaging signals that mediate encapsidation of the genetic circuit into a capsid.

The donor cells of the present disclosure comprise a genetic circuit of interest. In certain embodiments, the genetic circuit comprises an expression or transcription cassette having a nucleic acid of interest under the transcriptional control of a repressor binding sequence. Such nucleic acids of interest are selected, for example, from the group consisting of a nucleic acid encoding a RNA such as a mRNA, crRNA, tRNA, iRNA (interference RNA), asRNA (anti-sense RNA), ribozyme RNA, RNA aptamer or a guide RNA, a CRISPR locus, a toxin gene, a gene encoding an enzyme such as a nuclease or a kinase, a gene encoding a nuclease selected from the group consisting of a Cas nuclease, a Cas9 nuclease, a TALEN, a ZFN and a meganuclease, a gene encoding a recombinase, a bacterial receptor, a membrane protein, a structural protein or a secreted protein, a gene encoding resistance to an antibiotic or to a drug in general, a gene encoding a toxic protein or a toxic factor, and a gene encoding a virulence protein or a virulence factor, or any of their combination. In an embodiment, the nucleic acid of interest encodes a therapeutic protein. In another embodiment, the nucleic acid encodes an anti-sense nucleic acid molecule. In some embodiments, the nucleic acid of interest encodes two or more molecules of interest. In particular, one of these molecules may be a nuclease, for instance a Cas nuclease, and another may be a nucleic acid molecule such as a guide RNA. In one aspect, the nucleic acid of interest encodes a nuclease that performs cleavage of a recipient or target cell genome or recipient or target cell plasmid. In some aspects, the cleavage occurs in an antibiotic resistant gene. In another embodiment, the nucleic acid of interest encodes a nuclease that targets cleavage of a recipient or target cell genome and said nuclease is designed to stimulate a homologous recombination event for insertion of a nucleic acid of interest into the genome of the cell.

In an embodiment, in the provided methods or the provided donor cell, the genetic circuit is a phagemid, and/or the donor cell is a bacterial cell, for example, a bacteria cell from the *E. coli* specie.

The present disclosure also provides pharmaceutical or veterinary compositions comprising donor cells, or one or more of the bacterial delivery vehicles assembled in said donor cells, and a pharmaceutically-acceptable carrier. It is also provided a pharmaceutical or veterinary composition comprising a delivery vehicle and/or a genetic circuit as disclosed herein, and a pharmaceutical acceptable excipient. Also provided is a method for treating a disease or disorder caused by bacteria, for example, a bacterial infection, comprising administering to a subject having said disease or disorder in need of treatment the provided pharmaceutical or veterinary composition. Further provided is (i) a pharmaceutical or veterinary composition as disclosed herein for use as a medicament, and in particular in the treatment of a disease or disorder caused by bacteria, for example, a bacterial infection, and (ii) the use of a pharmaceutical or veterinary composition as disclosed herein for the manufacture of a medicament for treating a disease or disorder caused by bacteria, such as a bacterial infection. A method for reducing the amount of virulent and/or antibiotic resistant bacteria in a bacterial population, in particular in a subject having a bacterial infection, is provided comprising contacting the bacterial population with the disclosed compositions herein. Further provided is the use of a pharmaceutical or veterinary composition as disclosed herein for the manufacture of a medicament for reducing the amount of virulent and/or antibiotic resistant bacteria in a bacterial population, in particular in a subject having a bacterial infection.

The present disclosure further provides kits for use in the transfer of a genetic circuit of interest from a donor cell to a recipient or target cell. In one embodiment, the kit comprises (i) a donor cell expressing a repressor protein; and (ii) a genetic circuit of interest. Said genetic circuit may comprise an expression cassette into which a nucleic acid of interest may be inserted in functional proximity to a repressor binding sequence recognized by said repressor protein. Optionally, the donor cell of the kit may contain prophage sequences for assembly of delivery vehicles, for example, bacteriophages proteins for packaging of the genetic circuit of interest. The kit may further comprises a recipient or target cell wherein said recipient or target cell fails to express the repressor protein thereby permitting expression of the nucleic acid of interest following transfer into said cells.

BRIEF DESCRIPTION OF FIGURES

In order to better understand the subject matter that is disclosed herein and to exemplify how it may be carried out in practice, embodiments will now be described, by way of non-limiting example, with reference to the accompanying drawings. With specific reference to the drawings, it is stressed that the particulars shown are by way of example and for purposes of illustrative discussion of embodiments of the disclosure.

DETAILED DESCRIPTION

Figure 1:
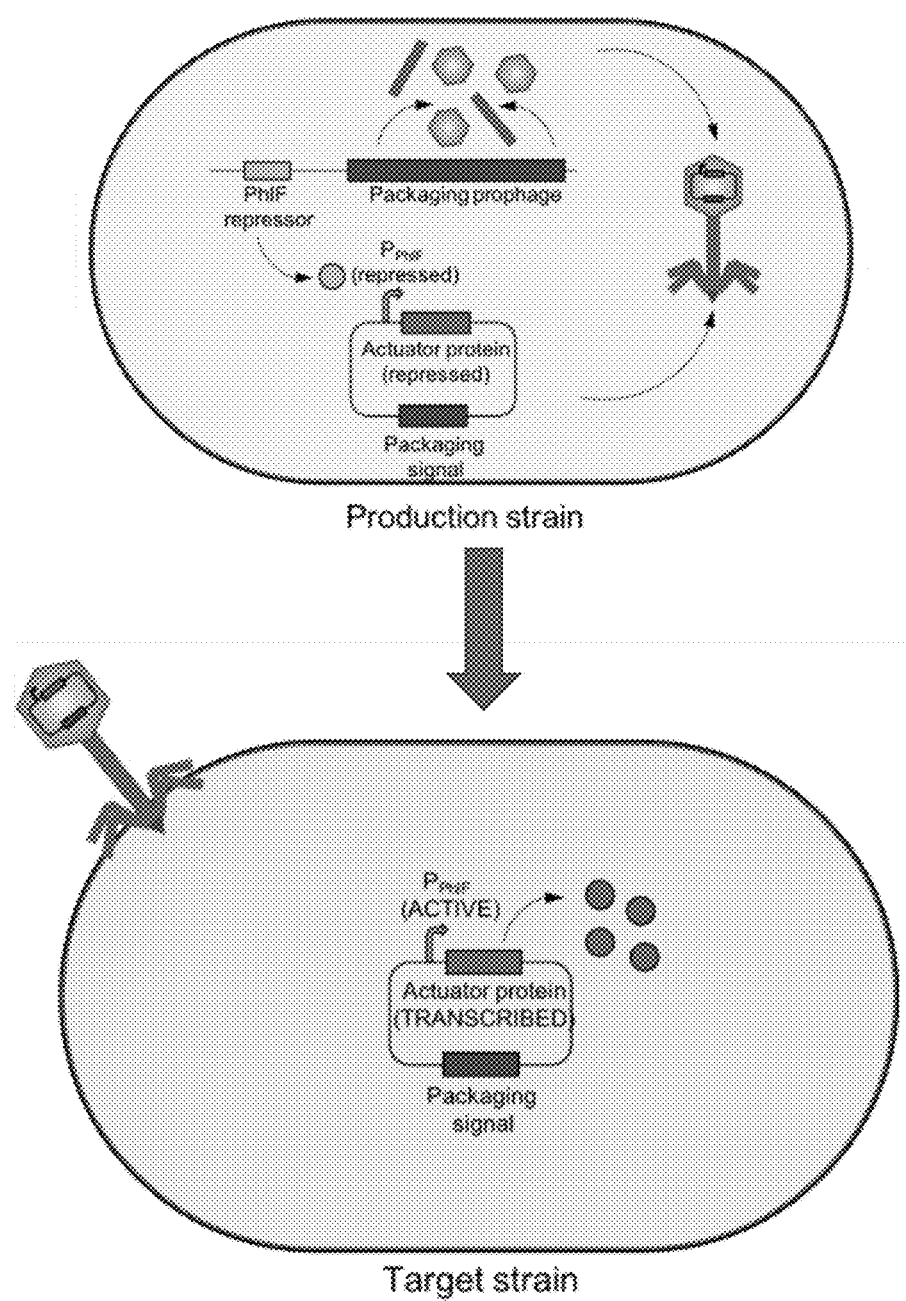
FIG. 1 depicts conditional transcriptional control with an interspecific repressor. On the left, the donor strain, containing a packaging prophage and the Ph1F repressor in trans. The genetic circuit carries the packaging signal and a nucleic acid of interest (encoding an actuator protein) under the control of a $P_{ph1F}$ promoter. Upon packaging of the genetic circuit, target or recipient cells can be transduced and the $P_{ph1F}$ promoter will be active since recipient cells lack the Ph1F repressor (not present in *E. coli*). Note that the Ph1F repressor can be replaced with a dCas9+gRNA targeting the promoter, RBS or sequence of the actuator.

Disclosed herein are novel approaches for delivery of a genetic circuit into a recipient or targeted cell. In one embodiment, novel methods are provided for production of bacterial delivery vehicles for use in efficient transfer of a desired genetic circuit into a target cell. The methods and compositions of the present disclosure are based on the use of a donor cell that expresses one or more repressor proteins for the controlled expression of a protein, such as a toxic protein, and/or a nucleic acid, such as a RNA molecule. This is particularly important, for example, when the genetic circuit is designed to express a toxic protein and/or RNA molecule.

Donor cells expressing one or more repressor proteins are provided. In preferred embodiments, the term "donor cell" refers to donor bacterial cells. As used herein, the term "repressor protein" refers, for example, to a protein that binds to a specific site (herein "repressor binding sequence") on a nucleic acid and prevents transcription of nearby genes. Typically, a repressor protein is a DNA-binding protein that blocks the attachment of RNA polymerase to the promoter through its binding to a repressor binding sequence (an operator), thus preventing transcription of the genes. Said donor cells may be cells that naturally express one or more repressor proteins. Alternatively, the donor cells may be recombinantly engineered to express one or more repressor proteins. Additionally, the provided donor cells comprise a genetic circuit of interest wherein said genetic circuit contains a nucleic acid of interest under the transcriptional regulation of a repressor binding sequence and does not contain a nucleic acid encoding a repressor protein which is able to bind to said repressor binding sequence. At least one repressor protein expressed by the donor cell is able to bind to said repressor binding sequence thereby preventing transcription of the nucleic acid of interest. Said nucleic acid of interest may encode a protein and/or RNA of interest.

Repressor proteins that may be utilized in donor cells include, for example, those listed in Table 1. In an embodiment, the donor cell expresses a repressor protein selected from the repressor proteins listed in Table 1 and the nucleic acid of interest contained within the genetic circuit is under the transcriptional regulation of a repressor binding sequence bound by said repressor protein.

TABLE 1

| Repressor protein | SwissProt Accession number |
| --- | --- |
| AmeR | Q9F8V9 |
| AmrR | Q9RG61 |
| AmtR | Q9S3L4 |
| ArpA | Q54189 |
| ArpR | Q9KJC4 |
| BarA | Q9LBV6 |
| BarB | O24739 |
| BM1P1 | O68276 |
| BM3R1 | P43506 |
| BpeR | Q6VV70 |
| ButR | Q9AJ68 |
| CalR1 | Q8KNI9 |
| CampR | Q93TU7 |
| CasR | Q9F6W0 |
| CprB | O66129 |
| CymR | O33453 |
| Cyp106 | Q59213 |
| DhaR | Q9RAJ1 |
| Ef0113 | Q8KU49 |
| EthR | P96222 |
| FarA | O24741 |
| HapR | O30343 |
| HemR | P72185 |
| HlyIIR | Q63B57 |
| IcaR | Q9RQQ0 |
| IcaR | Q8GLC6 |
| IfeR | O68442 |
| JadR2 | Q56153 |
| KstR | Q9RA03 |
| LanK | Q9ZGB7 |
| LitR | Q8KX64 |
| LmrA | O34619 |
| LuxT | Q9ANS7 |
| McbR | Q8NLK1 |
| MmfR | Q9JN89 |
| MtrR | P39897 |
| NonG | Q9XDF0 |
| OpaR | O50285 |
| Orf2 | Q9XDV7 |
| orfL6 | Q8VV87 |
| PaaR | Q9FA56 |
| PhlF | Q9RF02 |
| PqrA | Q9F147 |
| PsbI | Q9XDW2 |
| PsrA | Q9EX90 |
| Q9ZF45 | Q9ZF45 |
| QacR | P0A0N4 |
| RmrR | Q9KIH5 |
| ScbR | O86852 |
| SmcR | Q9L8G8 |
| SmeT | Q8KLP4 |
| SrpR | Q9R9T9 |
| TarA | Q9RPK9 |
| TcmR | P39885 |
| ThlR | O85706 |
| TtgR | Q9AIU0 |
| TtgW | Q93PU7 |

TABLE 1-continued

| Repressor protein | SwissProt Accession number |
| --- | --- |
| TylP | Q9XCC7 |
| TylQ | Q9ZHP8 |
| UrdK | Q9RP98 |
| VanT | Q8VQC6 |
| VarR | Q9AJL5 |
| YdeS | P96676 |
| YDH1 | P22645 |
| YixD | P32398 |

Repressor binding sequences corresponding to such repressor proteins are well known in the art and the skilled person may easily choose functional pairs of repressor protein/repressor binding sequence. In some embodiments, the donor cell expresses one or several repressor proteins corresponding to one or several repressor binding sequences contained in the genetic circuit. The repressor protein(s) expressed by the donor cell and/or the repressor binding sequence(s) comprised on the genetic circuit may be heterologous to the donor cell, i.e. are not naturally present in said donor cell. In particular, the repressor protein(s) expressed by the donor cell and/or the repressor binding sequence(s) comprised on the genetic circuit may come from a different bacterial species that the donor cell, for example, from a different bacterial genus. In an embodiment, the repressor protein(s) expressed by the donor cell and/or the repressor binding sequence(s) comprised on the genetic circuit are endogenous to the donor cell, i.e. are naturally present in said donor cell.

In another embodiment, the repressor protein is a CRISPR nuclease devoid of nuclease activity. In this embodiment, the repressor protein is used in combination with a guide RNA targeting a sequence required for transcription of the nucleic acid of interest. In this embodiment, the donor cell thus also expresses said guide RNA in addition to the CRISPR nuclease acting as repressor protein. In particular, the guide RNA may target a control sequence such as the promoter, RBS or repressor binding sequence operably linked to the nucleic acid of interest. Alternatively, the guide RNA may target a non controlling sequence such as the coding region of the nucleic acid of interest. In this case, said non controlling sequence should be considered as the repressor binding sequence. Thanks to this guide RNA, the CRISPR nuclease devoid of nuclease activity is able to bind the targeted sequence without inducing any break, thereby preventing transcription of the nucleic acid of interest without altering the integrity of the genetic circuit. CRISPR nucleases devoid of nuclease activity such as dead Cas9 (dCas9) are well known by the skilled person.

In addition to expression of a repressor protein, the donor cell may further comprise a packaging prophage that provides in trans the necessary components for assembly of bacterial delivery vehicles, such as for example bacteriophage scaffold. Once produced, the delivery vehicles may be advantageously used to transfer the genetic circuit of interest into a recipient or target cell. The absence of repressor protein in the recipient or targeted cell results in expression of the transferred genetic circuit of interest.

As used herein, the term "genetic circuit", for example, refers to a nucleic acid construct, for example, a linear or circular double stranded DNA molecule, comprising one or more nucleic acid of interest operably linked to control sequences including a transcriptional promoter ("promoter") and a repressor binding sequence (recognized by at least one repressor protein expressed by the donor cell). The genetic circuit may further comprise one or more additional nucleic acid sequences operably linked to one or several control sequences including a transcriptional promoter. In particular, the genetic circuit may comprise one or more nucleic acid of interest operably linked to control sequences including a promoter and a repressor binding sequence (recognized by at least one repressor protein expressed by the donor cell), and one or more nucleic acid sequences operably linked to a constitutive promoter. For example, in a particular embodiment, the genetic circuit comprises a nucleic acid of interest encoding a CRISPR nuclease operably linked to control sequences including a promoter and a repressor binding sequence (recognized by at least one repressor protein expressed by the donor cell), and a nucleic acid sequence encoding a guide RNA operably linked to a constitutive promoter. The term "operably linked" means a configuration in which a control sequence is placed at an appropriate position relative to a nucleic acid of interest, in such a way that the control sequence directs expression of said nucleic acid. Optionally, the genetic circuit may include other control sequences such as leader sequence, polyadenylation sequence, propeptide sequence, ribozyme, hairpin-forming sequences, ribosome binding site, signal peptide sequence and/or transcription terminator. In some embodiments, the genetic circuit is a plasmid or a phagemid, i.e. comprises a genetic sequence that signals for packaging. In some embodiments, the genetic circuit is a phagemid.

In one aspect, methods of producing delivery vehicles using the disclosed donor cell lines are provided. As used herein, the term "delivery vehicle" refers for example, to any means that allows the transfer of a genetic circuit into a cell. In an embodiment, the delivery vehicle allows the transfer of a genetic circuit into a bacterial cell ("bacterial delivery vehicle"). In certain embodiments, the delivery vehicles are prepared by introducing the genetic circuit described herein into a suitable donor cell under conditions that permit formation of the delivery vehicles. For example, in certain embodiments, the method comprises (i) introducing into a donor cell the genetic circuit of interest; and (ii) allowing a sufficient amount of time for replication of the genetic circuit and packaging of the genetic circuit into the delivery vehicles. More particularly, the method of producing delivery vehicles may comprise (i) introducing into a donor cell as defined above, for example, a bacterial donor cell, comprising a genetic circuit of interest as defined above and prophage sequences encoding proteins required in trans for assembly of the genetic circuit into a delivery vehicle (e.g. bacteriophage scaffolding proteins); and (ii) allowing a sufficient amount of time for replication of the genetic circuit and packaging of the genetic circuit into the bacterial delivery vehicles. In one aspect, the method may further comprise the step of collection and, optionally, purification of the delivery vehicles.

In yet another aspect, donor cells are provided comprising a repressor protein expression cassette comprising sequences encoding repressor proteins. Donor cells may comprise a repressor protein expression cassette comprising a sequence encoding a repressor protein or several sequences encoding several repressor proteins. Further, in any of these embodiments, the donor cell may comprise prophage sequences encoding proteins required in trans for packaging of the nucleic acid payload of interest comprised in the genetic circuit (or the genetic circuit in its entirety) into a delivery vehicle. Such proteins include, for example, structural bacteriophage proteins, e.g., capsid proteins.

Methods are provided which enable transfer of a genetic circuit comprising a nucleic acid of interest encoding a protein or RNA molecule of interest, from a donor cell into a desired recipient or target cell. Genetic circuit and donor cell may be as defined above. In an embodiment, the target cell is a bacterial cell and does not express the repressor protein(s) found in the donor cell to negatively regulate the transcription of the nucleic acid of interest contained in the genetic circuit. Said methods may comprise contacting said donor cells with said recipient or target cells for a time sufficient for transfer of the genetic circuit. Alternatively, where bacterial delivery vehicles are produced (e.g. using a donor cell comprising a bacteriophage scaffold), the method may comprise contacting said recipient or target cells with the bacterial delivery vehicles produced in donor cells. The transferred genetic circuit comprises a nucleic acid of interest under the control of a repressor binding sequence that is negatively regulated by the donor cell expressed repressor protein. In such instances, transcription of the nucleic acid of interest encoding the protein or RNA molecule of interest is repressed through expression of a repressor protein in the donor cell. The methods provided herein enable transfer of a genetic circuit, comprising a nucleic acid encoding one or more proteins or RNA molecules of interest, into a desired target host cell which does not express, for example, naturally lacks, the repressor protein thereby allowing transcription of the payload of interest.

In certain embodiments, the nucleic acid of interest is selected from the group consisting of a nucleic acid encoding a RNA such as a mRNA, crRNA, tRNA, iRNA (interference RNA), asRNA (anti-sense RNA), ribozyme RNA, RNA aptamer or a guide RNA, a CRISPR locus, a toxin gene, a gene encoding an enzyme such as a nuclease or a kinase, a gene encoding a nuclease selected from the group consisting of a Cas nuclease, a Cas9 nuclease, a TALEN, a ZFN and a meganuclease, a gene encoding a recombinase, a bacterial receptor, a membrane protein, a structural protein or a secreted protein, a gene encoding resistance to an antibiotic or to a drug in general, a gene encoding a toxic protein or a toxic factor, and a gene encoding a virulence protein or a virulence factor, or any of their combination. The nucleic acid of interest may also encode a bacterial transporter or a bacterial pore or secretion system. Proteins encoded by the nucleic acid of interest can be modified or engineered to include extra features, like the addition or removal of a function (e.g. dCas9), the addition of a secretion signal to a protein not normally secreted or the addition of an exogenous peptide in a loop.

In an embodiment, the nucleic acid of interest encodes a therapeutic protein. In another embodiment, the nucleic acid of interest encodes an anti-sense nucleic acid molecule. In some embodiments, the nucleic acid of interest encodes two or more molecules of interest. In particular, one of these molecules may be a nuclease, for instance a Cas nuclease, and another molecule may be a nucleic acid molecule such as a guide RNA. In one aspect, the methods and compositions provided herein enable the transfer of a genetic circuit comprising a nucleic acid of interest that encodes a nuclease that targets cleavage of a host bacterial cell genome or a host bacterial cell plasmid. In some embodiments, the nuclease mediated cleavage occurs in an antibiotic resistant gene. In some other embodiments, the nuclease mediated cleavage of the host bacterial cell genome is designed to stimulate a homologous recombination event for insertion of a nucleic acid of interest into the genome of the bacterial cell.

Methods and compositions are provided which enable transfer of a genetic circuit comprising a nucleic acid of interest encoding a protein or RNA molecule of interest, into a desired target or recipient cell. As used herein, the term "transfer" refers to any means that allows the transfer of a genetic circuit into a recipient or target cell. Such means include, for example, transduction, conjugation and transformation. In some embodiments, delivery vehicles may be used to transfer genetic circuits from the donor cell to the target cell. Delivery vehicles encompassed by the present disclosure include, without limitation, bacteriophage scaffold, virus scaffold, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation). In preferred embodiments, delivery vehicles are bacteriophage scaffolds, i.e. obtained from natural, evolved or engineered capsids.

Any combination of delivery vehicles is also encompassed by the present disclosure. The delivery vehicle can refer to a bacteriophage derived scaffold and can be obtained from a natural, evolved or engineered capsid. In some embodiments, the delivery vehicle is the payload (e.g. genetic circuit) as bacteria are naturally competent to take up a payload from the environment on their own.

As used herein, the term "payload" refers to any one or more nucleic acid sequence, such as the genetic circuits disclosed herein, and/or amino acid sequence, or a combination of both (such as, without limitation, peptide nucleic acid or peptide-oligonucleotide conjugate) transferred into a recipient or target cell with a delivery vehicle. The term "payload" may also refer to a plasmid, a vector or a cargo. The payload can be a phagemid or phasmid obtained from natural, evolved or engineered bacteriophage genome. The payload can also be composed only in part of phagemid or phasmid obtained from natural, evolved or engineered bacteriophage genome.

As used herein, the term "nucleic acid" refers to a sequence of at least two nucleotides covalently linked together which can be single-stranded or double-stranded or contains portion of both single-stranded and double-stranded sequence. Nucleic acids as disclosed herein can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xathanine, hypoxathanine, isocytosine, 5-hydroxymethylcytosine and isoguanine. Other examples of modified bases that can be used are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphophoroamidite linkage and/or deoxyribonucleotides and ribonucleotides nucleic acids. Any combination of the above features of a nucleic acid is also encompassed by the present disclosure.

The genetic circuits may also comprise an origin of replication. Origins of replication, for use in the disclosed methods and compositions, are known in the art and have been identified from species-specific plasmid DNAs (e.g. ColE1, R1, pT181, pSC101, pMB1, R6K, RK2, p15a and the like), from bacterial virus (e.g. φX174, M13, F1 and P4)

and from bacterial chromosomal origins of replication (e.g. oriC). Such sequences permit, for example, replication of the genetic circuit in a bacterial cell, e.g. a donor cell and/or targeted cell. In one embodiment, a phagemid (genetic circuit) according to the disclosure comprises a bacterial origin of replication that is functional in a donor, target or recipient cell.

Alternatively, the genetic circuit according to the disclosure does not comprise any functional bacterial origin of replication or contains an origin of replication that is inactive in the targeted bacteria. Thus, the genetic circuit of the disclosure cannot replicate by itself once it has been introduced into a target or recipient cell.

In one embodiment, the origin of replication on the genetic circuit, or a plasmid to be packaged into a delivery vehicle, is inactive in the targeted bacteria, meaning that this origin of replication is not functional in the targeted cell, thus preventing unwanted plasmid replication.

In one embodiment, the genetic circuit or plasmid comprises a bacterial origin of replication that is functional in the donor bacteria cell, e.g in the donor bacteria cell used for the production of the bacterial virus particles.

Genetic circuit or plasmid replication depends on host enzymes and on genetic circuit or plasmid-controlled cis and trans determinants. For example, some genetic circuits or plasmids may have determinants that are recognized in almost all gram-negative bacteria and act correctly in each host during replication initiation and regulation. Other genetic circuits or plasmids may possess this ability only in some bacteria (Kues, U and Stahl, U 1989 Microbiol Rev 53:491-516).

Genetic circuits or plasmids may be replicated by three general mechanisms, namely theta type, strand displacement, and rolling circle (reviewed by Del Solar et al. 1998 Microhio and Molec Biol. Rev 62:434-464) that start at the origin of replication. These replication origins contain sites that are required for interactions of genetic circuit or plasmid and/or host encoded proteins.

Origins of replication used herein may be of moderate copy number, such as colEl ori from pBR322 (15-20 copies per cell) or the R6K plasmid (15-20 copies per cell) or may be high copy number, e.g. pUC oris (500-700 copies per cell), pGEM oris (300-400 copies per cell), pTZ oris (>1000 copies per cell) or pBluescript oris (300-500 copies per cell).

In one embodiment, the bacterial origin of replication comprised in the genetic circuit is selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5, pPS10, pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

In non-limiting embodiments, the bacterial origin of replication is a E. coli origin of replication selected in the group consisting of ColE1, pMB1 and variants (pBR322, pET, pUC, etc), p15a, ColA, ColE2, pOSAK, pSC101, R6K, IncW (pSa etc), IncFII, pT181, P1, F IncP, IncC, IncJ, IncN, IncP1, IncP4, IncQ, IncH11, RSF1010, CloDF13, NTP16, R1, f5 and pPS10.

In non-limiting embodiments, the bacterial origin of replication is selected in the group consisting of pC194, pE194, BBR1, pBC1, pEP2, pWVO1, pLF1311, pAP1, pWKS1, pLS1, pLS11, pUB6060, pJD4, pIJ101, pSN22, pAMbeta1, pIP501, pIP407, ZM6100(Sa), pCU1, RA3, pMOL98, RK2/RP4/RP1/R68, pB10, R300B, pRO1614, pRO1600, pECB2, pCM1, pFA3, RepFIA, RepFIB, RepFIC, pYVE439-80, R387, phasyl, RA1, TF-FC2, pMV158 and pUB113.

In a specific embodiment, the bacterial origin of replication are ColE1 and p15A.

The genetic circuit may comprise a phage replication origin. In particular, the delivered nucleic acid sequences according to the disclosure may comprise a phage replication origin which can initiate, with complementation of a complete phage genome, the replication of the delivered nucleic acid sequence for later encapsulation into the different capsids. A phage origin of replication can also be engineered to act as a bacterial origin of replication without the need to package any phage particles.

A phage origin of replication comprised in the genetic circuit or in the delivered nucleic acid sequence of the disclosure can be any origin of replication found in a phage.

In an embodiment, the phage origin of replication can be the wild-type or non-wildtype sequence of the M13, f1, φX174, P4, lambda, P2, 186, lambda-like, HK022, mEP237, HK97, HK629, HK630, mEP043, mEP213, mEP234, mEP390, mEP460, mEPx1, mEPx2, phi80, mEP234, T2, T4, T5, T7, RB49, phiX174, R17, PRD1 P1-like, P2-like, P22, P22-like, N15 and N15-like bacteriophages.

In an embodiment, the phage origin of replication is selected in the group consisting of phage origins of replication of M13, f1, φX174, P4, and lambda.

In a particular embodiment, the phage origin of replication is the lambda or P4 origin of replication.

The genetic circuit as disclosed herein comprises a nucleic acid sequence of interest under the transcriptional control of a repressor binding sequence. In the disclosed methods, transcription of the nucleic acid of interest is repressed in the donor cell while active in the targeted cell. In one embodiment, the nucleic acid of interest is a programmable nuclease circuit to be delivered to the targeted cell, i.e. the nucleic acid of interest encodes a programmable nuclease system to be delivered to the targeted cell. The programmable nuclease system comprises a programmable nuclease, i.e. a nuclease which is able to mediate sequence-specific elimination of a target gene of interest in the targeted cell. In particular, this programmable nuclease system may be able to mediate in vivo sequence-specific elimination of bacteria that contain a target gene of interest (e.g. a gene that is harmful to humans). Programmable nucleases which can be used in the methods disclosed herein include, for example, CRISPR nucleases (also named "CRISPR-associated proteins" or "Cas nucleases"), such as Type I, Type II CRISPR nucleases, TALEN nucleases, ZFN nucleases, meganucleases and recombinases and any variants thereof (evolved or engineered variants). These nucleases may be used separately or in combination, i.e. the programmable nuclease system may comprise one or several programmable nucleases. In a particular embodiment, the programmable nuclease is selected from engineered variants of the Type II CRISPR-Cas (Clustered Regularly Interspaced Short Palindromic Repeats-CRISPR-associated) system of Streptococcus pyogenes. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases. Depending on the type of nuclease used in the method, the programmable nuclease system may further comprise one or several additional components. In particular, when the programmable nuclease in a CRISPR nuclease, the programmable nuclease system further comprises, for example, a guide RNA to find and selectively cleave the targeted sequence. Thus, the engineered autonomously distributed nuclease circuits provided herein may be used to selectively cleave DNA encoding a gene of interest in the target cell such as, for example, a toxin gene, a virulence factor gene, an antibiotic resistance gene, a remodeling gene or a modulatory gene (cf. WO2014124226).

Other sequences of interest, for example, programmable sequences, can be included to the delivered nucleic acid sequence so as to be delivered to targeted cells. In an embodiment, the nucleic acid of interest encodes a molecule that affects the survival or the growth of the targeted cell, for example the target bacterium. In embodiments wherein the target cell is a bacterium, such a molecule may be chosen in order to lead to cell death (bactericidal effect) or to prevent the growth (bacteriostatic effect) of said bacterium. For example, the nucleic acid sequence of interest may encode holins, endolysins, restriction enzymes or toxins affecting the target cell, for example, affecting the survival or the growth of the target cell.

In a particular embodiment, the nucleic acid of interest encodes a bacteriocins. The bacteriocins can be a proteinaceous toxin produced by bacteria to kill or inhibit growth of other bacteria. Bacteriocins are categorized in several ways, including producing strain, common resistance mechanisms, and mechanism of killing. Such bacteriocins had been described from Gram negative bacteria (e.g. microcins, colicin-like bacteriocins and tailocins) and from Gram positive bacteria (e.g. Class I, Class II, Class III or Class IV bacteriocins). The nucleic acid of interest may also encode a transporter needed to secrete the toxin to the extracellular space.

In a more particular embodiment, the nucleic acid of interest comprises a sequence encoding a toxin selected in the group consisting of microcins, colicin-like bacteriocins, tailocins, Class I, Class II, Class III and Class IV bacteriocins.

In a particular embodiment, the corresponding immunity polypeptide (i.e. anti-toxin) may be used to protect bacterial cells (see review by Cotter et al., Nature Reviews Microbiology 11: 95, 2013, which is hereby incorporated by reference in its entirety) for delivered nucleic acid sequence production and encapsidation purpose but is absent in the pharmaceutical composition and in the targeted bacteria in which the nucleic acid of interest is delivered.

In some other embodiments, expression of the transferred nucleic acid of interest in the target cell does not lead to cell death. For example, the nucleic acid of interest may encode a reporter gene, e.g. leading to a luminescence or fluorescence signal.

In some other embodiments, the nucleic acid of interest may encode proteins, in particular enzymes, achieving a useful function in the target cell such as modifying the metabolism of the target cell, the composition of its environment or affecting the host comprising the target cell.

In a particular embodiment, the nucleic sequence of interest is selected in the group consisting of a nucleic acid encoding a RNA such as a mRNA, crRNA, tRNA, iRNA (interference RNA), asRNA (anti-sense RNA), ribozyme RNA, RNA aptamer or a guide RNA (gRNA), a CRISPR locus, a gene encoding an enzyme such as a nuclease or a kinase, a gene encoding a nuclease selected from the group consisting of a Cas nuclease, a Cas9 nuclease, a TALEN, a ZFN or a meganuclease, a gene encoding a recombinase, a bacterial receptor, a membrane protein, a structural protein, a secreted protein, or resistance to an antibiotic or to a drug in general, a gene a gene encoding a toxic protein or a toxic factor and a gene encoding a virulence protein, a virulence factor, a bacterial transporter or a bacterial pore, and any of their combinations. Proteins encoded by the nucleic acid of interest can also be modified or engineered to include extra features, like the addition or removal of a function (e.g. dCas9), the addition of a secretion signal to a protein not normally secreted, the addition of an exogenous peptide in a loop, etc . . . .

In some embodiments, the nucleic acid of interest encodes a CRISPR system. Typically, a CRISPR system contains two distinct elements, i.e. i) an endonuclease, in this case the CRISPR associated nuclease (Cas or "CRISPR associated protein") and ii) a guide RNA. The structure of the guide RNA may depend on the nature of the Cas nuclease. In particular, the guide RNA (gRNA ou sgRNA) may be in the form of a chimeric RNA which consists of the combination of a CRISPR (RNAcr) bacterial RNA and a RNAtracr (trans-activating RNA CRISPR) (Jinek et al., Science 2012). The gRNA combines the targeting specificity of the cRNA corresponding to the "spacing sequences" that serve as guides to the Cas proteins, and the conformational properties of the Rtracr in a single transcript. Such guide RNA is required for example when the Cas nuclease is Cas9. Alternatively, the guide RNA may only comprise a RNAcr. Such guide RNA is required for example when the Cas nuclease is Cpf1. When the gRNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix. In general, the CRISPR system includes two main classes depending on the nuclease mechanism of action. Class 1 is made of multi-subunit effector complexes and includes type I, III and IV. Class 2 is made of single-unit effector modules, like Cas9 nuclease, and includes type II (II-A, II-B, II-C, II-C variant), V (V-A, V-B, V-C, V-D, V-E, V-U1, V-U2, V-U3, V-U4, V-U5) and VI (VI-A, VI-B1, VI-B2, VI-C, VI-D).

The nucleic acid of interest according to the present disclosure may comprise a nucleic acid sequence encoding a Cas protein. A variety of CRISPR enzymes are available for use as a sequence of interest on the plasmid. In some embodiments, the CRISPR enzyme is a Type II CRISPR enzyme. In some embodiments, the CRISPR enzyme catalyzes DNA cleavage. In some other embodiments, the CRISPR enzyme catalyzes RNA cleavage. In one embodiment, the CRISPR enzyme may be coupled to a sgRNA. In certain embodiments, the sgRNA targets a gene selected in the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general or a gene causing a deleterious effect to the host (a host comprising the target cell).

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s).

The sequence encoding Cas9 (the entire protein or a fragment thereof) as used in the context of the disclosure can be obtained from any known Cas9 protein (Fonfara et al., Nucleic Acids Res 42 (4), 2014; Koonin et al., Nat Rev Microbiol 15(3), 2017). Examples of Cas9 proteins useful in the present disclosure include, but are not limited to, Cas9 proteins of *Streptococcus pyogenes* (SpCas9), *Streptococcus thermophiles* (St1Cas9, St3Cas9), *Streptococcus mutans, Staphylococcus aureus* (SaCas9), *Campylobacter jejuni* (cjCas9), *Francisella novicida* (FnCas9) and *Neisseria meningitides* (NmCas9).

In another particular embodiment, the CRISPR enzyme is any Cas12a, Cas13a or Cas13d protein, for instance any naturally-occurring bacterial Cas12a, Cas13a or Cas13d as well as any variants, homologs or orthologs thereof.

The sequence encoding Cpf1 (Cas12a) (the entire protein or a fragment thereof) as used in the context of the disclosure can be obtained from any known Cpf1 (Cas12a) protein (Koonin et al., 2017). Examples of Cpf1(Cas12a) proteins useful in the present disclosure include, but are not limited to, Cpf1(Cas12a) proteins of Acidaminococcus sp, Lachnospiraceae bacteriu and *Francisella novicida*.

The sequence encoding Cas13a (the entire protein or a fragment thereof) can be obtained from any known Cas13a (C2c2) protein (Abudayyeh et al., 2017). Examples of Cas13a (C2c2) proteins useful in the present disclosure include, but are not limited to, Cas13a (C2c2) proteins of *Leptotrichia wadei* (LwaCas13a).

The sequence encoding Cas13d (the entire protein or a fragment thereof) can be obtained from any known Cas13d protein (Yan et al., 2018). Examples of Cas13d proteins useful in the present disclosure include, but are not limited to, Cas13d proteins of *Eubacterium siraeum* and *Ruminococcus* sp.

In a particular embodiment, the nucleic acid of interest encodes a CRISPR/Cas system, such as a CRISPR/Cas9 system, for the reduction of gene expression or inactivation of a gene selected from the group consisting of an antibiotic resistance gene, virulence factor or protein gene, toxin factor or protein gene, a gene expressing a bacterial receptor, a membrane protein, a structural protein, a secreted protein, a gene expressing resistance to a drug in general or a gene causing a deleterious effect to the host.

In one embodiment, the CRISPR system is used to target and inactivate a virulence factor. A virulence factor can be any substance produced by a pathogen that alter host-pathogen interaction by increasing the degree of damage done to the host. Virulence factors are used by pathogens in many ways, including, for example, in cell adhesion or colonization of a niche in the host, to evade the host's immune response, to facilitate entry to and egress from host cells, to obtain nutrition from the host, or to inhibit other physiological processes in the host. Virulence factors can include enzymes, endotoxins, adhesion factors, motility factors, factors involved in complement evasion, and factors that promote biofilm formation. For example, such targeted virulence factor gene can be *E. coli* virulence factor gene such as, without limitation, EHEC-HlyA, Stx1 (VT1), Stx2 (VT2), Stx2a (VT2a), Stx2b (VT2b), Stx2c (VT2c), Stx2d (VT2d), Stx2e (VT2e) and Stx2f (VT2f), Stx2h (VT2h), stx2k, fimA, fimF, fimH, neuC, kpsE, sfa, foc, iroN, aer, iha, papC, papGI, papGII, papGIII, hlyC, cnfl, hra, sat, ireA, usp ompT, ibeA, malX, fyuA, irp2, traT, afaD, ipaH, eltB, estA, bfpA, eaeA, espA, aaiC, aatA, TEM, CTX, SHV, csgA, csgB, csgC, csgD, csgE, csgF, csgG, csgH, T1SS, T2SS, T3 SS, T4SS, T5SS, T6SS (secretion systems). For example, such targeted virulence factor gene can be *Shigella dysenteriae* virulence factor gene such as, without limitation, stx1 and stx2. For example, such targeted virulence factor gene can be *Yersinia pestis* virulence factor gene such as, without limitation, yscF (plasmid-borne (pCD1) T3SS external needle subunit). For example, such targeted virulence factor gene can be *Francisella tularensis* virulence factor gene such as, without limitation, fs1A. For example, such targeted virulence factor gene can be *Bacillus anthracis* virulence factor gene such as, without limitation, pag (Anthrax toxin, cell-binding protective antigen). For example, such targeted virulence factor gene can be *Vibrio cholera* virulence factor gene such as, without limitation, ctxA and ctxB (cholera toxin), tcpA (toxin co-regulated pilus), and toxT (master virulence regulator). For example, such targeted virulence factor gene can be *Pseudomonas aeruginosa* virulence factor genes such as, without limitation, pyoverdine (e.g., sigma factor pvdS, biosynthetic genes pvdL, pvdl, pvdJ, pvdH, pvdA, pvdF, pvdQ, pvdN, pvdM, pvdO, pvdP, transporter genes pvdE, pvdR, pvdT, opmQ), siderophore pyochelin (e.g., pchD, pchC, pchB, pchA, pchE, pchF and pchG, and toxins (e.g., exoU, exoS and exoT). For example, such targeted virulence factor gene can be *Klebsiella pneumoniae* virulence factor genes such as, without limitation, fimA (adherence, type I fimbriae major subunit), and cps (capsular polysaccharide). For example, such targeted virulence factor gene can be *Acinetobacter baumannii* virulence factor genes such as, without limitation, ptk (capsule polymerization) and epsA (assembly). For example, such targeted virulence factor gene can be *Salmonella enterica Typhi* virulence factor genes such as, without limitation, MIA (invasion, SPI-1 regulator), ssrB (SPI-2 regulator), and those associated with bile tolerance, including efflux pump genes acrA, acrB and tolC. For example, such targeted virulence factor gene can be *Fusobacterium nucleatum* virulence factor genes such as, without limitation, FadA and TIGIT. For example, such targeted virulence factor gene can be *Bacteroides fragilis* virulence factor genes such as, without limitation, bft.

In another embodiment, the CRISPR system, such as a CRISPR/Cas9 system, is used to target and inactivate an antibiotic resistance gene such as, without limitation, GyrB, ParE, ParY, AAC(1), AAC(2'), AAC(3), AAC(6'), ANT(2"), ANT(3"), ANT(4'), ANT(6), ANT(9), APH(2"), APH(3"), APH(3'), APH(4), APH(6), APH(7"), APH(9), ArmA, RmtA, RmtB, RmtC, Sgm, AER, BLA1, CTX-M, KPC, SHV, TEM, BlaB, CcrA, IMP, NDM, VIM, ACT, AmpC, CMY, LAT, PDC, OXA β-lactamase, mecA, Omp36, OmpF, PIB, bla (blaI, blaR1) and mec (mecI, mecR1) operons, Chloramphenicol acetyltransferase (CAT), Chloramphenicol phosphotransferase, Ethambutol-resistant arabinosyltransferase (EmbB), MupA, MupB, Integral membrane protein MprF, Cfr 23S rRNA methyltransferase, Rifampin ADP-ribosyltransferase (Arr), Rifampin glycosyltransferase, Rifampin monooxygenase, Rifampin phosphotransferase, DnaA, RbpA, Rifampin-resistant beta-subunit of RNA polymerase (RpoB), Erm 23S rRNA methyltransferases, Lsa, MsrA, Vga, VgaB, Streptogramin Vgb lyase, Vat acetyltransferase, Fluoroquinolone acetyltransferase, Fluoroquinolone-resistant DNA topoisomerases, Fluoroquinolone-resistant GyrA, GyrB, ParC, Quinolone resistance protein (Qnr), FomA, FomB, FosC, FosA, FosB, FosX, VanA, VanB, VanD, VanR, VanS, Lincosamide nucleotidyltransferase (Lin), EreA, EreB, GimA, Mgt, Ole, Macrolide phosphotransferases (MPH), MefA, MefE, Mel, Streptothricin acetyltransferase (sat), Sul1, Su12, Su13, sulfonamide-resistant FolP, Tetracycline inactivation enzyme TetX, TetA, TetB, TetC, Tet30, Tet31, TetM, TetO, TetQ, Tet32, Tet36, MacAB-TolC, MsbA, MsrA, VgaB, EmrD, EmrAB-TolC, NorB, GepA, MepA, AdeABC, AcrD, MexAB-OprM, mtrCDE, EmrE, adeR, acrR, baeSR, mexR, phoPQ, mtrR, or any antibiotic resistance gene described in the Comprehensive Antibiotic Resistance Database (CARD https://card.mcmaster.ca/).

In another embodiment, the CRISPR system, such as a CRISPR/Cas9 system, is used to target and inactivate a bacterial toxin gene. Bacterial toxin can be classified as either exotoxins or endotoxins. Exotoxins are generated and actively secreted; endotoxins remain part of the bacteria. The response to a bacterial toxin can involve severe inflammation and can lead to sepsis. Such toxin can be for example Botulinum neurotoxin, Tetanus toxin, Staphylococcus toxins, Diptheria toxin, Anthrax toxin, Alpha toxin, Pertussis toxin, Shiga toxin, Heat-stable enterotoxin (*E. coli* ST), colibactin, BFT (*B. fragilis* toxin) or any toxin described in Henkel et al., (Toxins from Bacteria in EXS. 2010; 100: 1-29).

The terms "donor cell", "target cell" and "recipient cell" as used herein refers, for example, to prokaryotic cells, such as bacterial cells. In particular, the "donor", "target" or "recipient" cells disclosed herein can be any bacteria present or that can be present in a mammal organism. It can be any commensal, symbiotic or pathogenic bacteria of the microbiota or microbiome.

A microbiome may comprise of a variety of endogenous bacterial species, any of which may be targeted in accordance with the present disclosure. In some embodiments, where bacterial delivery vehicles are used, the genus and/or species of targeted endogenous bacterial cells may depend on the type of bacteriophages being used for preparing the bacterial delivery vehicles. For example, some bacteriophages exhibit tropism for, or preferentially target, specific host species of bacteria. Other bacteriophages do not exhibit such tropism and may be used to target a number of different genus and/or species of endogenous bacterial cells.

Examples of bacterial cells that can be used as donor cells or target cells include, without limitation, cells from bacteria of the genus *Yersinia* spp., *Escherichia* spp., *Klebsiella* spp., *Acinetobacter* spp., *Bordetella* spp., *Neisseria* spp., *Aeromonas* spp., Franciesella spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., *Erysipelothrix* spp., *Salmonella* spp., *Streptomyces* spp., *Streptococcus* spp., *Staphylococcus* spp., *Bacteroides* spp., *Prevotella* spp., *Clostridium* spp., *Bifidobacterium* spp., *Clostridium* spp., *Brevibacterium* spp., *Lactococcus* spp., *Leuconostoc* spp., *Actinobacillus* spp., *Selnomonas* spp., *Shigella* spp., *Zymonas* spp., *Mycoplasma* spp., *Treponema* spp., *Leuconostoc* spp., *Corynebacterium* spp., *Enterococcus* spp., *Enterobacter* spp., *Pyrococcus* spp., *Serratia* spp., *Morganella* spp., *Parvimonas* spp., *Fusobacterium* spp., *Actinomyces* spp., *Porphyromonas* spp., *Micrococcus* spp., *Bartonella* spp., *Borrelia* spp., *Brucelia* spp., *Campylobacter* spp., *Chlamydophilia* spp., *Cutibacterium* spp., *Propionibacterium* spp., *Gardnerella* spp., *Ehrlichia* spp., *Haemophilus* spp., *Leptospira* spp., *Listeria* spp., *Mycoplasma* spp., *Nocardia* spp., *Rickettsia* spp., *Ureaplasma* spp., and *Lactobacillus* spp, and a mixture thereof.

In an embodiment, the bacteria can be selected from the group consisting of *Yersinia* spp., *Escherichia* spp., *Klebsiella* spp., *Acinetobacter* spp., *Pseudomonas* spp., *Helicobacter* spp., *Vibrio* spp, *Salmonella* spp., *Streptococcus* spp., *Staphylococcus* spp., *Bacteroides* spp., *Clostridium* spp., *Shigella* spp., *Enterococcus* spp., *Enterobacter* spp., *Listeria* spp., *Cutibacterium* spp., *Propionibacterium* spp., *Fusobacterium* spp., *Porphyromonas* spp. And *Gardnerella* spp.

In some embodiments, bacterial cells of the present disclosure that can be used as donor cells or target cells are anaerobic bacterial cells (e.g., cells that do not require oxygen for growth). Anaerobic bacterial cells include facultative anaerobic cells such as but not limited to *Escherichia coli, Shewanella oneidensis, Gardnerella vaginalis* and *Listeria*. Anaerobic bacterial cells also include obligate anaerobic cells such as, for example, *Bacteroides, Clostridium, Cutibacterium, Propionibacterium, Fusobacterium* and Porphyromona species. In humans, anaerobic bacteria are most commonly found in the gastrointestinal tract. In some particular embodiments, the targeted bacteria (target cells) are thus bacteria most commonly found in the gastrointestinal tract. Bacterial delivery vehicles, such as for example bacteriophages used for preparing the bacterial virus particles, and then the bacterial virus particles, may target (e.g., to specifically target) anaerobic bacterial cells according to their specific spectra known by the person skilled in the art to specifically deliver the plasmid.

In some embodiments, the bacterial cells that can be used as donor cells or target cells are, without limitation, *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphilococcus lugdunensis, Leuconostoc oenos, Corynebacterium xerosis, Lactobacillus plantarum, Lactobacillus rhamnosus, Lactobacillus casei, Lactobacillus acidophilus, Enterococcus faecalis, Bacillus coagulans, Bacillus cereus, Bacillus popillae, Synechocystis* strain PCC6803, *Bacillus liquefaciens, Pyrococcus abyssi, Selenomonas nominantium, Lactobacillus hilgardii, Streptococcus fetus, Lactobacillus pentosus, Bacteroides fragilis, Staphylococcus epidermidis, Streptomyces phaechromogenes, Streptomyces ghanaenis, Klebsiella pneumoniae, Enterobacter cloacae, Enterobacter aerogenes, Serratia marcescens, Morganella morganii, Citrobacter freundii, Propionibacterium freudenreichii, Pseudomonas aerigunosa, Parvimonas micra, Prevotella intermedia, Fuso-* bacterium nucleatum, Prevotella nigrescens, Actinomyces israelii, Porphyromonas endodontalis, Porphyromonas gingivalis Micrococcus luteus, Bacillus megaterium, Aeromonas hydrophila, Aeromonas caviae, Bacillus anthracis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Campylobacter coli, Campylobacter fetus, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Cutibacterium acnes (formerly Propionibacterium acnes), Ehrlichia canis, Ehrlichia chaffeensis, Enterococcus faecium, Francisella tularensis, Haemophilus influenza, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumonia, Neisseria gonorrhoeae, Neisseria meningitides, Nocardia asteroids, Rickettsia rickettsia, Salmonella enteritidis, Salmonella typhi, Salmonella paratyphi, Salmonella typhimurium, Shigella flexnerii, Shigella dysenteriae, Staphylococcus saprophyticus, Streptococcus pneumoniae, Streptococcus pyogenes, Gardnerella vaginalis, Streptococcus viridans, Treponema pallidum, Ureaplasma urealyticum, Vibrio cholera, Vibrio parahaemolyticus, Yersinia pestis, Yersinia enterocolitica, Yersinia pseudotuberculosis, Actinobacter baumanii, Pseudomonas aerigunosa, and a mixture thereof. In an embodiment, the bacterial cells that can be used as donor cells or target cells are selected from the group consisting of *Escherichia coli, Enterococcus faecium, Staphylococcus aureus, Klebsiella pneumoniae, Acinetobacter baumanii, Pseudomonas aeruginosa, Enterobacter cloacae*, and *Enterobacter aerogenes*, and a mixture thereof.

In one embodiment, the bacteria that can be used as donor cells or target cells are *Escherichia coli*.

In one embodiment, the bacteria that can be used as donor cells or target cells are pathogenic bacteria. The bacteria can be virulent bacteria.

The bacteria that can be used as donor cells or target cells can be antibacterial resistance bacteria, such as those selected from the group consisting of extended-spectrum beta-lactamase-producing (ESBL) *Escherichia coli*, ESBL *Klebsiella pneumoniae*, vancomycin-resistant *Enterococcus* (VRE), methicillin-resistant *Staphylococcus aureus* (MRSA), multidrug-resistant (MDR) *Acinetobacter baumannii*, MDR *Enterobacter* spp., and a combination thereof. In an embodiment, the bacteria can be selected from the group consisting of extended-spectrum beta-lactamase-producing (ESBL) *Escherichia coli* strains.

In some particular embodiments, the donor cell and/or the target cell is a probiotic. As used herein, the term "probiotic" includes, but is not limited to, bacterlactobacilli, bifidobacteria, streptococci, enterococci, propionibacteria, saccaromycetes, lactobacilli, bifidobacteria, or proteobacteria.

Alternatively, the bacterium that can be used as donor cell or target cell can be a bacterium of the microbiome of a given species, such as a bacterium of the human microbiota.

In some embodiments, the donor cell and the target cell are phylogenetically close, for example, of the same phylum, class, order, family, genus or species. In an embodiment, the donor cell and the target cell are of the same genus or species.

In certain embodiments, the present disclosure is directed to methods for transfer of a genetic circuit from a donor cell into a target or recipient cell through the production of bacterial delivery vehicles containing the genetic circuit as described herein. The bacterial delivery vehicles can be prepared from bacterial virus. The bacterial delivery vehicles are chosen in order to be able to introduce the genetic circuit into the targeted bacterial cell. The bacterial delivery vehicles may be engineered to target specific bacteria (see, for example, Serial Application Nos. 62/771,761; 62/802,777; and 62/783,258 each of which is incorporated herein in their entirety).

In an embodiment, bacterial viruses, from which the bacterial delivery vehicles may be derived, are bacteriophages. Optionally, the bacteriophage is selected from the Order Caudovirales consisting of, based on the taxonomy of Krupovic et al, Arch Virol, 2015:

Bacteriophages may be selected from the family Myoviridae (such as, without limitation, genus Cp220virus, Cp8virus, Ea214virus, Felixolvirus, Mooglevirus, Suspvirus, Hp1virus, P2virus, Kayvirus, P100virus, Silviavirus, Spolvirus, Tsarbombavirus, Twortvirus, Cc31virus, Jd18virus, Js98virus, Kp15virus, Moonvirus, Rb49virus, Rb69virus, S16virus, Schizot4virus, Sp18virus, T4virus, Cr3virus, Selvirus, V5virus, Abouovirus, Agatevirus, Agrican357virus, Ap22virus, Arv1virus, B4virus, Bastillevirus, Bc431virus, Bcep78virus, Bcepmuvirus, Biquartavirus, Bxzlvirus, Cd119virus, Cp5lvirus, Cvm10virus, Eah2virus, Elvirus, Hapunavirus, Jimmervirus, Kpp10virus, M12virus, Machinavirus, Marthavirus, Msw3virus, Muvirus, Myohalovirus, Nit1virus, P1virus, Pakpunavirus, Pbunavirus, Phikzvirus, Rheph4virus, Rs12virus, Rslunavirus, Secunda5virus, Sep1virus, Spn3virus, Svunavirus, Tg1virus, Vhm1virus and Wphvirus).

Bacteriophages may be selected from the family Podoviridae (such as, without limitation, genus Fri1virus, Kp32virus, Kp34virus, Phikmvvirus, Pradovirus, Sp6virus, T7virus, Cp1virus, P68virus, Phi29virus, Nona33virus, Pocjvirus, Tl2011virus, Bcep22virus, Bpp1virus, Cba41virus, Dfl12virus, Ea92virus, Epsilon15virus, F116virus, G7cvirus, Jwalphavirus, Kf1virus, Kpp25virus, Lit1virus, Luz24virus, Luz7virus, N4virus, Nonanavirus, P22virus, Pagevirus, Phieco32virus, Prtbvirus, Sp58virus, Una961virus and Vp5virus)

Bacteriophages may be selected from the family Sipho-viridae (such as, without limitation, genus Camvirus, Likavirus, R4virus, Acadianvirus, Coopervirus, Pg1virus, Pipe-fishvirus, Rosebushvirus, Brujitavirus, Che9cvirus, Hawkeyevirus, Plotvirus, Jerseyvirus, K1gvirus, Sp31virus, Lmd1virus, Una4virus, Bongovirus, Reyvirus, Buttersvirus, Charlievirus, Redivirus, Baxtervirus, Nymphadoravirus, Bignuzvirus, Fishburnevirus, Phayoncevirus, Kp36virus, Roguelvirus, Rtpvirus, T1virus, T1svirus, Ab18virus, Amigovirus, Anatolevirus, Andromedavirus, Attisvirus, Barnyardvirus, Bernal13virus, Biseptimavirus, Bronvirus, C2virus, C5virus, Cba181virus, Cbastvirus, Cecivirus, Che8virus, Chivirus, Cjwlvirus, Corndogvirus, Cronusvirus, D3112virus, D3virus, Decurrovirus, Demosthenesvirus, Doucettevirus, E125virus, Eiauvirus, Ff47virus, Gaiavirus, Gilesvirus, Gordonvirus, Gordtnkvirus, Harrisonvirus, Hk578virus, Hk97virus, Jenstvirus, Jwxvirus, Kelleziovirus, Korravirus, L5virus, lambdavirus, Laroyevirus, Liefievirus, Marvinvirus, Mudcatvirus, N15virus, Nonagvirus, Np1virus, Omegavirus, P12002virus, P12024virus, P23virus, P70virus, Pa6virus, Pamx74virus, Patiencevirus, Pbi1virus, Pepy6virus, Pfr1virus, Phic31virus, Phicbkvirus, Phietavirus, Phifelvirus, Phijl1virus, Pis4avirus, Psavirus, Psimunavirus, Rdj1virus, Rer2virus, Sap6virus, Send513virus, Septima3virus, Seuratvirus, Sextaecvirus, Sfi11virus, Sfi21dt1virus, Sitaravirus, Sk1virus, Slashvirus, Smoothievirus, Soupsvirus, Spbetavirus, Ssp2virus, T5virus, Tankvirus, Tin2virus, Titanvirus, Tm4virus, Tp21virus, Tp84virus, Triavirus, Trigintaduovirus, Vegasvirus, Vendettavirus, Wbetavirus, Wildcatvirus, Wizardvirus, Woesvirus, Xp10virus, Ydn12virus and Yuavirus).

Bacteriophages may be selected from the family Ackermannviridae (such as, without limitation, genus Ag3virus, Limestonevirus, Cba120virus and Vi1virus).

Optionally, the bacteriophage is not part of the order Caudovirales but from families with unassigned order such as, without limitation, family Tectiviridae (such as genus Alphatectivirus, Betatectivirus), family Corticoviridae (such as genus Corticovirus), family Inoviridae (such as genus Fibrovirus, Habenivirus, Inovirus, Lineavirus, Plectrovirus, Saetivirus, Vespertiliovirus), family Cystoviridae (such as genus Cystovirus), family Leviviridae (such as genus Allolevivirus, Levivirus), family Microviridae (such as genus Alpha3microvirus, G4microvirus, Phix174microvirus, Bdellomicrovirus, Chlamydiamicrovirus, Spiromicrovirus) and family Plasmaviridae (such as genus Plasmavirus).

Optionally, the bacteriophage is targeting Archea not part of the Order Caudovirales but from families with Unassigned order such as, without limitation, Ampullaviridae, FuselloViridae, Globuloviridae, Guttaviridae, Lipothrixviridae, Pleolipoviridae, Rudiviridae, Salterprovirus and Bicaudaviridae.

A non-exhaustive listing of bacterial genera and their known host-specific bacteria viruses is presented in the following paragraphs. The bacterial delivery vehicles disclosed herein may be engineered, as non-limiting examples, from the following phages. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Actinomyces* can be infected by the following phages: Av-I, Av-2, Av-3, BF307, CT1, CT2, CT3, CT4, CT6, CT7, CT8 and 1281.

Bacteria of the genus *Aeromonas* can be infected by the following phages: AA-I, Aeh2, N, PM1, TP446, 3, 4, 11, 13, 29, 31, 32, 37, 43, 43-10T, 51, 54, 55R.1, 56, 56RR2, 57, 58, 59.1, 60, 63, Aeh1, F, PM2, 1, 25, 31, 40RR2.8t, (syn=44R), (syn=44RR2.8t), 65, PM3, PM4, PM5 and PM6.

Bacteria of the genus *Bacillus* can be infected by the following phages: A, aiz1, A1-K-I, B, BCJA1, BC1, BC2, BLL1, BL1, BP142, BSL1, BSL2, BS1, BS3, BS8, BS15, BS18, BS22, BS26, BS28, BS31, BS104, BS105, BS106, BTB, B1715V1, C, CK-I, Co11, Cor1, CP-53, CS-I, Csi, D, D, D, D5, ent1, FP8, FP9, Fsi, FS2, FS3, FS5, FS8, FS9, G, GH8, GT8, GV-I, GV-2, GT-4, g3, g12, g13, g14, g16, g17, g21, g23, g24, g29, H2, ken1, KK-88, Kum1, Kyu1, J7W-1, LP52, (syn=LP-52), L7, Mex1, MJ-I, mor2, MP-7, Mp1O, MP12, MP14, MP15, Neol, N° 2, N5, N6P, PBC1, PBLA, PBP1, P2, S-a, SF2, SF6, Sha1, Si11, SP02, (syn=ΦSPP1), SPfβ, STI, Sti, SU-I1, t, TbI, Tb2, Tb5, TbIO, Tb26, Tb51, Tb53, Tb55, Tb77, Tb97, Tb99, Tb560, Tb595, Td8, Td6, Td15, TgI, Tg4, Tg6, Tg7, Tg9, TgIO, TgI1, Tg13, Tg15, Tg21, Tin1, Tin7, Tin8, Tin13, Tm3, Toc1, Tog1, to11, TP-I, TP-10vir, TP-15c, TP-16c, TP-17c, TP-19, TP35, TP51, TP-84, Tt4, Tt6, type A, type B, type C, type D, type E, Tφ3, VA-9, W, wx23, wx26, Yun1, α, γ, p11, φmed-2, φT, φμ-4, φ3T, φ75, φ1O5, (syn=φ1O5), IA, IB, 1-97A, 1-97B, 2, 2, 3, 3, 3, 5, 12, 14, 20, 30, 35, 36, 37, 38, 41C, 51, 63, 64, 138D, I, II, IV, NN-*Bacillus* (13), alel, Arl, AR2, AR3, AR7, AR9, Bace-11, (syn=11), Bastille, BL1, BL2, BL3, BL4, BL5, BL6, BL8, BL9, BP124, BS28, BS80, Ch, CP-51, CP-54, D-5, dar1, den1, DP-7, ent1, FoSi, FoS2, FS4, FS6, FS7, G, ga11, gamma, Gel, GF-2, Gsi, GT-I, GT-2, GT-3, GT-4, GT-5, GT-6, GT-7, GV-6, g15, 19, 110, Isi, K, MP9, MP13, MP21, MP23, MP24, MP28, MP29, MP30, MP32, MP34, MP36, MP37, MP39, MP40, MP41, MP43, MP44, MP45, MP47, MP50, NLP-I, No. 1, N17, N19, PBS1, PK1, PMB1, PMB12, PMJ1, S, SPO1, SP3, SP5, SP6, SP7, SP8, SP9, Sp10, SP-15, SP50, (syn=SP-50), SP82, SST, sub1, SW, Tg8, Tg12, Tg13, Tg14, thu1, thuΛ, thuS, Tin4, Tin23, TP-13, TP33, TP50, TSP-I, type V, type VI, V, Vx, β22, φe, φNR2, φ25, φ63, 1, 1, 2, 2C, 3NT, 4, 5, 6, 7, 8, 9, 10, 12, 12, 17, 18, 19, 21, 138, III, 4 (*B. megateriwn*), 4 (*B. sphaericus*), AR13, BPP-IO, BS32, BS107, B1, B2, GA-I, GP-IO, GV-3, GV-5, g8, MP20, MP27, MP49, Nf, PPS, PP6, SF5, Tg18, TP-I, Versailles, φ15, φ29, 1-97, 837/IV, mt-*Bacillus* (1), Bat1O, BSL1O, BSLI 1, BS6, BSI 1, BS16, BS23, Bs1O1, BS102, g18, mor1, PBL1, SN45, thu2, thu3, TmI, Tm2, TP-20, TP21, TP52, type F, type G, type IV, HN-BacMus (3), BLE, (syn=θc), BS2, BS4, BS5, BS7, B1O, B12, BS20, BS21, F, MJ-4, PBA12, AP50, AP50-04, AP50-11, AP50-23, AP50-26, AP50-27 and Bam35. The following *Bacillus*-specific phages are defective: DLP10716, DLP-11946, DPB5, DPB12, DPB21, DPB22, DPB23, GA-2, M, No. IM, PBLB, PBSH, PBSV, PBSW, PBSX, PBSY, PBSZ, phi, Spa, type 1 and μ.

Bacteria of the genus *Bacteroides* can be infected by the following phages: crAss-phage, ad I2, Baf-44, Baf-48B, Baf-64, Bf-I, Bf-52, B40-8, F1, β1, φA1, φBrO1, φBrO2, 11, 67.1, 67.3, 68.1, mt-*Bacteroides* (3), Bf42, Bf71, HN-Bdellovibrio (1) and BF-41.

Bacteria of the genus *Bordetella* can be infected by the following phages: 134 and NN-*Bordetella* (3).

Bacteria of the genus *Borrelia* can be infected by the following phages: NN-*Borrelia* (1) and NN-*Borrelia* (2).

Bacteria of the genus *Brucella* can be infected by the following phages: A422, Bk, (syn=Berkeley), BM29, Foi, (syn=Fo1), (syn=FQ1), D, FP2, (syn=FP2), (syn=FD2), Fz, (syn=Fz75/13), (syn=Firenze 75/13), (syn=Fi), Fi, (syn=F1), Fim, (syn=Fim), (syn=Fim), FiU, (syn=F1U), (syn=FiU), F2, (syn=F2), F3, (syn=F3), F4, (syn=F4), F5, (syn=F5), F6, F7, (syn=F7), F25, (syn=F25), (syn=£25), F25U, (syn=F25u), (syn=F25U), (syn=F25V), F44, (syn-F44), F45, (syn=F45), F48, (syn=F48), I, Im, M, MC/75, M51, (syn=M85), P, (syn=D), 5708, R, Tb, (syn=TB), (syn=Tbilisi), W, (syn=Wb), (syn=Weybridge), X, 3, 6, 7, 10/1, (syn=10), (syn=F8), (syn=F8), 12m, 24/11, (syn=24), (syn=F9), (syn=F9), 45/111, (syn=45), 75, 84, 212/XV, (syn=212), (syn=Fi0), (syn=F10), 371/XXIX, (syn=371), (syn=Fn), (syn=F1 1) and 513.

Bacteria of the genus *Burkholderia* can be infected by the following phages: CP75, NN-*Burkholderia* (1) and 42.

Bacteria of the genus *Campylobacter* can be infected by the following phages: C type, NTCC12669, NTCC12670, NTCC12671, NTCC12672, NTCC12673, NTCC12674, NTCC12675, NTCC12676, NTCC12677, NTCC12678, NTCC12679, NTCC12680, NTCC12681, NTCC12682, NTCC12683, NTCC12684, 32f, 111c, 191, NN-*Campylobacter* (2), Vfi-6, (syn=V19), VfV-3, V2, V3, V8, V16, (syn=Vfi-1), V19, V20(V45), V45, (syn=V-45) and NN-*Campylobacter* (1).

Bacteria of the genus *Chlamydia* can be infected by the following phage: Chp1.

Bacteria of the genus *Clostridium* can be infected by the following phages: CAK1, CA5, Ca7, Ceβ, (syn=1C), Ceγ, Cld1, c-n71, c-203 Tox-, Deβ, (syn=ID), (syn=1Dt0X+), HM3, KM1, KT, Ms, Nal, (syn=Naltox+), PA135Oe, Pfó, PL73, PL78, PL81, P1, P50, P5771, P19402, 1CtOX+, 2CtOX\ 2D3 (syn=2DtOX+), 3C, (syn=3Ct0x+), 4C, (syn=4CtOX+), 56, III-1, NN-*Clostridium* (61), NB1t0X+, α1, Ca1, HMT, HM2, PF15 P-23, P-46, Q-05, Q-oe, Q-16, Q-21, Q-26, Q-40, Q-46, 5111, SA02, WA01, WA03, Wm, W523, 80, C, CA2, CA3, CPT1, CPT4, c1, c4, c5, HM7, H11/A1, H18/Ax, FWS23, Hi58ZA1, K2ZA1, K21ZS23, ML, NA2t0X; Pf2, Pf3, Pf4, S9ZS3, S41ZA1, S44ZS23, α2, 41, 112ZS23, 214/S23, 233/Ai, 234/S23, 235/S23, II-1, 11-2, 11-3, NN-*Clostridium* (12), Cal, F1, K, S2, 1, 5 and NN-*Clostridium* (8).

Bacteria of the genus *Corynebacterium* can be infected by the following phages: CGK1 (defective), A, A2, A3, A101, A128, A133, A137, A139, A155, A182, B, BF, B17, B18, B51, B271, B275, B276, B277, B279, B282, C, capi, CC1, CG1, CG2, CG33, CL31, Cog, (syn=CGS), D, E, F, H, H-I, hqi, hq2, 11ZH33, Ii/31, J, K, K, (syn=Ktox"), L, L, (syn=Ltox+), M, MC-I, MC-2, MC-3, MC-4, MLMa, N, O, ovi, ov2, ov3, P, P, R, RP6, RS29, S, T, U, UB1, ub2, UH1, UH3, uh3, uh5, uh6, β, (syn=βtox+), βhv64, βvir, γ, (syn=γtoχ-), γ19, δ, (syn=δ'ox+), p, (syn=ptoχ-), Φ9, φ984, ω, IA, 1/1180, 2, 2/1180, 5/1180, 5ad/9717, 7/4465, 8/4465, 8ad/10269, 10/9253, 13Z9253, 15/3148, 21/9253, 28, 29, 55, 2747, 2893, 4498 and 5848.

Bacteria of the genus *Enterococcus* are infected by the following phages: DF78, F1, F2, 1, 2, 4, 14, 41, 867, D1, SB24, 2BV, 182, 225, C2, C2F, E3, E62, DS96, H24, M35, P3, P9, Sb1O1, S2, 2BII, 5, 182a, 705, 873, 881, 940, 1051, 1057, 21096C, NN-*Enterococcus* (1), Pe1, F1, F3, F4, VD13, 1, 200, 235 and 341.

Bacteria of the genus *Erysipelothrix* can be infected by the following phage: NN-*Erysipelothrix* (1).

Bacteria of the genus *Escherichia* can be infected by the following phages: BW73, B278, D6, D108, E, E1, E24, E41, FI-2, FI-4, FI-5, HI8A, Ffl8B, i, MM, Mu, (syn=mu), (syn=MuI), (syn=Mu-I), (syn=MU-I), (syn=MuI), (syn=μ), 025, PhI-5, Pk, PSP3, P1, P1D, P2, P4 (defective), S1, Wφ, φK13, φR73 (defective), φ1, φ2, φ7, φ92, ψ (defective), 7 A, 8φ, 9φ, 15 (defective), 18, 28-1, 186, 299, HH-*Escherichia* (2), AB48, CM, C4, C16, DD-VI, (syn=Dd-Vi), (syn=DDVI), (syn=DDVi), E4, E7, E28, f11, FI3, H, H1, H3, H8, K3, M, N, ND-2, ND-3, ND4, ND-5, ND6, ND-7, Ox-I (syn=° X1), (syn=HF), Ox-2 (syn=0x2), (syn=0X2), Ox-3, Ox-4, Ox-5, (syn=0X5), Ox-6, (syn=66F), (syn=φ66t), (syn=φ66t–)5 0111, PhI-I, RB42, RB43, RB49, RB69, S, SaI-I, Sal-2, Sal-3, Sal-4, Sal-5, Sal-6, TC23, TC45, TuII*-6, (syn=TuII*), TuIP-24, TuII*46, TuIP-60, T2, (syn=ganuTia), (syn=γ), (syn=PC), (syn=P.C.), (syn=T-2), (syn=T2), (syn=P4), T4, (syn=T-4), (syn=T4), T6, T35, α1, 1, IA, 3, (syn=Ac3), 3A, 3T+, (syn=3), (syn=M1), 5φ, (syn=φ5), 9266Q, CFO103, HK620, J, K, K1F, m59, no. A, no. E, no. 3, no. 9, N4, sd, (syn=Sd), (syn=SD), (syn=Sa)3 (syn=sd), (syn=SD), (syn=CD), T3, (syn=T-3), (syn=T3), T7, (syn=T-7), (syn=T7), WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11 (syn=φW), Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, eC1, EC2, E21, E29, F1, F26S, F27S, Hi, HK022, HK97, (syn=ΦK97), HK139, HK253, HK256, K7, ND-I, no.D, PA-2, q, S2, T1, (syn=α), (syn=P28), (syn=T-I), (syn=Tx), T3C, T5, (syn=T-5), (syn=T5), UC-I, w, β4, γ2, λ(syn=lambda), (syn=Φλ), ΦD326, φγ, Φ06, Φ07, Φ10, φ80, χ, (syn=χi), (syn=φχ), (syn=φχi), 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-J, 933H, O157 typing phages 1 to 16, JES-2013, 121Q, 172-1, 1720a-02, ADB-2, AKVF33, av-05, bV_EcoS_AHP42, bV_EcoS_AHP24, bC_EcoS_AHS24, bV_EcoS_AKS96 and CBA120.

Bacteria of the genus *Fusobacterium* are infected by the following phages: NN-*Fusobacterium* (2), fv83-554/3, fv88-531/2, 227, fv2377, fv2527 and fv8501.

Bacteria of the genus *Haemophilus* are infected by the following phages: HP1, S2 and N3.

Bacteria of the genus *Helicobacter* are infected by the following phages: HP1 and ^^ *Helicobacter* (1).

Bacteria of the genus *Klebsiella* are infected by the following phages: AIO-2, KI4B, K16B, K19, (syn=K19), K114, K115, K121, K128, K129, KI32, K133, K135, K1106B, K1171B, K1181B, K1832B, AIO-I, AO-I, AO-2, AO-3, FC3-10, K, K11, (syn=kI1), K12, (syn=K12), K13, (syn=K13), (syn=K170/11), K14, (syn=K14), K15, (syn=K15), K16, (syn=K16), K17, (syn=K17), K18, (syn=K18), K119, (syn=K19), K127, (syn=K127), K131, (syn=K131), K135, K1171B, II, VI, IX, CI-I, K14B, K18, K111, K112, K113, K116, K117, K118, K120, K122, K123, K124, K126, K130, K134, K1106B, kli65B, K1328B, KLXI, K328, P5046, 11, 380, III, IV, VII, VIII, FC3-11, K12B, (syn=K12B), K125, (syn=K125), K142B, (syn=K142), (syn=K142B), K1181B, (syn=kI1 81), (syn=K1181B), K1765/!, (syn=K1765/1), K1842B, (syn=K1832B), K1937B, (syn=K1937B), L1, φ28, 7, 231, 483, 490, 632 and 864/100.

Bacteria of the genus *Leptospira* are infected by the following phages: 1E1, LE3, LE4 and ~NN-*Leptospira* (1).

Bacteria of the genus *Listeria* are infected by the following phages: A511, 01761, 4211, 4286, (syn=BO54), A005, A006, A020, A500, A502, A511, A1 18, A620, A640, B012, B021, B024, B025, B035, B051, B053, B054, B055, B056, B1O1, B11O, B545, B604, B653, C707, D441, HSO47, H1OG, H8/73, H19, H21, H43, H46, H107, H108, HI10, H163/84, H312, H340, H387, H391/73, H684/74, H924A, PSA, U153, φMLUP5, (syn=P35), 00241, 00611, 02971A, 02971C, 5/476, 5/911, 5/939, 5/11302, 5/11605, 5/11704, 184, 575, 633, 699/694, 744, 900, 1090, 1317, 1444, 1652, 1806, 1807, 1921/959, 1921/11367, 1921/11500, 1921/11566, 1921/12460, 1921/12582, 1967, 2389, 2425, 2671, 2685, 3274, 3550, 3551, 3552, 4276, 4277, 4292, 4477, 5337, 5348/11363, 5348/11646, 5348/12430, 5348/12434, 10072, 11355C, 11711A, 12029, 12981, 13441, 90666, 90816, 93253, 907515, 910716 and NN-*Listeria* (15).

Bacteria of the genus *Morganella* are infected by the following phage: 47.

Bacteria of the genus *Mycobacterium* are infected by the following phages: 13, aGl, aLi, ATCC 11759, A2, B.C3, BG2, BK1, BKS, *butyricum*, B-I, B5, B7, B30, B35, Clark, C1, C2, DNAIII, DSP1, D4, D29, GS4E, (syn=GS4E), GS7, (syn=GS-7), (syn=GS7), iPa, lacticola, Legendre, Leo, L5, (syn=ΦL-5), MC-I, MC-3, MC-4, minetti, MTPHI 1, Mx4, MyF3P/59a, phlei, (syn=phlei 1), phlei 4, Polonus II, rabinovitschi, *smegmatis*, TM4, TM9, tM1O, TM20, Y7, Y1O, φ630, IB, IF, IH, 1/1, 67, 106, 1430, B1, (syn=Bo1), B24, D, D29, F—K, F—S, HP, Polonus I, Roy, R1, (syn=R1-Myb), (syn=Ri), 11, 31, 40, 50, 103a, 103b, 128, 3111-D, 3215-D and NN-*Mycobacterium* (1).

Bacteria of the genus *Neisseria* are infected by the following phages: Group I, group II and NP1.

Bacteria of the genus *Nocardia* are infected by the following phages: MNP8, NJ-L, NS-8, N5 and TtiN-*Nocardia*.

Bacteria of the genus *Proteus* are infected by the following phages: Pm5, 13vir, 2/44, 4/545, 6/1004, 13/807, 20/826, 57, 67b, 78, 107/69, 121, 9/0, 22/608, 30/680, PmI, Pm3, Pm4, Pm6, Pm7, Pm9, PmIO, PmI 1, Pv2, π1, φm, 7/549, 9B/2, 10A/31, 12/55, 14, 15, 16/789, 17/971, 19A/653, 23/532, 25/909, 26/219, 27/953, 32A/909, 33/971, 34/13, 65, 5006M, 7480b, VI, 13/3a, Clichy 12, n2600, φχ7, 1/1004, 5/742, 9, 12, 14, 22, 24/860, 2600/D52, Pm8 and 24/2514.

Bacteria of the genus *Providencia* are infected by the following phages: PL25, PL26, PL37, 9211/9295, 9213/921 Ib, 9248, 7/R49, 7476/322, 7478/325, 7479, 7480, 9000/9402 and 9213/921 Ia.

Bacteria of the genus *Pseudomonas* are infected by the following phages: PfI, (syn=Pf-I), Pf2, Pf3, PP7, PRR1, 7s, im-*Pseudomonas* (1), AI-I, AI-2, B 17, B89, CB3, Col 2, Col 11, Col 18, Col 21, C154, C163, C167, C2121, E79, F8, ga, gb, H22, K1, M4, N2, Nu, PB-I, (syn=PB1), pf16, PMN17, PP1, PP8, Psa1, PsP1, PsP2, PsP3, PsP4, PsP5, PS3, PS17, PTB80, PX4, PX7, PYO1, PYO2, PYO5, PYO6, PYO9, PYO10, PYO13, PYO14, PYO16, PYO18, PYO19, PYO20, PYO29, PYO32, PYO33, PYO35, PYO36, PYO37, PYO38, PYO39, PYO41, PYO42, PYO45, PYO47, PYO48, PYO64, PYO69, PYO103, P1K, SLP1, SL2, S2, UNL-I, wy, Yai, Ya4, Yan, φBE, φCTX, φC17, φKZ, (syn=ΦKZ), φ-LT, Φmu78, φNZ, φPLS-1, φST-1, φW-14, φ-2, 1/72, 2/79, 3, 3/DO, 4/237, 5/406, 6C, 6/6660, 7, 7v, 7/184, 8/280, 9/95, 10/502, 11/DE, 12/100, 12S, 16, 21, 24, 25F, 27, 31, 44, 68, 71, 95, 109, 188, 337, 352, 1214, HN-*Pseudomonas* (23), A856, B26, CI-I, CI-2, C5, D, gh-1, F1 16, HF, H90, K5, K6, K1 04, K109, K166, K267, N4, N5, 06N-25P, PE69, Pf, PPN25, PPN35, PPN89, PPN91, PP2, PP3, PP4, PP6, PP7, PP8, PP56, PP87, PP1 14, PP206, PP207, PP306, PP651, Psp231a, Pssy401, Pssy9220, psi, PTB2, PTB20, PTB42, PX1, PX3, pX1O, PX12, PX14, PYO70, PYO71, R, SH6, SH133, tf, Ya5, Ya7, φBS, ΦKf77, φ-MC, ΦmnF82, φPLS27, φPLS743, φS-1, 1, 2, 2, 3, 4, 5, 6, 7, 7, 8, 9, 10, 11, 12, 12B, 13, 14, 15, 14, 15, 16, 17, 18, 19, 20, 20, 21, 21, 22, 23, 23, 24, 25, 31, 53, 73, 119x, 145, 147, 170, 267, 284, 308, 525, NN-*Pseudomonas* (5), af, A7, B3, B33, B39, BI-I, C22, D3, D37, D40, D62, D3112, F7, F1O, g, gd, ge, gξ Hw12, Jb 19, KF1, L°, OXN-32P, O6N-52P, PCH-I, PC13-1, PC35-1, PH2, PH51, PH93, PH132, PMW, PM13, PM57, PM61, PM62, PM63, PM69, PM105, PM1 13, PM681, PM682, PO4, PP1, PP4, PP5, PP64, PP65, PP66, PP71, PP86, PP88, PP92, PP401, PP711, PP891, Pssy41, Pssy42, Pssy403, Pssy404, Pssy420, Pssy923, PS4, PS-IO, Pz, SD1, SL1, SL3, SL5, SM, φC5, φC1 1, φC1 1-1, φC13, φC15, φMO, φX, φO4, φ1 1, φ240, 2, 2F, 5, 7m, 11, 13, 13/441, 14, 20, 24, 40, 45, 49, 61, 73, 148, 160, 198, 218, 222, 236, 242, 246, 249, 258, 269, 295, 297, 309, 318, 342, 350, 351, 357-1, 400-1, HN-*Pseudomonas* (6), G101, M6, M6a, L1, PB2, Pssy15, Pssy4210, Pssy4220, PYO12, PYO34, PYO49, PYO50, PYO51, PYO52, PYO53, PYO57, PYO59, PYO200, PX2, PX5, SL4, φO3, φO6 and 1214.

Bacteria of the genus *Rickettsia* are infected by the following phage: NN-*Rickettsia*.

Bacteria of the genus *Salmonella* are infected by the following phages: b, Beccles, CT, d, Dundee, f, FeIs 2, GI, GUI, GVI, GVIII, k, K, i, j, L, 01, (syn=0-1), (syn=O1), (syn=O-I), (syn=7), 02, 03, P3, P9a, P1O, Sab3, Sab5, San1S, San17, SI, Taunton, ViI, (syn=ViI), 9, imSalmonella (1), N—I, N-5, N-IO, N-17, N-22, 11, 12, 16-19, 20.2, 36, 449C/C178, 966A/C259, a, B.A.O.R., e, G4, GUI, L, LP7, M, MG40, N-18, PSA68, P4, P9c, P22, (syn=P22), (syn=PLT22), (syn=PLT22), P22al, P22-4, P22-7, P22-11, SNT-I, SNT-2, SP6, Villi, ViIV, ViV, ViVI, ViVII, Worksop, Sj5, ε34, 1, 37, 1(40), (syn=φ1[40]), 1, 422, 2, 2.5, 3b, 4, 5, 6, 14(18), 8, 14(6,7), 10, 27, 28B, 30, 31, 32, 33, 34, 36, 37, 39, 1412, SNT-3, 7-11, 40.3, c, C236, C557, C625, C966N, g, GV, G5, G173, h, IRA, Jersey, MB78, P22-1, P22-3, P22-12, Sab1, Sab2, Sab2, Sab4, San1, San2, San3, San4, San6, San7, San8, San9, San13, San14, San16, San18, San19, San20, San21, San22, San23, San24, San25, San26, SasL1, SasL2, SasL3, SasL4, SasL5, S1BL, SII, ViII, φ1, 1, 2, 3a, 3a1, 1010, Ym-*Salmonella* (1), N-4, SasL6 and 27.

Bacteria of the genus *Serratia* are infected by the following phages: A2P, PS20, SMB3, SMP, SMP5, SM2, V40, V56, ic, ΦCP-3, ΦCP-6, 3M, 10/la, 20A, 34CC, 34H, 38T, 345G, 345P, 501B, SMB2, SMP2, BC, BT, CW2, CW3, CW4, CW5, Lt232, L2232, L34, L.228, SLP, SMPA, V.43, σ, φCW1, ΦCP6-1, ΦCP6-2, ΦCP6-5, 3T, 5, 8, 9F, 10/1, 20E, 32/6, 34B, 34CT, 34P, 37, 41, 56, 56D, 56P, 6OP, 61/6, 74/6, 76/4, 101/8900, 226, 227, 228, 229F, 286, 289, 290F, 512, 764a, 2847/10, 2847/1Oa, L.359 and SMB1.

Bacteria of the genus *Shigella* are infected by the following phages: Fsa, (syn=a), FSD2d, (syn=D2d), (syn=W2d), FSD2E, (syn=W2e), fv, F6, f7.8, H-Sh, PES, P90, SfII, Sh, SHm, SHrv, (syn=HIV), sHvi, (syn=HVI), SHVvm, (syn=HVIII), SKγ66, (syn=gamma 66), (syn=yββ), (syn=γ66b), SKm, (syn=SIIIb)5 (syn=UI), SKw, (syn=Siva), (syn=IV), SIC™, (syn=SIVA.), (syn=IVA), sKvi, (syn=KVI), (syn=Svi), (syn=VI), SKvm, (syn=Svm), (syn=VIII), SKIIIA, (syn=SvmA), (syn=VIIIA), sTvi, STK, STx1, STxn, S66, W2, (syn=D2c), (syn=D20), φ1, φIVb 3-SO-R, 8368-SO-R, F7, (syn=FS7), (syn=K29), F1O, (syn=fS1O), (syn=K31), I1, (syn=alfa), (syn=fSa), (syn=K1 8), (syn=α), 12, (syn=a), (syn=K19), SG33, (syn=G35), (syn=SO-35/G), SG35, (syn=SO-55/G), SG3201, (syn=SO-3201/G), SHn, (syn=HII), SHv, (syn=SHV), SHx, SHX, SKn, (syn=K2), (syn=KII), (syn=Sn), (syn=SsII), (syn=II), SKrv, (syn=Sm), (syn=SsIV), (syn=IV), SK1Va, (syn=Swab), (syn=SsIVa), (syn=iVa), SKV, (syn=K4), (syn=KV), (syn=SV), (syn=SsV), (syn=V), SKx, (syn=K9), (syn=KX), (syn=SX), (syn=SsX), (syn=X), STV, (syn=T35), (syn=35-50-R), STvm, (syn=T8345), (syn=8345-SO-S-R), W1, (syn=D8), (syn=FSD8), W2a, (syn=D2A), (syn=FS2a), DD-2, Sf6, fSi, (syn=F1), SF6, (syn=F6), SG42, (syn=SO-42/G), SG3203, (syn=SO-3203/G), SKF12, (syn=SsF12), (syn=F12), (syn=F12), STn, (syn=1881-SO-R), γ66, (syn=gamma 66a), (syn=Ssγ66), φ2, bII, DDVII, (syn=DD7), FSD2b, (syn=W2B), FS2, (syn=F2), (syn=F2), FS4, (syn=F4), (syn=F4), FS5, (syn=F5), (syn=F5), FS9, (syn=F9), (syn=F9), FI1, P2-SO-S, SG36, (syn=SO-36/G), (syn=G36), SG3204, (syn=SO-3204/G), SG3244, (syn=SO-3244/G), sHi, (syn=HI), SHvπ, (syn=HVII), SHK, (syn=HIX), SHx1, SHxπ, (syn=HXn), SKI, KI, (syn=S1), (syn=SsI), SKVII, (syn=KVII), (syn=Svπ), (syn=SsVII), SKIX, (syn=KIX), (syn=S1x), (syn=SsIX), SKXII, (syn=KXII), (syn=Sxn), (syn=SsXII), sTi, STff1, STrv, STVi, STvπ, S70, S206, U2-S0-S, 3210-SO-S, 3859-SO-S, 4020-SO-S, φ3, φ5, φ7, φ8, φ9, φ1O, φ1 1, φ13, φ14, φ18, SHm, (syn=Hπi), sHχi, (syn=HXt) and sKxI, (syn=KXI), (syn=Sχi), (syn=SsXI), (syn=XI).

Bacteria of the genus *Staphylococcus* are infected by the following phages: A, EW, K, Ph5, Ph9, PhIO, Ph13, P1, P2, P3, P4, P8, P9, P1O, RG, SB-i, (syn=Sb-I), S3K, Twort, ΦSK311, φ812, 06, 40, 58, 119, 130, 131, 200, 1623, STC1, (syn=stc1), STC2, (syn=stc2), 44AHJD, 68, aC1, AC2, A6"C", A9"C", b581, CA-I, CA-2, CA-3, CA-4, CA-5, DI1, L39x35, L54a, M42, N1, N2, N3, N4, N5, N7, N8, N1O, Ni 1, N12, N13, N14, N16, Ph6, Ph12, Ph14, UC-18, U4, U15, S1, S2, S3, S4, S5, X2, Z1, φB5-2, φD, ω, 11, (syn=φ1 1), (syn=P11-M15), 15, 28, 28A, 29, 31, 31B, 37, 42D, (syn=P42D), 44A, 48, 51, 52, 52A, (syn=P52A), 52B, 53, 55, 69, 71, (syn=P71), 71A, 72, 75, 76, 77, 79, 80, 80a, 82, 82A, 83 A, 84, 85, 86, 88, 88A, 89, 90, 92, 95, 96, 102, 107, 108, 111, 129-26, 130, 130A, 155, 157, 157A, 165, 187, 275, 275A, 275B, 356, 456, 459, 471, 471A, 489, 581, 676, 898, 1139, 1154A, 1259, 1314, 1380, 1405, 1563, 2148, 2638A, 2638B, 2638C, 2731, 2792A, 2792B, 2818, 2835, 2848A, 3619, 5841, 12100, AC3, A8, A1O, A13, b594n, D, HK2, N9, N15, P52, P87, S1, S6, Z4, φRE, 3A, 3B, 3C, 6, 7, 16, 21, 42B, 42C, 42E, 44, 47, 47A5 47C, 51, 54, 54x1, 70, 73, 75, 78, 81, 82, 88, 93, 94, 101, 105, 110, 115, 129/16, 174, 594n, 1363/14, 2460 and mS-*Staphylococcus* (1).

Bacteria of the genus *Streptococcus* are infected by the following phages: EJ-I, NN-Streptococais (1), a, C1, FL0Ths, H39, Cp-I, Cρ-5, Cp-7, Cp-9, Cp-IO, AT298, A5, a1O/J1, a1O/J2, a1O/J5, a1O/J9, A25, BTI1, b6, cA1, c20-1, c20-2, DP-I, Dp-4, DT1, ET42, e1O, FA101, FETHs,FK, FKKIOI, FKLIO, FKP74, FKH, FLOTHs, FyIO1, f1, F10, F20140/76, g, GT-234, HB3, (syn=HB-3), HB-623, HB-746, M102, O1205, φO1205, PST, PO, P1, P2, P3, P5, P6, P8, P9, P9, P12, P13, P14, P49, P50, P51, P52, P53, P54, P55, P56, P57, P58, P59, P64, P67, P69, P71, P73, P75, P76, P77, P82, P83, P88, sc, sch, sf, Sfl1 1, (syn=sFiI 1), (syn=φSFill), (syn=φSfi1 1), (syn=φSfi1 1), sfi19, (syn=sFi19), (syn=(pSFi19), (syn=φSfi19), Sfi21, (syn=sFi21), (syn=φSFi21), (syn=φSfi21), ST0, STX, st2, ST2, ST4, S3, (syn=φS3), s265, Φ17, φ42, Φ57, φ80, φ81, φ82, φ83, φ84, φ85, φ86, φ87, φ88, φ89, φ90, φ91, φ92, φ93, φ94, φ95, φ96, φ97, φ98, φ99, φ1OO, φ1O1, φ1O2, φ227, Φ7201, ω1, ω2, ω3, ω4, ω5, ω6, ω8, ω1O, 1, 6, 9, 1OF, 12/12, 14, 17SR, 19S, 24, 50/33, 50/34, 55/14, 55/15, 70/35, 70/36, 71/ST15, 71/45, 71/46, 74F, 79/37, 79/38, 80/J4, 80/J9, 80/ST16, 80/15, 80/47, 80/48, 101, 103/39, 103/40, 121/41, 121/42, 123/43, 123/44, 124/44, 337/ST17 and mStreptococcus (34).

Bacteria of the genus *Treponema* are infected by the following phage: NN-*Treponema* (1).

Bacteria of the genus *Vibrio* are infected by the following phages: CTXΦ, fs, (syn=si), fs2, Ivpf5, Vfl2, Vf33, VPIΦ, VSK, v6, 493, CP-T1, ET25, kappa, K139, Labol)XN-69P, OXN-86, O6N-21P, PB-I, P147, rp-1, SE3, VA-I, (syn=VcA-I), VcA-2, VP1, VP2, VP4, VP7, VP8, VP9, vP1O, VP17, VP18, VP19, X29, (syn=29 d'Herelle), t, ΦHAWI-1, ΦHAWI-2, ΦHAWI-3, ΦHAWI-4, ΦHAWI-5, ΦHAWI-6, ΦHAWI-7, XHAWI-8, ΦHAWI-9, ΦHAWI-10, ΦHC1-1, ΦHC1-2, ΦHC1-3, ΦHC1-4, ΦHC2-1, >HC2-2, ΦHC2-3,ΦHC2-4, ΦHC3-1, ΦHC3-2, ΦHC3- 3, ΦHD1S-1, ΦHD1S-2, ΦHD2S-1, ΦHD2S-2, ΦHD2S-3, ΦHD2S-4, ΦHD2S-5, ΦHDO-1, ΦHDO-2, ΦHDO-3, ΦHDO-4, ΦHDO-5, ΦHDO-6, ΦKL-33, ΦKL-34, ΦKL-35, ΦKL-36, ΦKWH-2, ΦKWH-3, ΦKWH-4, ΦMARQ-1, ΦMARQ-2, ΦMARQ-3, ΦMOAT-1, ΦO139, ΦPEL1A-1, ΦPEL1A-2, ΦPEL8A-1, ΦPEL8A-2, ΦPEL8A-3, ΦPEL8C-1, ΦPEL8C-2, ΦPEL13A-1, ΦPEL13B-1, ΦPEL13B-2, ΦPEL13B-3, ΦPEL13B-4, ΦPEL13B-5, ΦPEL13B-6, ΦPEL13B-7, ΦPEL13B-8, ΦPEL13B-9, ΦPEL13B-10, φVP143, φVP253, Φ16, φ138, 1-II, 5, 13, 14, 16, 24, 32, 493, 6214, 7050, 7227, II, (syn=group II), (syn=φ2), V, VIII, ~m-*Vibrio* (13), KVP20, KVP40, nt-1, O6N-22P, P68, e1, e2, e3, e4, e5, FK, G, I, K, nt-6, N1, N2, N3, N4, N5, O6N-34P, OXN-72P, OXN-85P, OXN-100P, P, Ph-I, PL163/10, Q, S, T, φ92, 1-9, 37, 51, 57, 70A-8, 72A-4, 72A-10, 110A-4, 333, 4996, I (syn=group I), III (syn=group III), VI, (syn=A-Saratov), VII, IX, X, HN-*Vibrio* (6), pA1, 7, 7-8, 70A-2, 71A-6, 72A-5, 72A-8, 108A-10, 109A-6, 109A-8, 1 1OA-1, 110A-5, 110A-7, hv-1, OXN-52P, P13, P38, P53, P65, P108, Pi11, TP13 VP3, VP6, VP12, VP13, 70A-3, 70A-4, 70A-10, 72A-1, 108A-3, 109-B1, 110A-2, 149, (syn=φ149), IV, (syn=group IV), NN-*Vibrio* (22), VPS, VPI1, VP15, VP16, α1, α2, α3a, α3b, 353B and HN-*Vibrio* (7).

Bacteria of the genus *Yersinia* are infected by the following phages: H, H-1, H-2, H-3, H-4, Lucas 110, Lucas 303, Lucas 404, YerA3, YerA7, YerA20, YerA41, 3/M64-76, 5/G394-76, 6/C753-76, 8/C239-76, 9/F18167, 1701, 1710, PST, 1/F2852-76, D'Herelle, EV, H, Kotljarova, PTB, R, Y, YerA41, φYerO3-12, 3, 4/C1324-76, 7/F783-76, 903, 1/M6176 and Yer2AT.

In an embodiment, the bacteriophage used as bacterial delivery vehicle is selected in the group consisting of *Salmonella* virus SKML39, *Shigella* virus AG3, *Dickeya* virus Limestone, *Dickeya* virus RC2014, *Escherichia* virus CBA120, *Escherichia* virus PhaxI, *Salmonella* virus 38, *Salmonella* virus Det7, *Salmonella* virus GG32, *Salmonella* virus PM10, *Salmonella* virus SFP10, *Salmonella* virus SH19, *Salmonella* virus SJ3, *Escherichia* virus ECML4, *Salmonella* virus Marshall, *Salmonella* virus Maynard, *Salmonella* virus SJ2, *Salmonella* virus STML131, *Salmonella* virus Vil, *Erwinia* virus Ea2809, *Klebsiella* virus 0507KN21, *Serratia* virus IME250, *Serratia* virus MAM1, *Campylobacter* virus CP21, *Campylobacter* virus CP220, *Campylobacter* virus CPt10, *Campylobacter* virus IBB35, *Campylobacter* virus CP81, *Campylobacter* virus CP30A, *Campylobacter* virus CPX, *Campylobacter* virus NCTC12673, *Erwinia* virus Ea214, *Erwinia* virus M7, *Escherichia* virus AYO145A, *Escherichia* virus EC6, *Escherichia* virus HY02, *Escherichia* virus JH2, *Escherichia* virus TP1, *Escherichia* virus VpaE1, *Escherichia* virus wV8, *Salmonella* virus FelixO1, *Salmonella* virus HB2014, *Salmonella* virus Mushroom, *Salmonella* virus UAB87, *Citrobacter* virus Moogle, *Citrobacter* virus Mordin, *Escherichia* virus SUSP1, *Escherichia* virus SUSP2, *Aeromonas* virus phiO18P, *Haemophilus* virus HP1, *Haemophilus* virus HP2, *Pasteurella* virus F108, *Vibrio* virus K139, *Vibrio* virus Kappa, *Burkholderia* virus phi52237, *Burkholderia* virus phiE122, *Burkholderia* virus phiE202, *Escherichia* virus 186, *Escherichia* virus P4, *Escherichia* virus P2, *Escherichia* virus Wphi, *Mannheimia* virus PHL101, *Pseudomonas* virus phiCTX, *Ralstonia* virus RSA1, *Salmonella* virus Fels2, *Salmonella* virus PsP3, *Salmonella* virus SopEphi, *Yersinia* virus L413C, *Staphylococcus* virus G1, *Staphylococcus* virus G15, *Staphylococcus* virus JD7, *Staphylococcus* virus K, *Staphylococcus* virus MCE2014, *Staphylococcus* virus P108, *Staphylococcus* virus Rodi, *Staphylococcus* virus 5253, *Staphylococcus* virus S25-4, *Staphylococcus* virus SA12, *Listeria* virus A511, *Listeria* virus P100, *Staphylococcus* virus Remus, *Staphylococcus* virus SA11, *Staphylococcus* virus Stau2, *Bacillus* virus Camphawk, *Bacillus* virus SPO1, *Bacillus* virus BCP78, *Bacillus* virus TsarBomba, *Staphylococcus* virus Twort, *Enterococcus* virus phiEC24C, *Lactobacillus* virus Lb338-1, *Lactobacillus* virus LP65, *Enterobacter* virus PG7, *Escherichia* virus CC31, *Klebsiella* virus JD18, *Klebsiella* virus PKO111, *Escherichia* virus Bp7, *Escherichia* virus IME08, *Escherichia* virus JS10, *Escherichia* virus JS98, *Escherichia* virus QL01, *Escherichia* virus VR5, *Enterobacter* virus Eap3, *Klebsiella* virus KP15, *Klebsiella* virus KP27, *Klebsiella* virus Matisse, *Klebsiella* virus Miro, *Citrobacter* virus Merlin, *Citrobacter* virus Moon, *Escherichia* virus JSE, *Escherichia* virus phi1, *Escherichia* virus RB49, *Escherichia* virus HX01, *Escherichia* virus JS09, *Escherichia* virus RB69, *Shigella* virus UTAM, *Salmonella* virus S16, *Salmonella* virus STML198, *Vibrio* virus KVP40, *Vibrio* virus nt1, *Vibrio* virus ValKK3, *Escherichia* virus VR7, *Escherichia* virus VR20, *Escherichia* virus VR25, *Escherichia* virus VR26, *Shigella* virus SP18, *Escherichia* virus AR1, *Escherichia* virus C40, *Escherichia* virus E112, *Escherichia* virus ECML134, *Escherichia* virus HY01, *Escherichia* virus Ime09, *Escherichia* virus RB3, *Escherichia* virus RB14, *Escherichia* virus T4, *Shigella* virus Pss1, *Shigella* virus Shfl2, *Yersinia* virus D1, *Yersinia* virus PST, *Acinetobacter* virus 133, *Aeromonas* virus 65, *Aeromonas* virus Aeh1, *Escherichia* virus RB16, *Escherichia* virus RB32, *Escherichia* virus RB43, *Pseudomonas* virus 42, Cronobacter virus CR3, Cronobacter virus CR8, Cronobacter virus CR9, Cronobacter virus PBES02, *Pectobacterium* virus phiTE, Cronobacter virus GAP31, *Escherichia* virus 4MG, *Salmonella* virus SE1, *Salmonella* virus SSE121, *Escherichia* virus FFH2, *Escherichia* virus FV3, *Escherichia* virus JES2013, *Escherichia* virus V5, *Brevibacillus* virus Abouo, *Brevibacillus* virus Davies, *Bacillus* virus Agate, *Bacillus* virus Bobb, *Bacillus* virus Bp8pC, *Erwinia* virus Deimos, *Erwinia* virus Ea35-70, *Erwinia* virus RAY, *Erwinia* virus Simmy50, *Erwinia* virus SpecialG, *Acinetobacter* virus AB1, *Acinetobacter* virus AB2, *Acinetobacter* virus AbC62, *Acinetobacter* virus AP22, *Arthrobacter* virus ArV1, *Arthrobacter* virus Trina, *Bacillus* virus AvesoBmore, *Bacillus* virus B4, *Bacillus* virus Bigbertha, *Bacillus* virus Riley, *Bacillus* virus Spock, *Bacillus* virus Troll, *Bacillus* virus Bastille, *Bacillus* virus CAM003, *Bacillus* virus Bc431, *Bacillus* virus Bcp1, *Bacillus* virus BCP82, *Bacillus* virus BM15, *Bacillus* virus Deepblue, *Bacillus* virus JBP901, *Burkholderia* virus Bcep1, *Burkholderia* virus Bcep43, *Burkholderia* virus Bcep781, *Burkholderia* virus BcepNY3, *Xanthomonas* virus OP2, *Burkholderia* virus BcepMu, *Burkholderia* virus phiE255, *Aeromonas* virus 44RR2, *Mycobacterium* virus Alice, *Mycobacterium* virus Bxz1, *Mycobacterium* virus Dandelion, *Mycobacterium* virus HyRo, *Mycobacterium* virus I3, *Mycobacterium* virus Nappy, *Mycobacterium* virus Sebata, *Clostridium* virus phiC2, *Clostridium* virus phiCD27, *Clostridium* virus phiCD119, *Bacillus* virus CP51, *Bacillus* virus JL, *Bacillus* virus Shanette, *Escherichia* virus CVM10, *Escherichia* virus ep3, *Erwinia* virus Asesino, *Erwinia* virus EaH2, *Pseudomonas* virus EL, *Halomonas* virus HAP1, *Vibrio* virus VP882, *Brevibacillus* virus Jimmer, *Brevibacillus* virus Osiris, *Pseudomonas* virus Ab03, *Pseudomonas* virus KPP10, *Pseudomonas* virus PAKP3, *Sinorhizobium* virus M7, *Sinorhizobium* virus M12, *Sinorhizobium* virus N3, *Erwinia* virus Machina, *Arthrobacter* virus Brent, *Arthrobacter* virus Jawnski, *Arthrobacter* virus Martha, *Arthrobacter* virus Sonny, Edwardsiella virus MSW3, edwardsiella virus PEi21, *Escherichia* virus Mu, *Shigella* virus SfMu, *Halobacterium* virus phiH, *Bacillus* virus Grass, *Bacillus* virus NIT1, *Bacillus* virus SPG24, *Aeromonas* virus 43, *Escherichia* virus P1, *Pseudomonas* virus CAb1, *Pseudomonas* virus CAb02, *Pseudomonas* virus JG004, *Pseudomonas* virus PAKP1, *Pseudomonas* virus PAKP4, *Pseudomonas* virus PaP1, *Burkholderia* virus BcepF1, *Pseudomonas* virus 141, *Pseudomonas* virus Ab28, *Pseudomonas* virus DL60, *Pseudomonas* virus DL68, *Pseudomonas* virus F8, *Pseudomonas* virus JG024, *Pseudomonas* virus KPP12, *Pseudomonas* virus LBL3, *Pseudomonas* virus LMA2, *Pseudomonas* virus PB1, *Pseudomonas* virus SN, *Pseudomonas* virus PA7, *Pseudomonas* virus phiKZ, *Rhizobium* virus RHEph4, *Ralstonia* virus RSF1, *Ralstonia* virus RSL2, *Ralstonia* virus RSL1, *Aeromonas* virus 25, *Aeromonas* virus 31, *Aeromonas* virus Aes12, *Aeromonas* virus Aes508, *Aeromonas* virus AS4, *Stenotrophomonas* virus IME13, *Staphylococcus* virus IPLAC1C, *Staphylococcus* virus SEP1, *Salmonella* virus SPN3US, *Bacillus* virus 1, *Geobacillus* virus GBSV1, *Yersinia* virus R1RT, *Yersinia* virus TG1, *Bacillus* virus G, *Bacillus* virus PBS1, *Microcystis* virus Ma-LMM01, *Vibrio* virus MAR, *Vibrio* virus VHML, *Vibrio* virus VP585, *Bacillus* virus BPS13, *Bacillus* virus Hakuna, *Bacillus* virus Megatron, *Bacillus* virus WPh, *Acinetobacter* virus AB3, *Acinetobacter* virus Abp 1, *Acinetobacter* virus Fri1, *Acinetobacter* virus IME200, *Acinetobacter* virus PD6A3, *Acinetobacter* virus PDAB9, *Acinetobacter* virus phiAB1, *Escherichia* virus K30, *Klebsiella* virus K5, *Klebsiella* virus K11, *Klebsiella* virus Kp1, *Klebsiella* virus KP32, *Klebsiella* virus KpV289, *Klebsiella* virus F19, *Klebsiella* virus K244, *Klebsiella* virus Kp2, *Klebsiella* virus KP34, *Klebsiella* virus KpV41, *Klebsiella* virus KpV71, *Klebsiella* virus KpV475, *Klebsiella* virus SU503, *Klebsiella* virus SU552A, *Pantoea* virus Limelight, *Pantoea* virus Limezero, *Pseudomonas* virus LKA1, *Pseudomonas* virus phiKMV, *Xanthomonas* virus f20, *Xanthomonas* virus f30, *Xylella* virus Prado, *Erwinia* virus Era103, *Escherichia* virus K5, *Escherichia* virus K1-5, *Escherichia* virus K1E, *Salmonella* virus SP6, *Escherichia* virus T7, *Kluyvera* virus Kvp1, *Pseudomonas* virus ghl, Prochlorococcus virus PSSP7, *Synechococcus* virus P60, *Synechococcus* virus Syn5, *Streptococcus* virus Cp1, *Streptococcus* virus Cp1, *Staphylococcus* virus 44AHJD, *Streptococcus* virus C1, *Bacillus* virus B103, *Bacillus* virus GA1, *Bacillus* virus phi29, *Kurthia* virus 6, *Actinomyces* virus Av1, *Mycoplasma* virus P1, *Escherichia* virus 24B, *Escherichia* virus 933W, *Escherichia* virus Min27, *Escherichia* virus PA28, *Escherichia* virus Stx2 II, *Shigella* virus 7502Stx, *Shigella* virus POCJ13, *Escherichia* virus 191, *Escherichia* virus PA2, *Escherichia* virus TL2011, *Shigella* virus VASD, *Burkholderia* virus Bcep22, *Burkholderia* virus Bcepi102, *Burkholderia* virus Bcepmig1, *Burkholderia* virus DC1, *Bordetella* virus BPP1, *Burkholderia* virus BcepC6B, Cellulophaga virus Cba41, Cellulophaga virus Cba172, Dinoroseobacter virus DFL12, *Erwinia* virus Ea9-2, *Erwinia* virus Frozen, *Escherichia* virus phiV10, *Salmonella* virus Epsilon15, *Salmonella* virus SPN1S, *Pseudomonas* virus F116, *Pseudomonas* virus H66, *Escherichia* virus APEC5, *Escherichia* virus APEC7, *Escherichia* virus Bp4, *Escherichia* virus EC1UPM, *Escherichia* virus ECBP1, *Escherichia* virus G7C, *Escherichia* virus IME11, *Shigella* virus Sb1, *Achromobacter* virus Axp3, *Achromobacter* virus JWAlpha, Edwardsiella virus KF1, *Pseudomonas* virus KPP25, *Pseudomonas* virus R18, *Pseudomonas* virus Ab09, *Pseudomonas* virus LIT1, *Pseudomonas* virus PA26, *Pseudomonas* virus Ab22, *Pseudomonas* virus CHU, *Pseudomonas* virus LUZ24, *Pseudomonas* virus PAA2, *Pseudomonas* virus PaP3, *Pseudomonas* virus PaP4, *Pseudomonas* virus TL, *Pseudomonas* virus KPP21, *Pseudomonas* virus LUZ7, *Escherichia* virus N4, *Salmonella* virus 9NA, *Salmonella* virus SP069, *Salmonella* virus BTP1, *Salmonella* virus HK620, *Salmonella* virus P22, *Salmonella* virus ST64T, *Shigella* virus Sf6, *Bacillus* virus Page, *Bacillus* virus Palmer, *Bacillus* virus Pascal, *Bacillus* virus Pony, *Bacillus* virus Pookie, *Escherichia* virus 172-1, *Escherichia* virus ECB2, *Escherichia* virus NJ01, *Escherichia* virus phiEco32, *Escherichia* virus Septima11, *Escherichia* virus SU10, *Brucella* virus Pr, *Brucella* virus Tb, *Escherichia* virus Pollock, *Salmonella* virus FSL SP-058, *Salmonella* virus FSL SP-076, *Helicobacter* virus 1961P, *Helicobacter* virus KHP30, *Helicobacter* virus KHP40, Hamiltonella virus APSE1, *Lactococcus* virus KSY1, Phormidium virus WMP3, Phormidium virus WMP4, *Pseudomonas* virus 119X, Roseobacter virus SIO1, *Vibrio* virus VpV262, *Vibrio* virus VC8, *Vibrio* virus VP2, *Vibrio* virus VPS, *Streptomyces* virus Amela, *Streptomyces* virus phiCAM, *Streptomyces* virus Aaronocolus, *Streptomyces* virus Caliburn, *Streptomyces* virus Danzina, *Streptomyces* virus Hydra, *Streptomyces* virus Izzy, *Streptomyces* virus Lannister, *Streptomyces* virus Lika, *Streptomyces* virus Sujidade, *Streptomyces* virus Zemlya, *Streptomyces* virus ELB20, *Streptomyces* virus R4, *Streptomyces* virus phiHau3, *Mycobacterium* virus Acadian, *Mycobacterium* Baee, *Mycobacterium* virus Reprobate, *Mycobacterium* virus Adawi, *Mycobacterium* virus Bane1, *Mycobacterium* virus BrownCNA, *Mycobacterium* virus Chrisnmich, *Mycobacterium* virus Cooper, *Mycobacterium* virus JAMaL, *Mycobacterium* virus Nigel, *Mycobacterium* virus Stinger, *Mycobacterium* virus Vincenzo, *Mycobacterium* virus Zemanar, *Mycobacterium* virus Apizium, *Mycobacterium* virus Manad, *Mycobacterium* virus Oline, *Mycobacterium* virus Osmaximus, *Mycobacterium* virus Pg1, *Mycobacterium* virus Soto, *Mycobacterium* virus Suffolk, *Mycobacterium* virus Athena, *Mycobacterium* virus Bernardo, *Mycobacterium* virus Gadjet, *Mycobacterium* virus Pipefish, *Mycobacterium* virus Godines, *Mycobacterium* virus Rosebush, *Mycobacterium* virus Babsiella, *Mycobacterium* virus Brujita, *Mycobacterium* virus Che9c, *Mycobacterium* virus Sbash, *Mycobacterium* virus Hawkeye, *Mycobacterium* virus Plot, *Salmonella* virus AG11, *Salmonella* virus Ent1, *Salmonella* virus f18SE, *Salmonella* virus Jersey, *Salmonella* virus L13, *Salmonella* virus LSPA1, *Salmonella* virus SE2, *Salmonella* virus SETP3, *Salmonella* virus SETP7, *Salmonella* virus SETP13, *Salmonella* virus SP101, *Salmonella* virus SS3e, *Salmonella* virus wks13, *Escherichia* virus K1G, *Escherichia* virus K1H, *Escherichia* virus Klind1, *Escherichia* virus Klind2, *Salmonella* virus SP31, *Leuconostoc* virus Lmd1, *Leuconostoc* virus LN03, *Leuconostoc* virus LN04, *Leuconostoc* virus LN12, *Leuconostoc* virus LN6B, *Leuconostoc* virus P793, *Leuconostoc* virus 1A4, *Leuconostoc* virus Ln8, *Leuconostoc* virus Ln9, *Leuconostoc* virus LN25, *Leuconostoc* virus LN34, *Leuconostoc* virus LNTR3, *Mycobacterium* virus Bongo, *Mycobacterium* virus Rey, *Mycobacterium* virus Butters, *Mycobacterium* virus Michelle, *Mycobacterium* virus Charlie, *Mycobacterium* virus Pipsqueaks, *Mycobacterium* virus Xeno, *Mycobacterium* virus Panchino, *Mycobacterium* virus Phrann, *Mycobacterium* virus Redi, *Mycobacterium* virus Skinnyp, *Gordonia* virus BaxterFox, *Gordonia* virus Yeezy, *Gordonia* virus Kita, *Gordonia* virus Zirinka, *Gorrdonia* virus Nymphadora, *Mycobacterium* virus Bignuz, *Mycobacterium* virus Brusacoram, *Mycobacterium* virus Donovan, *Mycobacterium* virus Fishburne, *Mycobacterium* virus Jebeks, *Mycobacterium* virus Malithi, *Mycobacterium* virus Phayonce, *Enterobacter* virus F20, *Klebsiella* virus 1513, *Klebsiella* virus KLPN1, *Klebsiella* virus KP36, *Klebsiella* virus PKP126, *Klebsiella* virus Sushi, *Escherichia* virus AHP42, *Escherichia* virus AHS24, *Escherichia* virus AKS96, *Escherichia* virus C119, *Escherichia* virus E41c, *Escherichia* virus Eb49, *Escherichia* virus Jk06, *Escherichia* virus KP26, *Escherichia* virus Roguel, *Escherichia* virus ACGM12, *Escherichia* virus Rtp, *Escherichia* virus ADB2, *Escherichia* virus JMPW1, *Escherichia* virus JMPW2, *Escherichia* virus T1, *Shigella* virus PSf2, *Shigella* virus Shfl1, *Citrobacter* virus Stevie, *Escherichia* virus TLS, *Salmonella* virus SP126, Cronobacter virus Esp2949-1, *Pseudomonas* virus Ab18, *Pseudomonas* virus Ab19, *Pseudomonas* virus PaMx11, *Arthrobacter* virus Amigo, *Propionibacterium* virus Anatole, *Propionibacterium* virus B3, *Bacillus* virus Andromeda, *Bacillus* virus Blastoid, *Bacillus* virus Curly, *Bacillus* virus Eoghan, *Bacillus* virus Finn, *Bacillus* virus Glittering, *Bacillus* virus Riggi, *Bacillus* virus Taylor, *Gordonia* virus Attis, *Mycobacterium* virus Barnyard, *Mycobacterium* virus Konstantine, *Mycobacterium* virus Predator, *Mycobacterium* virus Bernal13, *Staphylococcus* virus 13, *Staphylococcus* virus 77, *Staphylococcus* virus 108PVL, *Mycobacterium* virus Bron, *Mycobacterium* virus Faith1, *Mycobacterium* virus Joedirt, *Mycobacterium* virus Rumpelstiltskin, *Lactococcus* virus bIL67, *Lactococcus* virus c2, *Lactobacillus* virus c5, *Lactobacillus* virus Ld3, *Lactobacillus* virus Ld17, *Lactobacillus* virus Ld25A, *Lactobacillus* virus LLKu, *Lactobacillus* virus phiLdb, *Cellulophaga* virus Cba121, *Cellulophaga* virus Cba171, *Cellulophaga* virus Cba181, *Cellulophaga* virus ST, *Bacillus* virus 250, *Bacillus* virus IEBH, *Mycobacterium* virus Ardmore, *Mycobacterium* virus Avani, *Mycobacterium* virus Boomer, *Mycobacterium* virus Che8, *Mycobacterium* virus Che9d, *Mycobacterium* virus Deadp, *Mycobacterium* virus Dlane, *Mycobacterium* virus Dorothy, *Mycobacterium* virus Dotproduct, *Mycobacterium* virus Drago, *Mycobacterium* virus Fruitloop, *Mycobacterium* virus Gumbie, *Mycobacterium* virus Ibhubesi, *Mycobacterium* virus Llij, *Mycobacterium* virus Mozy, *Mycobacterium* virus Mutaforma13, *Mycobacterium* virus Pacc40, *Mycobacterium* virus PMC, *Mycobacterium* virus Ramsey, *Mycobacterium* virus Rockyhorror, *Mycobacterium* virus SG4, *Mycobacterium* virus Shauna1, *Mycobacterium* virus Shilan, *Mycobacterium* virus Spartacus, *Mycobacterium* virus Taj, *Mycobacterium* virus Tweety, *Mycobacterium* virus Wee, *Mycobacterium* virus Yoshi, *Salmonella* virus Chi, *Salmonella* virus FSLSP030, *Salmonella* virus FSLSP088, *Salmonella* virus iEPS5, *Salmonella* virus SPN19, *Mycobacterium* virus 244, *Mycobacterium* virus Bask21, *Mycobacterium* virus CJW1, *Mycobacterium* virus Eureka, *Mycobacterium* virus Kostya, *Mycobacterium* virus Porky, *Mycobacterium* virus Pumpkin, *Mycobacterium* virus Sirduracell, *Mycobacterium* virus Toto, *Mycobacterium* virus Corndog, *Mycobacterium* virus Firecracker, *Rhodobacter* virus RcCronus, *Pseudomonas* virus D3112, *Pseudomonas* virus DMS3, *Pseudomonas* virus FHA0480, *Pseudomonas* virus LPB1, *Pseudomonas* virus MP22, *Pseudomonas* virus MP29, *Pseudomonas* virus MP38, *Pseudomonas* virus PA1KOR, *Pseudomonas* virus D3, *Pseudomonas* virus PMG1, *Arthrobacter* virus Decurro, *Gordonia* virus Demosthenes, *Gordonia* virus Katyusha, *Gordonia* virus Kvothe, *Propionibacterium* virus B22, *Propionibacterium* virus Doucette, *Propionibacterium* virus E6, *Propionibacterium* virus G4, *Burkholderia* virus phi6442, *Burkholderia* virus phi1026b, *Burkholderia* virus phiE125, *Edwardsiella* virus eiAU, *Mycobacterium* virus Ff47, *Mycobacterium* virus Muddy, *Mycobacterium* virus Gaia, *Mycobacterium* virus Giles, *Arthrobacter* virus Captnmurica, *Arthrobacter* virus Gordon, *Gordonia* virus GordTnk2, *Paenibacillus* virus Harrison, *Escherichia* virus EK99P1, *Escherichia* virus HK578, *Escherichia* virus JL1, *Escherichia* virus SSL2009a, *Escherichia* virus YD2008s, *Shigella* virus EP23, *Sodalis* virus SO1, *Escherichia* virus HK022, *Escherichia* virus HK75, *Escherichia* virus HK97, *Escherichia* virus HK106, *Escherichia* virus HK446, *Escherichia* virus HK542, *Escherichia* virus HK544, *Escherichia* virus HK633, *Escherichia* virus mEp234, *Escherichia* virus mEp235, *Escherichia* virus mEpX1, *Escherichia* virus mEpX2, *Escherichia* virus mEp043, *Escherichia* virus mEp213, *Escherichia* virus mEp237, *Escherichia* virus mEp390, *Escherichia* virus mEp460, *Escherichia* virus mEp505, *Escherichia* virus mEp506, *Brevibacillus* virus Jenst, *Achromobacter* virus 83-24, *Achromobacter* virus JWX, *Arthrobacter* virus Kellezzio, *Arthrobacter* virus Kitkat, *Arthrobacter* virus Bennie, *Arthrobacter* virus DrRobert, *Arthrobacter* virus Glenn, *Arthrobacter* virus HunterDalle, *Arthrobacter* virus Joann, *Arthrobacter* virus Korra, *Arthrobacter* virus Preamble, *Arthrobacter* virus Pumancara, *Arthrobacter* virus Wayne, *Mycobacterium* virus Alma, *Mycobacterium* virus Arturo, *Mycobacterium* virus Astro, *Mycobacterium* virus Backyardigan, *Mycobac*- terium virus BBPiebs31, *Mycobacterium* virus Benedict, *Mycobacterium* virus Bethlehem, *Mycobacterium* virus Billknuckles, *Mycobacterium* virus Bruns, *Mycobacterium* virus Bxb1, *Mycobacterium* virus Bxz2, *Mycobacterium* virus Che12, *Mycobacterium* virus Cuco, *Mycobacterium* virus D29, *Mycobacterium* virus Doom, *Mycobacterium* virus Ericb, *Mycobacterium* virus Euphoria, *Mycobacterium* virus George, *Mycobacterium* virus Gladiator, *Mycobacterium* virus Goose, *Mycobacterium* virus Hammer, *Mycobacterium* virus Heldan, *Mycobacterium* virus Jasper, *Mycobacterium* virus JC27, *Mycobacterium* virus Jeffabunny, *Mycobacterium* virus JHC117, *Mycobacterium* virus KBG, *Mycobacterium* virus Kssjeb, *Mycobacterium* virus Kugel, *Mycobacterium* virus L5, *Mycobacterium* virus Lesedi, *Mycobacterium* virus LHTSCC, *Mycobacterium* virus lockley, *Mycobacterium* virus Marcell, *Mycobacterium* virus Microwolf, *Mycobacterium* virus Mrgordo, *Mycobacterium* virus Museum, *Mycobacterium* virus Nepal, *Mycobacterium* virus Packman, *Mycobacterium* virus Peaches, *Mycobacterium* virus Perseus, *Mycobacterium* virus Pukovnik, *Mycobacterium* virus Rebeuca, *Mycobacterium* virus Redrock, *Mycobacterium* virus Ridgecb, *Mycobacterium* virus Rockstar, *Mycobacterium* virus Saintus, *Mycobacterium* virus Skipole, *Mycobacterium* virus Solon, *Mycobacterium* virus Switzer, *Mycobacterium* virus SWU1, *Mycobacterium* virus Ta17a, *Mycobacterium* virus Tiger, *Mycobacterium* virus Timshel, *Mycobacterium* virus Trixie, *Mycobacterium* virus Turbido, *Mycobacterium* virus Twister, *Mycobacterium* virus U2, *Mycobacterium* virus Violet, *Mycobacterium* virus Wonder, *Escherichia* virus DE3, *Escherichia* virus HK629, *Escherichia* virus HK630, *Escherichia* virus lambda, *Arthrobacter* virus Laroye, *Mycobacterium* virus Halo, *Mycobacterium* virus Liefie, *Mycobacterium* virus Marvin, *Mycobacterium* virus Mosmoris, *Arthrobacter* virus Circum, *Arthrobacter* virus Mudcat, *Escherichia* virus N15, *Escherichia* virus 9g, *Escherichia* virus JenK1, *Escherichia* virus JenP1, *Escherichia* virus JenP2, *Pseudomonas* virus NP1, *Pseudomonas* virus PaMx25, *Mycobacterium* virus Baka, *Mycobacterium* virus Courthouse, *Mycobacterium* virus Littlee, *Mycobacterium* virus Omega, *Mycobacterium* virus Optimus, *Mycobacterium* virus Thibault, *Polaribacter* virus P12002L, *Polaribacter* virus P12002S, *Nonlabens* virus P12024L, *Nonlabens* virus P12024S, *Thermus* virus P23-45, *Thermus* virus P74-26, *Listeria* virus LP26, *Listeria* virus LP37, *Listeria* virus LP110, *Listeria* virus LP114, *Listeria* virus P70, *Propionibacterium* virus ATCC29399BC, *Propionibacterium* virus ATCC29399BT, *Propionibacterium* virus Attacne, *Propionibacterium* virus Keiki, *Propionibacterium* virus Kubed, *Propionibacterium* virus Lauchelly, *Propionibacterium* virus MrAK, *Propionibacterium* virus Ouroboros, *Propionibacterium* virus P91, *Propionibacterium* virus P105, *Propionibacterium* virus P144, *Propionibacterium* virus P1001, *Propionibacterium* virus P1.1, *Propionibacterium* virus P100A, *Propionibacterium* virus P100D, *Propionibacterium* virus P101A, *Propionibacterium* virus P104A, *Propionibacterium* virus PA6, *Propionibacterium* virus Pacnes201215, *Propionibacterium* virus PAD20, *Propionibacterium* virus PAS50, *Propionibacterium* virus PHL009M11, *Propionibacterium* virus PHL025M00, *Propionibacterium* virus PHL037M02, *Propionibacterium* virus PHL041M10, *Propionibacterium* virus PHL060L00, *Propionibacterium* virus PHL067M01, *Propionibacterium* virus PHL070N00, *Propionibacterium* virus PHL071N05, *Propionibacterium* virus PHL082M03, *Propionibacterium* virus PHL092M00, *Propionibacterium* virus PHL095N00, *Propionibacterium* virus PHL111M01, *Propionibacterium* virus PHL112N00, *Propionibacterium* virus PHL113M01, *Propionibacterium* virus PHL114L00, *Propionibacterium* virus PHL116M00, *Propionibacterium* virus PHL117M00, *Propionibacterium* virus PHL117M01, *Propionibacterium* virus PHL132N00, *Propionibacterium* virus PHL141N00, *Propionibacterium* virus PHL151M00, *Propionibacterium* virus PHL151N00, *Propionibacterium* virus PHL152M00, *Propionibacterium* virus PHL163M00, *Propionibacterium* virus PHL171M01, *Propionibacterium* virus PHL179M00, *Propionibacterium* virus PHL194M00, *Propionibacterium* virus PHL199M00, *Propionibacterium* virus PHL301M00, *Propionibacterium* virus PHL308M00, *Propionibacterium* virus Pirate, *Propionibacterium* virus Procrass1, *Propionibacterium* virus SKKY, *Propionibacterium* virus Solid, *Propionibacterium* virus Stormborn, *Propionibacterium* virus Wizzo, *Pseudomonas* virus PaMx28, *Pseudomonas* virus PaMx74, *Mycobacterium* virus Patience, *Mycobacterium* virus PBI1, *Rhodococcus* virus Pepy6, *Rhodococcus* virus Poco6, *Propionibacterium* virus PFR1, *Streptomyces* virus phiBT1, *Streptomyces* virus phiC31, *Streptomyces* virus TG1, *Caulobacter* virus Karma, *Caulobacter* virus Magneto, *Caulobacter* virus phiCbK, *Caulobacter* virus Rogue, *Caulobacter* virus Swift, *Staphylococcus* virus 11, *Staphylococcus* virus 29, *Staphylococcus* virus 37, *Staphylococcus* virus 53, *Staphylococcus* virus 55, *Staphylococcus* virus 69, *Staphylococcus* virus 71, *Staphylococcus* virus 80, *Staphylococcus* virus 85, *Staphylococcus* virus 88, *Staphylococcus* virus 92, *Staphylococcus* virus 96, *Staphylococcus* virus 187, *Staphylococcus* virus 52a, *Staphylococcus* virus 80alpha, *Staphylococcus* virus CNPH82, *Staphylococcus* virus EW, *Staphylococcus* virus IPLA5, *Staphylococcus* virus IPLA7, *Staphylococcus* virus IPLA88, *Staphylococcus* virus PH15, *Staphylococcus* virus phiETA, *Staphylococcus* virus phiETA2, *Staphylococcus* virus phiETA3, *Staphylococcus* virus phiMR11, *Staphylococcus* virus phiMR25, *Staphylococcus* virus phiNM1, *Staphylococcus* virus phiNM2, *Staphylococcus* virus phiNM4, *Staphylococcus* virus SAP26, *Staphylococcus* virus X2, *Enterococcus* virus FL1, *Enterococcus* virus FL2, *Enterococcus* virus FL3, *Lactobacillus* virus ATCC8014, *Lactobacillus* virus phiJL1, *Pediococcus* virus cIP1, *Aeromonas* virus pIS4A, *Listeria* virus LP302, *Listeria* virus PSA, *Methanobacterium* virus psiM1, *Roseobacter* virus RDJL1, *Roseobacter* virus RDJL2, *Rhodococcus* virus RER2, *Enterococcus* virus BC611, *Enterococcus* virus IMEEF1, *Enterococcus* virus SAP6, *Enterococcus* virus VD13, *Streptococcus* virus SPQS1, *Mycobacterium* virus Papyrus, *Mycobacterium* virus Send513, *Burkholderia* virus KL1, *Pseudomonas* virus 73, *Pseudomonas* virus Ab26, *Pseudomonas* virus Kakheti25, *Escherichia* virus Cajan, *Escherichia* virus Seurat, *Staphylococcus* virus SEP9, *Staphylococcus* virus Sextaec, *Streptococcus* virus 858, *Streptococcus* virus 2972, *Streptococcus* virus ALQ132, *Streptococcus* virus O1205, *Streptococcus* virus Sfi11, *Streptococcus* virus 7201, *Streptococcus* virus DT1, *Streptococcus* virus phiAbc2, *Streptococcus* virus Sfi19, *Streptococcus* virus Sfi21, *Paenibacillus* virus Diva, *Paenibacillus* virus Hb10c2, *Paenibacillus* virus Rani, *Paenibacillus* virus Shelly, *Paenibacillus* virus Sitara, *Paenibacillus* virus Willow, *Lactococcus* virus 712, *Lactococcus* virus ASCC191, *Lactococcus* virus ASCC273, *Lactococcus* virus ASCC281, *Lactococcus* virus ASCC465, *Lactococcus* virus ASCC532, *Lactococcus* virus Bibb29, *Lactococcus* virus bIL170, *Lactococcus* virus CB13, *Lactococcus* virus CB14, *Lactococcus* virus CB19, *Lactococcus* virus CB20, *Lactococcus* virus jj50, *Lactococcus* virus P2, *Lactococcus* virus P008, *Lactococcus* virus sk1, *Lactococcus* virus S14, *Bacillus* virus Slash, *Bacillus* virus Stahl, *Bacillus* virus Staley, *Bacillus* virus Stills, *Gordonia* virus Bachita, *Gordonia* virus ClubL, *Gordonia* virus OneUp, *Gordonia* virus Smoothie, *Gordonia* virus Soups, *Bacillus* virus SPbeta, *Vibrio* virus MAR10, *Vibrio* virus SSP002, *Escherichia* virus AKFV33, *Escherichia* virus BF23, *Escherichia* virus DT57C, *Escherichia* virus EPS7, *Escherichia* virus FFH1, *Escherichia* virus H8, *Escherichia* virus slur09, *Escherichia* virus T5, *Salmonella* virus 118970sa12, *Salmonella* virus Shivani, *Salmonella* virus SPC35, *Salmonella* virus Stitch, *Arthrobacter* virus Tank, *Tsukamurella* virus TIN2, *Tsukamurella* virus TIN3, *Tsukamurella* virus TIN4, *Rhodobacter* virus RcSpartan, *Rhodobacter* virus RcTitan, *Mycobacterium* virus Anaya, *Mycobacterium* virus Angelica, *Mycobacterium* virus Crimd, *Mycobacterium* virus Fionnbarth, *Mycobacterium* virus Jaws, *Mycobacterium* virus Larva, *Mycobacterium* virus Macncheese, *Mycobacterium* virus Pixie, *Mycobacterium* virus TM4, *Bacillus* virus BMBtp2, *Bacillus* virus TP21, *Geobacillus* virus Tp84, *Staphylococcus* virus 47, *Staphylococcus* virus 3a, *Staphylococcus* virus 42e, *Staphylococcus* virus IPLA35, *Staphylococcus* virus phi12, *Staphylococcus* virus phiSLT, *Mycobacterium* virus 32HC, *Rhodococcus* virus RGL3, *Paenibacillus* virus Vegas, *Gordonia* virus Vendetta, *Bacillus* virus Wbeta, *Mycobacterium* virus Wildcat, *Gordonia* virus Twister6, *Gordonia* virus Wizard, *Gordonia* virus Hotorobo, *Gordonia* virus Monty, *Gordonia* virus Woes, *Xanthomonas* virus CP1, *Xanthomonas* virus OP1, *Xanthomonas* virus phi17, *Xanthomonas* virus Xop411, *Xanthomonas* virus Xp10, *Streptomyces* virus TP1604, *Streptomyces* virus YDN12, Alphaproteobacteria virus phiJ1001, *Pseudomonas* virus LKO4, *Pseudomonas* virus M6, *Pseudomonas* virus MP1412, *Pseudomonas* virus PAE1, *Pseudomonas* virus Yua, *Pseudoalteromonas* virus PM2, *Pseudomonas* virus phi6, *Pseudomonas* virus phi8, *Pseudomonas* virus phi12, *Pseudomonas* virus phi13, *Pseudomonas* virus phi2954, *Pseudomonas* virus phiNN, *Pseudomonas* virus phiYY, *Vibrio* virus fs1, *Vibrio* virus VGJ, *Ralstonia* virus RS603, *Ralstonia* virus RSM1, *Ralstonia* virus RSM3, *Escherichia* virus M13, *Escherichia* virus 122, *Salmonella* virus IKe, Acholeplasma virus L51, *Vibrio* virus fs2, *Vibrio* virus VFJ, *Escherichia* virus If1, *Propionibacterium* virus B5, *Pseudomonas* virus Pf1, *Pseudomonas* virus Pf3, *Ralstonia* virus PE226, *Ralstonia* virus RSS1, Spiroplasma virus SVTS2, *Stenotrophomonas* virus PSH1, *Stenotrophomonas* virus SMA6, *Stenotrophomonas* virus SMA7, *Stenotrophomonas* virus SMA9, *Vibrio* virus CTXphi, *Vibrio* virus KSF1, *Vibrio* virus VCY, *Vibrio* virus Vf33, *Vibrio* virus VfO3K6, *Xanthomonas* virus Cflc, Spiroplasma virus C74, Spiroplasma virus R8A2B, Spiroplasma virus SkV1CR23x, *Escherichia* virus FI, *Escherichia* virus Qbeta, *Escherichia* virus BZ13, *Escherichia* virus MS2, *Escherichia* virus alpha3, *Escherichia* virus ID21, *Escherichia* virus ID32, *Escherichia* virus ID62, *Escherichia* virus NC28, *Escherichia* virus NC29, *Escherichia* virus NC35, *Escherichia* virus phiK, *Escherichia* virus St1, *Escherichia* virus WA45, *Escherichia* virus G4, *Escherichia* virus ID52, *Escherichia* virus Talmos, *Escherichia* virus phiX174, Bdellovibrio virus MAC1, Bdellovibrio virus MH2K, Chlamydia virus Chp1, Chlamydia virus Chp2, Chlamydia virus CPAR39, Chlamydia virus CPG1, Spiroplasma virus SpV4, Acholeplasma virus L2, *Pseudomonas* virus PR4, *Pseudomonas* virus PRD1, *Bacillus* virus AP50, *Bacillus* virus Bam35, *Bacillus* virus GIL16, *Bacillus* virus Wip1, *Escherichia* virus phi80, *Escherichia* virus RB42, *Escherichia* virus T2, *Escherichia* virus T3, *Escherichia* virus T6, *Escherichia* virus VT2-Sa, *Escherichia* virus VT1-Sakai, *Escherichia* virus VT2-Sakai, *Escherichia* virus CP-933V, *Escherichia* virus P27, *Escherichia* virus Stx2phi-I, *Escherichia* virus Stx1phi, *Escherichia* virus Stx2phi-II, *Escherichia* virus CP-1639, based on the *Escherichia* virus BP-4795, *Escherichia* virus 86, *Escherichia* virus Min27, *Escherichia* virus 2851, *Escherichia* virus 1717, *Escherichia* virus YYZ-2008, *Escherichia* virus ECO26_P06, *Escherichia* virus EC0103 P15, *Escherichia* virus EC0103_P12, *Escherichia* virus ECO111_P16, *Escherichia* virus ECO111_P11, *Escherichia* virus VT2phi_272, *Escherichia* virus TL-2011c, *Escherichia* virus P13374, *Escherichia* virus Sp5.

In one embodiment, the bacterial delivery vehicles target *E. coli* and includes the capsid of a bacteriophage selected in the group consisting of BW73, B278, D6, D108, E, E1, E24, E41, FI-2, FI-4, FI-5, HI8A, Ffl8B, i, MM, Mu, 025, PhI-5, Pk, PSP3, P1, P1D, P2, P4, S1, Wφ, φK13, φ1, φ2, φ7, φ92, 7 A, 8φ, 9φ, 18, 28-1, 186, 299, HH-*Escherichia* (2), AB48, CM, C4, C16, Dd-VI, E4, E7, E28, FI1, FI3, H, H1, H3, H8, K3, M, N, ND-2, ND-3, ND4, ND-5, ND6, ND-7, Ox-I, Ox-2, Ox-3, Ox-4, Ox-5, Ox-6, PhI-I, RB42, RB43, RB49, RB69, S, SaI-I, Sal-2, Sal-3, Sal-4, Sal-5, Sal-6, TC23, TC45, TuII*-6, TuIP-24, TuII*46, TuIP-60, T2, T4, T6, T35, α1, 1, IA, 3, 3A, 3T+, 5φ, 9266Q, CF0103, HK620, J, K, K1F, m59, no. A, no. E, no. 3, no. 9, N4, sd, T3, T7, WPK, W31, ΔH, φC3888, φK3, φK7, φK12, φV-1, Φ04-CF, Φ05, Φ06, Φ07, φ1, φ1.2, φ20, φ95, φ263, φ1O92, φ1, φ11, Ω8, 1, 3, 7, 8, 26, 27, 28-2, 29, 30, 31, 32, 38, 39, 42, 933W, NN-*Escherichia* (1), Esc-7-11, AC30, CVX-5, C1, DDUP, EC1, EC2, E21, E29, F1, F26S, F27S, Hi, HK022, HK97, HK139, HK253, HK256, K7, ND-I, PA-2, q, S2, T1), T3C, T5, UC-I, w, β4, γ2, λ, ΦD326, φγ, Φ06, Φ7, Φ10, φ80, χ, 2, 4, 4A, 6, 8A, 102, 150, 168, 174, 3000, AC6, AC7, AC28, AC43, AC50, AC57, AC81, AC95, HK243, K10, ZG/3A, 5, 5A, 21EL, H19-J and 933H.

In embodiments wherein the genetic circuit is packaged in a bacterial delivery vehicle, said genetic circuit may comprise a nucleic acid sequence that signals for packaging and the donor cell may express bacteriophage scaffolding proteins. Said sequence that signals for packaging and said bacteriophage scaffolding proteins are chosen by the skilled person depending on the nature of the bacteriophage used as bacterial delivery vehicle.

In some embodiments, the bacterial donor cell and/or bacterial recipient cell disclosed herein may be used in the presence of prebiotics to enhance their growth or any other desired function of the bacterial donor cell and/or bacterial recipient cell. Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carregenaan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

In a further embodiment, the nucleic acid sequence of interest contained in the genetic circuit and placed under the transcriptional control of a repressor binding sequence, encodes a protein conferring resistance to an antibiotic. As used herein, the term "antibiotic" refers to an antibiotic which is selected, for example, from the group consisting in penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; lluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomycin, nalidixice acide, rifampin, derivatives and combination thereof. In particular, the term "protein conferring resistance to an antibiotic" may refer to a protein conferring resistance to any of these antibiotics.

Provided are pharmaceutical or veterinary compositions comprising one or more of the bacterial delivery vehicles produced using the donor cells as disclosed herein, using the methods disclosed herein for producing bacterial delivery vehicles, and a pharmaceutically-acceptable carrier. The present disclosure also provides pharmaceutical or veterinary compositions comprising the recipient or target cells, such as for example a probiotic, where the genetic circuit has been transferred as disclosed herein, and a pharmaceutically-acceptable carrier. The present disclosure also provides pharmaceutical or veterinary compositions comprising the donor cells, such as for example a probiotic, as disclosed herein, i.e. comprising the genetic circuit and expressing the repressor protein, and a pharmaceutically-acceptable carrier. Generally, for pharmaceutical use, the bacterial delivery vehicles may be formulated as a pharmaceutical preparation or compositions comprising at least one bacterial delivery vehicles and at least one pharmaceutically acceptable carrier, diluent or excipient, and optionally one or more further pharmaceutically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such administration forms may be solid, semi-solid or liquid, depending on the manner and route of administration. For example, formulations for oral administration may be provided with an enteric coating that will allow the synthetic bacterial delivery vehicles in the formulation to resist the gastric environment and pass into the intestines. More generally, synthetic bacterial delivery vehicle formulations for oral administration may be suitably formulated for delivery into any desired part of the gastrointestinal tract. In addition, suitable suppositories may be used for delivery into the gastrointestinal tract. Various pharmaceutically acceptable carriers, diluents and excipients useful in bacterial delivery vehicle compositions are known to the skilled person.

The pharmaceutical or veterinary composition according to the disclosure may further comprise a pharmaceutically acceptable vehicle. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidine, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions of the disclosure may be administered orally in the form of a sterile solution or suspension containing other solutes or suspending agents (for example, enough saline or glucose to make the solution isotonic), bile salts, acacia, gelatin, sorbitan monoleate, polysorbate 8o (oleate esters of sorbitol and its anhydrides copolymerized with ethylene oxide) and the like. The particles according to the disclosure can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial delivery vehicles, produced according to the production method disclosed herein, may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, for example, sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Also provided are methods for treating a disease or disorder caused by bacteria, such as a bacterial infection, using the compositions disclosed herein. In this aspect, the genetic circuit including the nucleic acid of interest is transferred in one or more bacteria causing the disease or disorder, i.e. the target cells. The methods include administering a pharmaceutical or veterinary composition disclosed herein, for example, a therapeutically effective amount of a pharmaceutical or veterinary composition disclosed herein, to a subject having a disease or disorder caused by bacteria, such as a bacterial infection, in need of treatment. Further provided is a pharmaceutical or veterinary composition as disclosed herein for use as a medicament, and in particular in the treatment of a disease or disorder caused by bacteria, such as in the treatment of a bacterial infection. Also provided is the use of a pharmaceutical or veterinary composition as disclosed herein for the manufacture of a medicament for treating a disease or disorder caused by bacteria, such as a bacterial infection.

In some embodiments, the subject is a mammal. In some particular embodiments, the subject is a human.

The disease or disorder caused by bacteria may be selected from the group consisting of abdominal cramps, acne vulgaris, acute epiglottitis, arthritis, bacteraemia, bloody diarrhea, botulism, Brucellosis, brain abscess, chancroid venereal disease, Chlamydia, Crohn's disease, conjunctivitis, cholecystitis, colorectal cancer, polyposis, dysbiosis, Lyme disease, diarrhea, diphtheria, duodenal ulcers, endocarditis, erysipelothricosis, enteric fever, fever, glomerulonephritis, gastroenteritis, gastric ulcers, Guillain-Barre syndrome tetanus, gonorrhoea, gingivitis, inflammatory bowel diseases, irritable bowel syndrome, leptospirosis, leprosy, listeriosis, tuberculosis, Lady Widermere syndrome, Legionaire's disease, meningitis, mucopurulent conjunctivitis, multi-drug resistant bacterial infections, multi-drug resistant bacterial carriage, myonecrosis-gas gangrene, *Mycobacterium avium* complex, neonatal necrotizing enterocolitis, nocardiosis, nosocomial infection, otitis, periodontitis, phalyngitis, pneumonia, peritonitis, purpuric fever, Rocky Mountain spotted fever, shigellosis, syphilis, sinusitis, sigmoiditis, septicaemia, subcutaneous abscesses, tularaemia, tracheobronchitis, tonsillitis, typhoid fever, ulcerative colitis, urinary infection and whooping cough.

The bacterial infection may be selected from the group consisting of skin infections such as acne, intestinal infections such as esophagitis, gastritis, enteritis, colitis, sigmoiditis, rectitis, and peritonitis, urinary tract infections, vaginal infections, female upper genital tract infections such as salpingitis, endometritis, oophoritis, myometritis, parametritis and infection in the pelvic peritoneum, respiratory tract infections such as pneumonia, intra-amniotic infections, odontogenic infections, endodontic infections, fibrosis, meningitis, bloodstream infections, nosocomial infection such as catheter-related infections, hospital acquired pneumonia, post-partum infection, hospital acquired gastroenteritis, hospital acquired urinary tract infections, or a combination thereof. In an embodiment, the bacterial infection according to the disclosure is caused by a bacterium presenting an antibiotic resistance. In a particular embodiment, the infection is caused by a bacterium as listed above, a bacterium that can be used as donor or target cell.

Also provided is a method for treating a bacterial infection comprising administering to a subject having a bacterial infection in need of treatment the provided pharmaceutical or veterinary composition, in particular a therapeutically effective amount of the provided pharmaceutical or veterinary composition. A "therapeutically effective amount" is an amount which, when administered to a subject, is needed to treat the targeted disease or disorder, or to produce the desired effect, e.g. is needed to treat the disease or disorder caused by bacteria, in particular a bacterial infection.

A method for reducing the amount of virulent and/or antibiotic resistant bacteria in a bacterial population, in particular in a subject having a bacterial infection, is provided comprising contacting the bacterial population with a pharmaceutical or veterinary composition disclosed herein or with the bacterial delivery vehicles disclosed herein. Further provided is the use of a pharmaceutical or veterinary composition disclosed herein or a bacterial delivery vehicle disclosed herein for the manufacture of a medicament for reducing the amount of virulent and/or antibiotic resistant bacteria in a bacterial population, in particular in a subject having a bacterial infection.

The disclosure also concerns a pharmaceutical or veterinary composition for use in the treatment of a metabolic disorder including, for example, obesity, type 2 diabetes and nonalcoholic fatty liver disease. Indeed, emerging evidence indicates that these disorders are characterized by alterations in the intestinal microbiota composition and its metabolites [31]. The pharmaceutical or veterinary composition may thus be used to deliver in some intestinal bacteria a nucleic acid of interest which can alter the intestinal microbiota composition (e.g. by inducing death of some bacteria) or its metabolites (e.g. by inducing expression, overexpression or secretion of some molecules by said bacteria, for example molecules having a beneficial role on metabolic inflammation). The disclosure also concerns the use of a pharmaceutical or veterinary composition for the manufacture of a medicament for the treatment of a metabolic disorder including, for example, obesity, type 2 diabetes and nonalcoholic fatty liver disease. It also relates to a method for treating a metabolic disorder including, for example, obesity, type 2 diabetes and nonalcoholic fatty liver disease, comprising administering to a subject having a metabolic disorder in need of treatment the provided pharmaceutical or veterinary composition, in particular a therapeutically effective amount of the provided pharmaceutical or veterinary composition.

In a particular embodiment, the disclosure concerns a pharmaceutical or veterinary composition for use in the treatment of pathologies involving bacteria of the human microbiome, such as inflammatory and auto-immune diseases, cancers, infections or brain disorders. The disclosure also relates to a method for treating a pathology involving bacteria of the human microbiome comprising administering to a subject having said pathology and in need of treatment the provided pharmaceutical or veterinary composition, in particular a therapeutically effective amount of the provided pharmaceutical or veterinary composition, and relates to the use of a pharmaceutical or veterinary composition disclosed herein for the manufacture of a medicament for treating a pathology involving bacteria of the human microbiome. Indeed, some bacteria of the microbiome, without triggering any infection, can secrete molecules that will induce and/or enhance inflammatory or auto-immune diseases or cancer development. More specifically, the present disclosure relates also to modulating microbiome composition to improve the efficacy of immunotherapies based, for example, on CAR-T (Chimeric Antigen Receptor T) cells, TIL (Tumor Infiltrating Lymphocytes) and Tregs (Regulatory T cells) also known as suppressor T cells. Modulation of the microbiome composition to improve the efficacy of immunotherapies may also include the use of immune checkpoint inhibitors well known in the art such as, without limitation, PD-1 (programmed cell death protein 1) inhibitor, PD-L1 (programmed death ligand 1) inhibitor and CTLA-4 (cytotoxic T lymphocyte associated protein 4).

Some bacteria of the microbiome can also secrete molecules that will affect the brain.

Therefore, a further object of the disclosure is a method for controlling the microbiome of a subject, comprising administering an effective amount of the pharmaceutical composition as disclosed herein in said subject.

In a particular embodiment, the disclosure also relates to a method for personalized treatment for an individual in need of treatment for a bacterial infection comprising: i) obtaining a biological sample from the individual and determining a group of bacterial DNA sequences from the sample; ii) based on the determining of the sequences, identifying one or more pathogenic bacterial strains or species that were in the sample; and iii) administering to the individual a pharmaceutical composition according to the disclosure capable of recognizing each pathogenic bacterial strain or species identified in the sample and to deliver the packaged genetic circuit.

In an embodiment, the biological sample comprises pathological and non-pathological bacterial species, and subsequent to administering the pharmaceutical or veterinary composition according to the disclosure to the individual, the amount of pathogenic bacteria on or in the individual are reduced, but the amount of non-pathogenic bacteria is not reduced.

In another particular embodiment, the disclosure concerns a pharmaceutical or veterinary composition according to the disclosure for use in order to improve the effectiveness of drugs. Indeed, some bacteria of the microbiome, without being pathogenic by themselves, are known to be able to metabolize drugs and to modify them in ineffective or harmful molecules.

In another particular embodiment, the disclosure concerns the in-situ bacterial production of any compound of interest, including therapeutic compound such as prophylactic and therapeutic vaccine for mammals. The compound of interest, encoded by the nucleic acid of interest comprised in the genetic circuit, can be produced inside the targeted bacteria, secreted from the targeted bacteria or expressed on the surface of the targeted bacteria. In a more particular embodiment, the compound of interest is an antigen expressed on the surface of the targeted bacteria for prophylactic and/or therapeutic vaccination.

The present disclosure also relates to a non-therapeutic use of the compositions disclosed herein. For instance, the non-therapeutic use can be a cosmetic use or a use for improving the well-being of a subject, in particular a subject who does not suffer from a disease. Accordingly, the present disclosure also relates to a cosmetic composition or a non-therapeutic composition comprising the compositions of the disclosure.

The present disclosure further provides kits for use in the transfer of a genetic circuit of interest from a donor cell to a recipient or target cell. In one embodiment, the kit comprises (i) a donor cell expressing a repressor protein; and (ii) a genetic circuit of interest. Said genetic circuit may be as defined above, in particular may comprise an expression cassette into which a nucleic acid of interest may be inserted in functional proximity to (is operably linked to) a repressor binding sequence recognized by the repressor protein. In another embodiment, or in addition, the donor cell of the kit may contain prophage sequences for generation of delivery vehicles, for example, packaging the genetic circuit of interest. The kit may further comprise a recipient or target cell wherein said recipient or target cell fails to express the repressor protein thereby permitting expression of the nucleic acid of interest following transfer into said cells.

In order to better understand the subject matter that is disclosed herein and to exemplify how it may be carried out in practice, embodiments will now be described, by way of non-limiting example, with reference to the accompanying drawings.

Example 1

With specific reference to the examples, it is stressed that the particulars shown are by way of example and for purposes of illustrative discussion of embodiments disclosed herein.

The example below demonstrates the use of interspecific promoter-repressor pairs for use in a novel system for production of delivery vehicles. In this case, the repressor being expressed in trans in a production strain comes from a different bacterial species, ideally phylogenetically different. The use of interspecific repressors is a very advantageous tool to control the expression of a given protein or the transcription of a genetic circuit component only in the strain that contains the heterologous repressor in trans. Nevertheless, one needs to be careful when following this approach and not use repressors that may be found ubiquitously, such as the tryptophan synthesis repressor, since they have been shown to not be orthogonal when transferring them to other species [16]. But since bacteria inhabit environments with different characteristics, they have evolved specific repressors recognizing particular signals that may not be present at all in other organisms. Two recent publication shows that the use of interspecific repressors in E coli is possible [10] [17], representing a source of potential interspecific repressor-operator pairs, even if the inducers are not known. Finally, another solution involves the expression of an inactive Cas9 molecule (dCas9) and a gRNA/ tracrRNA targeting the promoter, RBS or coding sequence of the toxic component. dCas9 does not have nuclease activity but it is able to bind and block transcription from the area targeted by the gRNA [18] [19].

FIG. 1 depicts conditional transcriptional control with an interspecific repressor. On the left, the production strain, containing a packaging prophage and a Ph1F (interspecific) repressor in trans. The payload carries the packaging signal and the desired sequence (actuator) under the control of a $P_{ph1F}$ promoter. Upon packaging of the phagemid particles, target strains can be transduced and the $P_{ph1F}$ promoter will be active since they lack the Ph1F repressor (not present in E. coli). Note that the Ph1F repressor can be replaced with a dCas9+gRNA targeting the promoter, RBS or sequence of the actuator.

Figure 2:
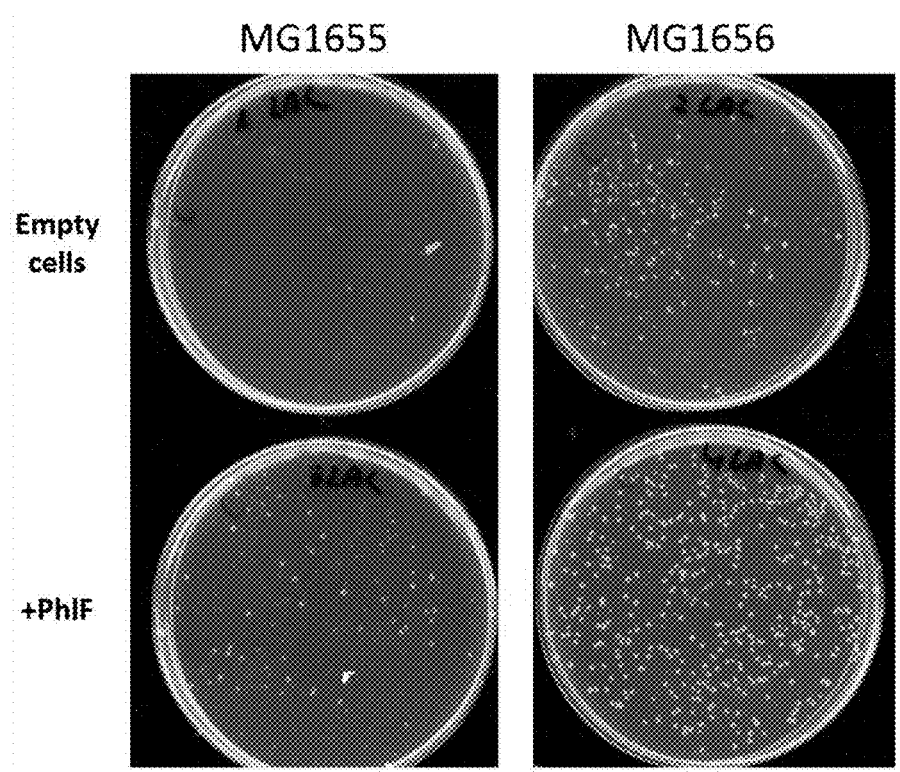
FIG. 2 depicts transformation of Cas9-containing genetic circuits. Plasmids containing Cas9 under the control of a $P_{ph1F}$ promoter and a constitutive sgRNA guide targeting lacZ were transformed into MG1655 (left panels) or MG1656 (right panels). Empty cells (not carrying any other plasmid) are shown on the top; transformed cells containing an extra plasmid encoding the Ph1F repressor are shown at the bottom.

As a proof of concept, plasmids containing Cas9 under the control of the $P_{ph1F}$ promoter (SEQ ID NO: 3), an sgRNA targeting LacZ and a Lambda phage cos signal were constructed. Cas9 targeting LacZ has been previously used in a different setup [20]. Transformation of this plasmid into two strains of E. coli: MG1655 (wt strain) and MG1656 (contains a deletion in the lacZ) was first tried. As expected, the transformation in MG1655 yielded no colonies, since the Cas9 circuit targets its genome and it's toxic. In contrast, transformation into MG1656 gave colonies (FIG. 2). Moreover, transformation into cells containing the Ph1F repressor (SEQ ID NO:1, coding sequence: SEQ ID NO:2) expressed in trans in another plasmid gave colonies in both cases, since the repressor confers protection against Cas9 activity. The differences in size may be due to the fact that the constitutive expression of Cas9 has been shown to be toxic [21].

FIG. 2 depicts transformation of Cas9-containing circuits. Plasmids containing Cas9 under the control of a $P_{ph1F}$ promoter and a constitutive sgRNA guide targeting lacZ (SEQ ID NO:4) were transformed into MG1655 (left panels) or MG1656 (right panels). Empty cells (not carrying any other plasmid) are shown on the top; transformed cells containing an extra plasmid encoding the Ph1F repressor (SEQ ID NO:5) are shown at the bottom.

Figure 3:
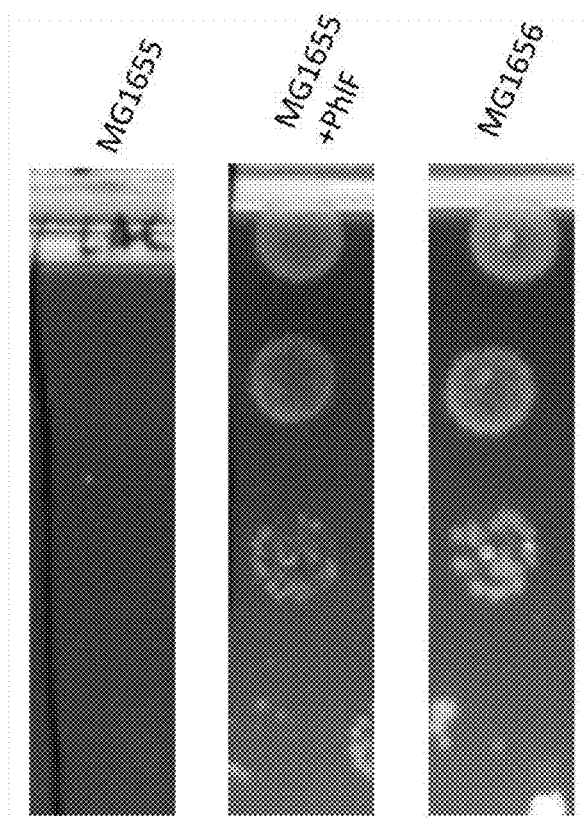
FIG. 3 depicts transduction of Cas9-containing genetic circuits. Phagemids containing Cas9 under the control of a $P_{ph1F}$ promoter and a constitutive sgRNA guide targeting lacZ were transduced into MG1655 (left panel), MG1655 with the Ph1F repressor encoded in a plasmid (center) or MG1656 (right panel).

To test if such a system could also be transduced, the Ph1F repressor was integrated in the genome of the production strain, which also lacks the lacZ gene, and hence, is not targeted by Cas9. The production strain with this plasmid grew normally (data not shown). Phagemids were produced following a standard thermal induction protocol [23] and titrated on MG1655 and MG1656 (FIG. 3). The transduction of Cas9-LacZ circuits into MG1655 gave no colonies, as in the case of transformation, while colonies were recovered in the case of MG1656.

FIG. 3 demonstrates transductions of Cas9-containing circuits. Phagemids containing Cas9 under the control of a $P_{ph1F}$ promoter and a constitutive sgRNA guide targeting lacZ (SEQ ID NO:4) were transduced into MG1655 (left panel), MG1655 with the Ph1F repressor encoded in a plasmid (center) (SEQ ID NO:5) or MG1656 (right panel).

Since the Ph1F repressor does not naturally exist in E. coli, this system can be used to repress the expression of a toxic protein (in this case, Cas9) in the production strain while allowing for expression in another E. coli strain. In this specific case, sgRNA guides that do not target the production strain were used, but since Cas9 is repressed, the system would also allow for the production of phagemid particles encoding sgRNAs targeting its genome.

Example 2

Figure 4:
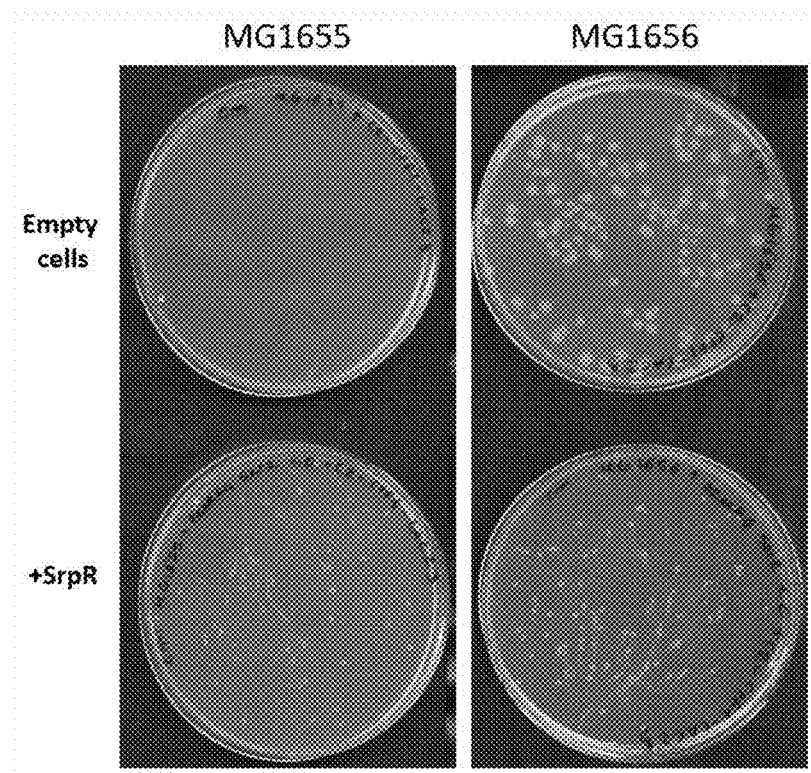
FIG. 4 depicts transformation of Cpf1-containing genetic circuits. Plasmids containing Cpf1 under the control of a $P_{srpR}$ promoter and a constitutive crRNA guide targeting lacZ (p455) were transformed into MG1655 (left panels) or MG1656 (right panels). Empty cells (not carrying any other plasmid) are shown on the top row; transformed cells containing an extra plasmid encoding the SrpR repressor (pRARE4-SrpR-1.0) are shown at the bottom.

Plasmids containing the Cpf1 nuclease under the control of the PsrpR promoter (SEQ ID NO:8), a crRNA targeting LacZ and a Lambda phage cos signal (p455, SEQ ID NO:9) were constructed. Transformation of these plasmids into two strains of E. coli, MG1655 (wild-type strain) and MG1656 (contains a deletion in the lacZ gene), were first performed. As expected, the transformation in MG1655 yielded no colonies, since the Cpf1 circuit targets its genome and it's toxic. In contrast, transformation into MG1656 gave colonies (FIG. 4). Moreover, transformation into cells containing the SrpR repressor expressed in trans in another plasmid (pRARE4-SrpR-1.0, SEQ ID NO:10) gave colonies in both cases, since the repressor confers protection against Cpf1 activity (FIG. 4).

Figure 5:
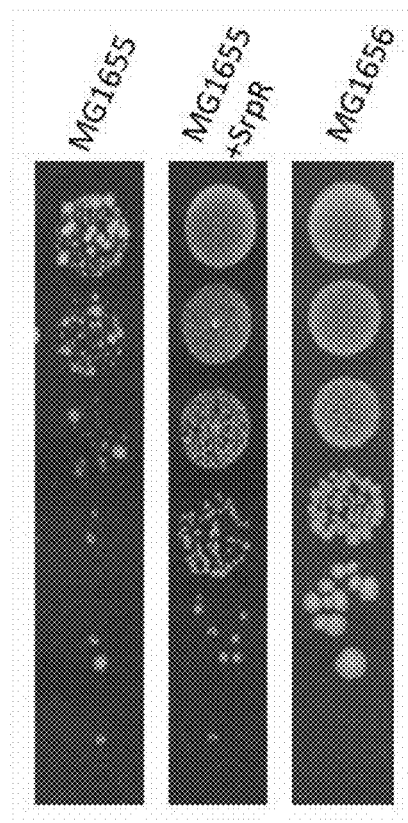
FIG. 5 depicts packaged phagemids containing Cpf1 under the control of a $P_{srpR}$ promoter and a constitutive crRNA guide targeting lacZ (p455) transduced into MG1655 (left panel), MG1655 with the SrpR repressor encoded in a plasmid (center, pRARE4-SrpR-1.0) or MG1656 (right panel).

To test if such a system could also be transduced, the SrpR repressor (SEQ ID NO:6, coding sequence: SEQ ID NO:7) was integrated in the genome of the production strain, which also lacks the lacZ gene, and hence, is not targeted by Cpf1. Packaged phagemids were produced following a standard thermal induction protocol as indicated for the Ph1F repressor data and titrated on MG1655 containing or not the SrpR repressor supplied in trans and MG1656 (FIG. 5). The transduction of Cpf1-LacZ circuits into MG1655 gave a reduction of almost 4 logs in the number of colonies recovered, reflecting the high toxicity of the circuit, while colonies were recovered in the case of MG1655 supplemented with the SrpR repressor to similar numbers as cells not containing the lacZ target (MG1656).

Finally, the addition of a repressor in the genome of the production strain that is able to repress in trans the payload may help reduce the burden of a circuit that would otherwise be constitutively expressed. Cells will be smaller, since their doubling time is reduced due to the plasmid burden, which could be detrimental for upscaling due to longer incubation times needed to reach a specific OD. Moreover, and perhaps more importantly, circuits that contain constitutively expressed components are unstable and prone to break fast, since the cell will find a way to remove the metabolic burden [24]-[30]. This is especially true if these expression levels are high, such as in the case of the Cpf1 circuit shown above: if the circuit breaks during a large-scale fermentation, this could lead to large economic losses.

Figure 6:
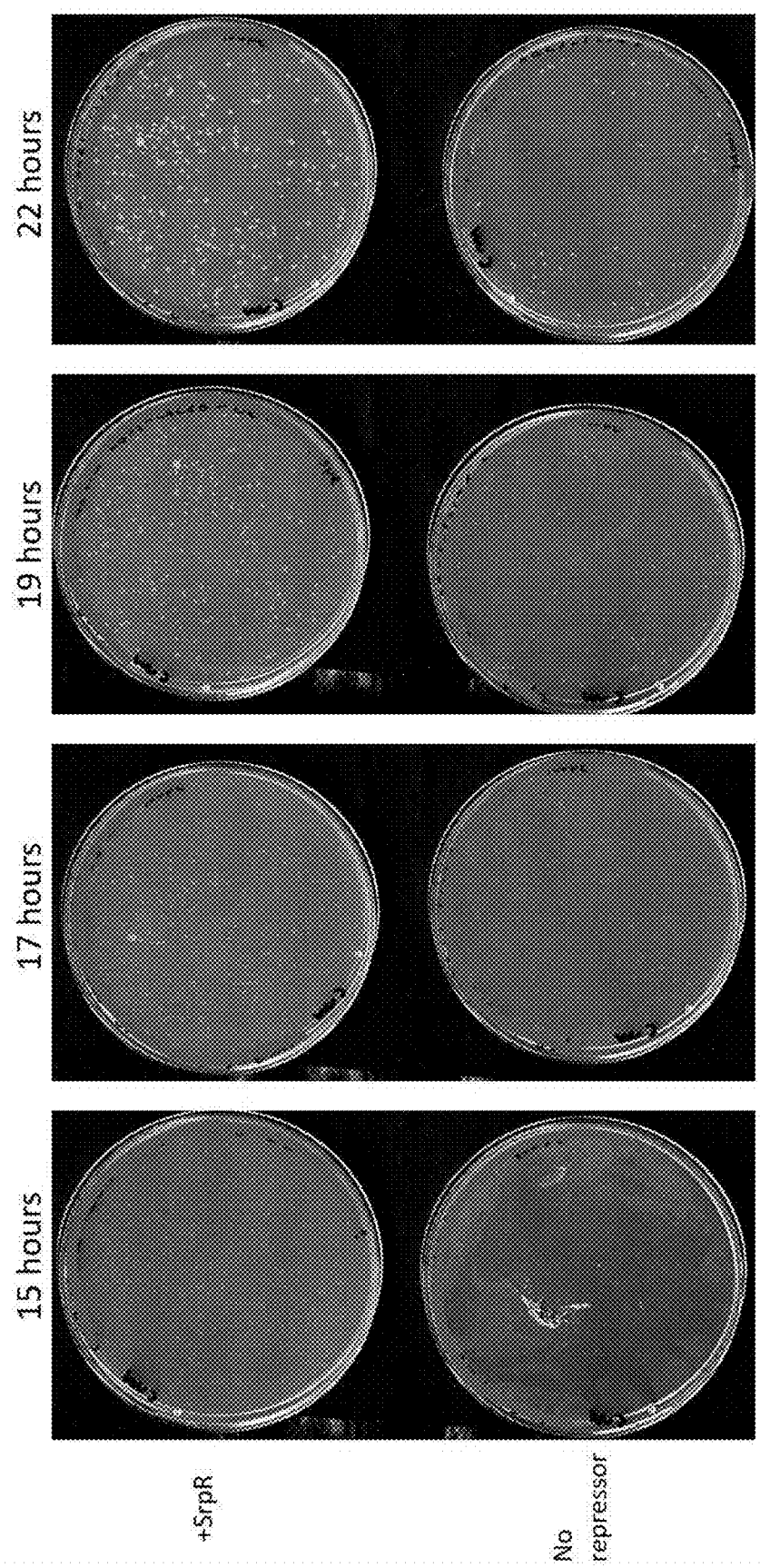
FIG. 6 depicts comparison of colony size of strains with or without the SrpR repressor. Both strains were transformed with a $P_{srpR}$-Cpf1-LacZ genetic circuit (p841). Top panels, cells containing the SrpR in the genome. Bottom panels, cells without the SrpR repressor. Incubation times are shown at the top.

FIG. 6 shows the addition of the SrpR repressor conferring a benefit to a production strain encoding a Cpf1-LacZ circuit in which the expression of Cpf1 is higher than in FIGS. 4 and 5 (p841, SEQ ID NO:11). Colony size after transformation of the $P_{srpR}$-Cpf1-LacZ circuit into a production strain containing the SrpR repressor or not was monitored.

Cells were transformed and incubated on chloramphenicol LB agar overnight at 30° C. and the size of the colonies tracked after 15 h, 17 h, 19 h and 22 h. As can be seen in FIG. 6, colonies are clearly seen at time 17 h in the production strain containing the genomic SrpR repressor, but not in the one without. Even after 22 hours incubations, the colonies of the production strain without repressor are visibly smaller than those containing SrpR, which shows that the introduction of the repressor in trans reduces the metabolic burden in the production strain.

LIST OF REFERENCES CITED

Any references cited in the specification are incorporated by reference herein in their entirety.

[1] L. Marschall, P. Sagmeister, and C. Herwig, "Tunable recombinant protein expression in E. coli: promoter systems and genetic constraints," *Appl. Microbiol. Biotechnol.*, vol. 101, no. 2, pp. 501-512, 2017.

[2] T. Brautaset, R. Lale, and S. Valla, "Positively regulated bacterial expression systems," *Microb. Biotechnol.*, vol. 2, no. 1, pp. 15-30, January 2009.

[3] I. Mijakovic, D. Petranovic, and P. R. Jensen, "Tunable promoters in systems biology," *Curr. Opin. Biotechnol.*, vol. 16, no. 3, pp. 329-335, June 2005.

[4] H. A. de Boer, L. J. Comstock, and M. Vasser, "The tac promoter: a functional hybrid derived from the trp and lac promoters," *Proc. Natl. Acad. Sci. U.S.A*, vol. 80, no. 1, pp. 21-25, January 1983.

[5] L. M. Guzman, D. Belin, M. J. Carson, and J. Beckwith, "Tight regulation, modulation, and high-level expression by vectors containing the arabinose PBAD promoter," *J. Bacteriol.*, vol. 177, no. 14, pp. 4121-4130, July 1995.

[6] A. Skerra, "Use of the tetracycline promoter for the tightly regulated production of a murine antibody fragment in *Escherichia coli*," *Gene*, vol. 151, no. 1, pp. 131-135, December 1994.

[7] N. A. Valdez-Cruz, L. Caspeta, N. O. Pérez, O. T. Ramirez, and M. A. Trujillo-Roldan, "Production of recombinant proteins in *E. coli* by the heat inducible expression system based on the phage lambda pL and/or pR promoters," *Microb. Cell Factories*, vol. 9, p. 18, March 2010.

[8] F. W. Studier and B. A. Moffatt, "Use of bacteriophage T7 RNA polymerase to direct selective high-level expression of cloned genes," *J. Mol. Biol.*, vol. 189, no. 1, pp. 113-130, May 1986.

[9] G. L. Rosano and E. A. Ceccarelli, "Recombinant protein expression in *Escherichia coli*: advances and challenges," *Front. Microbiol.*, vol. 5, April 2014.

[10] B. C. Stanton, A. A. K. Nielsen, A. Tamsir, K. Clancy, T. Peterson, and C. A. Voigt, "Genomic mining of prokaryotic repressors for orthogonal logic gates," *Nat. Chem. Biol.*, vol. 10, no. 2, pp. 99-105, February 2014.

[11] F. Saïda, M. Uzan, B. Odaert, and F. Bontems, "Expression of highly toxic genes in *E. coli*: special strategies and genetic tools," *Curr. Protein Pept. Sci.*, vol. 7, no. 1, pp. 47-56, February 2006.

[12] J. E. Cronan, "Cosmid-Based System for Transient Expression and Absolute Off-to-On Transcriptional Control of *Escherichia coli* Genes," *J. Bacteriol.*, vol. 185, no. 22, pp. 6522-6529, November 2003.

[13] J. E. Cronan, "Improved Plasmid-Based System for Fully Regulated Off-To-On Gene Expression in *Escherichia coli*: Application to Production of Toxic Proteins," *Plasmid*, vol. 69, no. 1, pp. 81-89, January 2013.

[14] D. Bikard et al., "Exploiting CRISPR-Cas nucleases to produce sequence-specific antimicrobials," *Nat. Biotechnol.*, vol. 32, no. 11, pp. 1146-1150, November 2014.

[15] J. Fernandez-Rodriguez, L. Yang, T. E. Gorochowski, D. B. Gordon, and C. A. Voigt, "Memory and Combinatorial Logic Based on DNA Inversions: Dynamics and Evolutionary Stability," *ACS Synth. Biol.*, vol. 4, no. 12, pp. 1361-1372, December 2015.

[16] M. D. Manson and C. Yanofsky, "Tryptophan operon regulation in interspecific hybrids of enteric bacteria.," *J. Bacteriol.*, vol. 126, no. 2, pp. 679-689, May 1976.

[17] A. J. Meyer, T. H. Segall-Shapiro, E. Glassey, J. Zhang, and C. A. Voigt, "*Escherichia coli* 'Marionette' strains with 12 highly optimized small-molecule sensors," *Nat. Chem. Biol.*, vol. 15, no. 2, p. 196, February 2019.

[18] D. Bikard, W. Jiang, P. Samai, A. Hochschild, F. Zhang, and L. A. Marraffini, "Programmable repression and activation of bacterial gene expression using an engineered CRISPR-Cas system," *Nucleic Acids Res.*, vol. 41, no. 15, pp. 7429-7437, August 2013.

[19] L. S. Qi et al., "Repurposing CRISPR as an RNA-Guided Platform for Sequence-Specific Control of Gene Expression," *Cell*, vol. 152, no. 5, pp. 1173-1183, February 2013.

[20] L. Cui and D. Bikard, "Consequences of Cas9 cleavage in the chromosome of *Escherichia coli*," *Nucleic Acids Res.*, vol. 44, no. 9, pp. 4243-4251, May 2016.

[21] S. Cho, D. Choe, E. Lee, S. C. Kim, B. Palsson, and B.-K. Cho, "High-Level dCas9 Expression Induces Abnormal Cell Morphology in *Escherichia coli*," *ACS Synth. Biol.*, vol. 7, no. 4, pp. 1085-1094, April 2018.

[22] J. Fernandez-Rodriguez, C. A. Voigt, "Post-translational control of genetic circuits using Potyvirus proteases." *Nucleic Acids Res.*, vol. 44, no. 13, pp. 6493-6502, July 2016

[23] I. N. Wang, "Lysis Timing and Bacteriophage Fitness" Genetics, vol. 172, no 1, pp. 17-26, January 2006.

[24] S. C. Sleight, B. A. Bartley, J. A. Lieviant, and H. M. Sauro, "Designing and engineering evolutionary robust genetic circuits," J. Biol. Eng., vol. 4, no. 1, p. 12, November 2010, doi: 10.1186/1754-1611-4-12.

[25] M. B. Elowitz and S. Leibler, "A synthetic oscillatory network of transcriptional regulators," Nature, vol. 403, no. 6767, pp. 335-338, January 2000, doi: 10.1038/35002125.

[26] B. R. Glick, "Metabolic load and heterologous gene expression," Biotechnol. Adv., vol. 13, no. 2, pp. 247-261, 1995.

[27] M. Scott, C. W. Gunderson, E. M. Mateescu, Z. Zhang, and T. Hwa, "Interdependence of Cell Growth and Gene Expression: Origins and Consequences," Science, vol. 330, no. 6007, pp. 1099-1102, November 2010, doi: 10.1126/science.1192588.

[28] S. C. Sleight and H. M. Sauro, "Visualization of Evolutionary Stability Dynamics and Competitive Fitness of *Escherichia coli* Engineered with Randomized Multigene Circuits," ACS Synth. Biol., vol. 2, no. 9, pp. 519-528, September 2013, doi: 10.1021/sb400055h.

[29] M. S. Bienick, K. W. Young, J. R. Klesmith, E. E. Detwiler, K. J. Tomek, and T. A. Whitehead, "The Interrelationship between Promoter Strength, Gene Expression, and Growth Rate," PLoS ONE, vol. 9, no. 10, p. e109105, October 2014, doi: 10.1371/journal.pone.0109105.

[30] J. Fernandez-Rodriguez, L. Yang, T. E. Gorochowski, D. B. Gordon, and C. A. Voigt, "Memory and Combinatorial Logic Based on DNA Inversions: Dynamics and Evolutionary Stability," ACS Synth. Biol., vol. 4, no. 12, pp. 1361-1372, December 2015, doi: 10.1021/acssynbio.5b00170.

[31] Tilg et al., *Nature Reviews Immunology*, volume 20, pages 40-54, 2020

What is claimed is:

1. A method of producing packaged phagemids comprising:
    (i) introducing a genetic circuit into a bacterial donor cell expressing a selected repressor protein, wherein said genetic circuit is a phagemid which comprises a nucleic acid of interest under the transcriptional control of a repressor binding sequence recognized by said repressor protein, wherein said repressor protein is not encoded by the phagemid and said repressor protein and/or the repressor binding sequence are derived from a different bacterial species than the bacterial donor cell; and
    (ii) allowing a sufficient amount of time for replication of the phagemid and packaging of the phagemid to form packaged phagemids.

2. The method of claim 1 further comprising a step of collecting the packaged phagemids.

3. The method of claim 1, further comprising a step of purifying the packaged phagemids.

4. The method of claim 1, wherein the bacterial donor cell comprises prophage sequences encoding proteins required in trans for packaging of the phagemid to form packaged phagemids.

5. The method according to claim 1, wherein the repressor protein is selected from the group consisting of AmeR, AmrR, AmtR, ArpA, ArpR, BarA, BarB, BM1P1, BM3R1, BpeR, ButR, CalR1, CampR, CasR, CprB, CymR, Cyp106, DhaR, Ef0113, EthR, FarA, HapR, HemR, HlyIIR, IcaR, IcaR, IfeR, JadR2, KstR, LanK, LitR, LmrA, LuxT, McbR, MmfR, MtrR, NonG, OpaR, Orf2, orfL6, PaaR, PhlF, PqrA, PsbI, PsrA, Q9ZF45, QacR, RmrR, ScbR, SmcR, SmeT, SrpR, TarA, TcmR, Th1R, TtgR, TtgW, TylP, TylQ, UrdK, VanT, VarR, YdeS, YDH1 and YixD.

6. The method of claim 1, wherein the nucleic acid sequence of interest encodes a protein of interest and/or an RNA molecule of interest.

7. The method of claim 6, wherein said protein of interest is a toxic protein.

8. The method of claim 6, wherein said protein of interest is a nuclease.

9. The method of claim 7, wherein said toxic protein is selected from the group consisting of holins, endolysins, restriction enzymes and toxins affecting the survival and/or the growth of the target cell.

10. The method of claim 6, wherein said protein of interest is a therapeutic protein.

11. The method of claim 6, wherein said RNA molecule of interest is selected from the group consisting of mRNA, crRNA, tRNA, iRNA, asRNA, ribozyme RNA, guide RNA and RNA aptamers.

12. The method of claim 1, wherein the nucleic acid sequence of interest encodes a CRISPR nuclease and the genetic circuit further comprises a nucleic acid sequence encoding a guide RNA.

13. The method of claim 12, wherein the nucleic acid sequence encoding a guide RNA is under the transcriptional control of a constitutive promoter.

14. The method of claim 1, wherein the nucleic acid sequence of interest is a nucleic acid selected from the group consisting of a nucleic acid encoding: an RNA, a toxin, an enzyme, a recombinase, a bacterial receptor, a membrane protein, a structural protein, a secreted protein, a protein conferring resistance to an antibiotic, a protein conferring resistance to a drug, a toxic protein, a toxic factor, a virulence protein, a virulence factor, and any combination thereof.

15. The method of claim 1, wherein the nucleic acid sequence of interest is selected from the group consisting of a nucleic acid encoding a Cas nuclease, a Cas9 nuclease, a guide RNA, a toxin, an enzyme, a nuclease, a kinase, a TALEN, a ZFN, a meganuclease, a recombinase, a bacterial receptor, a membrane protein, a structural protein, a secreted protein, a protein conferring resistance to an antibiotic, a protein conferring resistance to a drug, a toxic protein, a toxic factor, a virulence protein, a virulence factor and any combination thereof.

16. The method of claim 14, wherein the RNA is selected from the group consisting of a mRNA, a crRNA, a tRNA, an iRNA (interference RNA), an asRNA (anti-sense RNA), a ribozyme RNA, an RNA aptamer and a guide RNA.

17. The method of claim 14, wherein the enzyme is a nuclease or a kinase.

18. The method of claim 17, wherein the nuclease is selected from the group consisting of a Cas nuclease, a Cas9 nuclease, a TALEN, a ZFN and a meganuclease.

19. The method of claim 1, wherein the nucleic acid of interest comprises a CRISPR locus.

\* \* \* \* \*